US012622419B2

(12) United States Patent
Kandul et al.

(10) Patent No.: US 12,622,419 B2
(45) Date of Patent: May 12, 2026

(54) ENDONUCLEASE SEXING AND STERILIZATION IN INSECTS

(71) Applicant: The Regents of the University of California, Oakland, CA (US)

(72) Inventors: Nikolay P. Kandul, La Jolla, CA (US); Omar S. Akbari, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 1346 days.

(21) Appl. No.: 16/766,212

(22) PCT Filed: Nov. 19, 2018

(86) PCT No.: PCT/US2018/061886
§ 371 (c)(1),
(2) Date: May 21, 2020

(87) PCT Pub. No.: WO2019/103982
PCT Pub. Date: May 31, 2019

(65) Prior Publication Data
US 2020/0367479 A1 Nov. 26, 2020

Related U.S. Application Data

(60) Provisional application No. 62/589,405, filed on Nov. 21, 2017.

(51) Int. Cl.
| | |
|---|---|
| *A01K 67/00* | (2006.01) |
| *A01K 67/68* | (2025.01) |
| *C12N 9/22* | (2006.01) |
| *C12N 15/85* | (2006.01) |
| *C12N 15/90* | (2006.01) |

(52) U.S. Cl.
CPC ............... *A01K 67/68* (2025.01); *C12N 9/22* (2013.01); *C12N 15/8509* (2013.01); *C12N 15/902* (2013.01); *A01K 2217/075* (2013.01); *A01K 2227/706* (2013.01); *C12N 2310/20* (2017.05); *C12N 2800/80* (2013.01)

(58) Field of Classification Search
CPC .................................................. A01K 67/0339
See application file for complete search history.

(56) References Cited

U.S. PATENT DOCUMENTS

| | | | |
|---|---|---|---|
| 2005/0120397 A1* | 6/2005 | Steller ................ | A01K 67/0339 435/325 |
| 2015/0237838 A1* | 8/2015 | Hay ................... | A01K 67/0339 800/13 |
| 2015/0376651 A1 | 12/2015 | Frendewey et al. | |
| 2016/0348120 A1 | 12/2016 | Esvelt et al. | |
| 2017/0306307 A1 | 10/2017 | Zhang et al. | |
| 2017/0306335 A1 | 10/2017 | Zhang et al. | |

FOREIGN PATENT DOCUMENTS

| | | |
|---|---|---|
| WO | 2015/105928 A1 | 7/2015 |
| WO | 2016/106236 | 6/2016 |

OTHER PUBLICATIONS

Xue et al. (2014, Genes, Genomes, Genetics, vol. 4, pp. 2167-2173) (Year: 2014).*

Kanippayoor et al. (2013, Spermatogenesis, vol. 3(2), pp. 1-7). (Year: 2013).*

Kemphues et al. (1982, Cell, vol. 31, pp. 655-670). (Year: 1982).*

Harvey-Samuel et al., "Towards the genetic control of invasive species," Biological Invasions, Springer International Publishing, 19(6), Feb. 21, 2017, pp. 1683-1701.

Hoang et al., "Mechanisms of sex determination and transmission ratio distortion in Aedes aegypti," Parasites & Vectors, 9(1), Dec. 1, 2016, https://link.springer.com/content/pdf/10.1186/s13071-016-133 1-x.pdf.

Kandul et al., "Transforming insect population control with precision guided sterile males with demonstration in flies," Nature Communications, 10(1), Sep. 2, 2019, pp. 1-12.

Nagel et al., "Environment and the Sterile Insect Technique In: 'Sterile Insect Technique," Springer-Verlag, Jan. 1, 2005, pp. 499-524.

Taning et al., "CRISPR/Cas9 in insects: Applications, best practices and biosafety concerns," Journal of Insect Physiology Pergamon Press, vol. 98, Jan. 18, 2017, pp. 245-257.

Fuller et al., "Genetic Analysis of Microtubule Structure: A Beta-Tubulin Mutation Causes the Formation of Aberrant Microtubules in Vivo and in Vitro", The Journal of Cell Biology, vol. 104, No. 9, Mar. 1987, pp. 385-394.

Hammond et al., "A CRISPR-Cas9 Gene Drive System Targeting Female Reproduction in the Malaria Mosquito Vector *Anopheles gambiae*", Nature Biotechnology, vol. 34, No. 1, Dec. 7, 2015, pp. 78-83.

International Search Report and Written Opinion for Application No. PCT/US2018/061886, mailed on Apr. 2, 2019, 20 pages.

Jinek et al., "A Programmable Dual RNA-Guided DNA Endonuclease in Adaptive Bacterial Immunity", Science, vol. 337, No. 6096, 2012, pp. 816-821.

(Continued)

*Primary Examiner* — Anoop K Singh
*Assistant Examiner* — David A Montanari
(74) *Attorney, Agent, or Firm* — Kilpatrick Townsend & Stockton LLP

(57) ABSTRACT

Methods of the disclosed precision guided sterile insect technique (pgSIT) include methods for directing male sexing in a genetically modified insect and methods of producing a progeny of genetically modified sterile male insect egg. These methods include integrating at least one nucleic acid sequence into a genome of a first insect, the at least one nucleic acid sequence having at least one first guide polynucleotide targeting a female-essential genomic sequence that is required for female-specific viability, introducing an endonuclease into a second insect, and genetically crossing the first insect and the second insect thereby producing progeny expressing the endonuclease and the at least one nucleic acid sequence. For male sterility a second guide polynucleotide targets a male sterility genomic sequence that is required for male-specific sterility.

21 Claims, 40 Drawing Sheets

(56)          References Cited

OTHER PUBLICATIONS

Kandul et al., "Transforming Insect Population Control With Precision Guided Sterile Males", Nature, vol. 10, No. 84, Jul. 26, 2018, 34 pages.

Kyrou et al., "A CRISPR-Cas9 Gene Drive Targeting Doublesex Causes Complete Population Suppression ib Caged *Anopheles gambiae* Mosquitoes", Nature Biotechnology, vol. 36, No. 11, 2018, pp. 1062-1069.

Scott et al., "Agricultural Production: Assessment of The Potential Use of Cas9-Mediated Gene Drive Systems for Agricultural Pest Control", Journal of Responsible Innovation, vol. 5, No. S1, Dec. 2017, pp. S98-S120.

Xue et al., "CRISPR/Cas9 Mediates Efficient Conditional Mutagenesis in *Drosophila*", G3 Journal, vol. 4, No. 11, Nov. 2014, pp. 2167-2173.

Yu et al., "Highly Efficient Genome Modifications Mediated by CRISPR/Cas9 in *Drosophila*", Genetics, vol. 195, No. 1, 2013, pp. 289-297.

Adelman et al.; "Control of Mosquito-Borne Infectious Diseases: Sex and Gene Drive"; Trends in Parasitology, Elsevier Current Trends; Feb. 17, 2016; 32(3), pp. 219-229.

Extended European Search Report received in European Patent Application No. 18880475.1, dated Jun. 29, 2021; pp. 1-10.

Galizi et al.; "A CRISPR-Cas9 sex-ratio distortion system for genetic control"; Scientific Reports; Aug. 3, 2016; 6(1); pp. 1-5.

Kondo et al.; "Highly Improved Gene Targeting by Germline-Specific Cas9 Expression in *Drosophilia*"; Genetics; Sep. 3, 2013; 195(3), pp. 715-721.

* cited by examiner

The F1 progeny from the crosses between homozygous single gRNA (sgRNA/sgRNA) and homozygous nos-Cas9 (nos-Cas9/nos-Cas9)

♀ Maternal Cas9

| | Wildtype[w-] ♀ | Wildtype[w-] ♂ | sgRNA[Slx]/sgRNA[Slx] ♀ | sgRNA[Slx]/sgRNA[Slx] ♂ | ♂sgRNA[Slx]/sgRNA[Tra] ♀ | ♂sgRNA[Slx]/sgRNA[Tra] ♂ | ♂sgRNA[Dsx]/sgRNA[Dsx] ♀ | ♂sgRNA[Dsx]/sgRNA[Dsx] ♂ | ♂sgRNA[Dsx]/sgRNA[Tra] ♀ | ♂sgRNA[Dsx]/sgRNA[Tra] ♂ | ♂sgRNA[bTub]/sgRNA[bTub] ♀ | ♂sgRNA[bTub]/sgRNA[bTub] ♂ |
|---|---|---|---|---|---|---|---|---|---|---|---|---|
| ♀ Wildtype[w-] | - | - | 119 | 118 | 69 | 57 | 86 | 63 | | 0 | 80 | 77 |
| ♀ Wildtype[w-] | - | - | 57 | 56 | 80 | 64 | 67 | 61 | | 0 | 92 | 101 |
| ♂ Wildtype[w-] | - | - | 86 | 79 | 72 | 61 | 72 | 75 | | 0 | 88 | 94 |
| ♂ nos-Cas9/nos-Cas9 | 84 | 83 | 0 | 67 | 0 | 56 | 0 | 64 | 0 | 61 | 67 | 65 |
| ♀ nos-Cas9/nos-Cas9 | 70 | 72 | 0 | 65 | 0 | 60 | 0 | 56 | 0 | 53 | 61 | 58 |
| ♀ nos-Cas9/nos-Cas9 | 52 | 49 | 0 | 61 | 0 | 57 | 0 | 54 | 0 | 54 | 63 | 67 |
| ♀ nos-Cas9/nos-Cas9 | - | 0 | 0 | 88 | 0 | 87 | 0 | 113 | 0 | 53 | 115 | 76 |

♂ Paternal Cas9

| | Wildtype[w-] ♀ | Wildtype[w-] ♂ | ♀sgRNA[Slx]/sgRNA[Slx] ♀ | ♀sgRNA[Slx]/sgRNA[Slx] ♂ | ♀sgRNA[Slx]/sgRNA[Tra] ♀ | ♀sgRNA[Slx]/sgRNA[Tra] ♂ | ♀sgRNA[Dsx]/sgRNA[Dsx] ♀ | ♀sgRNA[Dsx]/sgRNA[Dsx] ♂ | ♀sgRNA[Dsx]/sgRNA[Tra] ♀ | ♀sgRNA[Dsx]/sgRNA[Tra] ♂ | ♀sgRNA[bTub]/sgRNA[bTub] ♀ | ♀sgRNA[bTub]/sgRNA[bTub] ♂ |
|---|---|---|---|---|---|---|---|---|---|---|---|---|
| ♂ Wildtype[w-] | - | - | 82 | 88 | 62 | 57 | 65 | 57 | | 0 | 69 | 53 |
| ♂ Wildtype[w-] | - | - | 72 | 67 | 77 | 72 | 63 | 60 | | 0 | 66 | 62 |
| ♂ Wildtype[w-] | - | - | 76 | 69 | 81 | 80 | 73 | 70 | | 0 | 73 | 71 |
| ♂ nos-Cas9/nos-Cas9 | 74 | 70 | 0 | 87 | 0 | 63 | 0 | 91 | 0 | 88 | 87 | 75 |
| ♂ nos-Cas9/nos-Cas9 | 70 | 67 | 0 | 90 | 0 | 72 | 0 | 97 | 0 | 100 | 95 | 86 |
| ♂ nos-Cas9/nos-Cas9 | 87 | 74 | 0 | 82 | 0 | 81 | 0 | 95 | 0 | 87 | 95 | 90 |

Notes: At least ten females and ten males were set up for mating in each cross replicate, and their F1 progeny was scored and examined.

*100% sterility

^ In some cases this is an underestimate due to difficulty to distinguish ♀ from ♂

, each replicate cross of 7♀ x 10 ♂ parents, at the minimum.

FIG. 1G

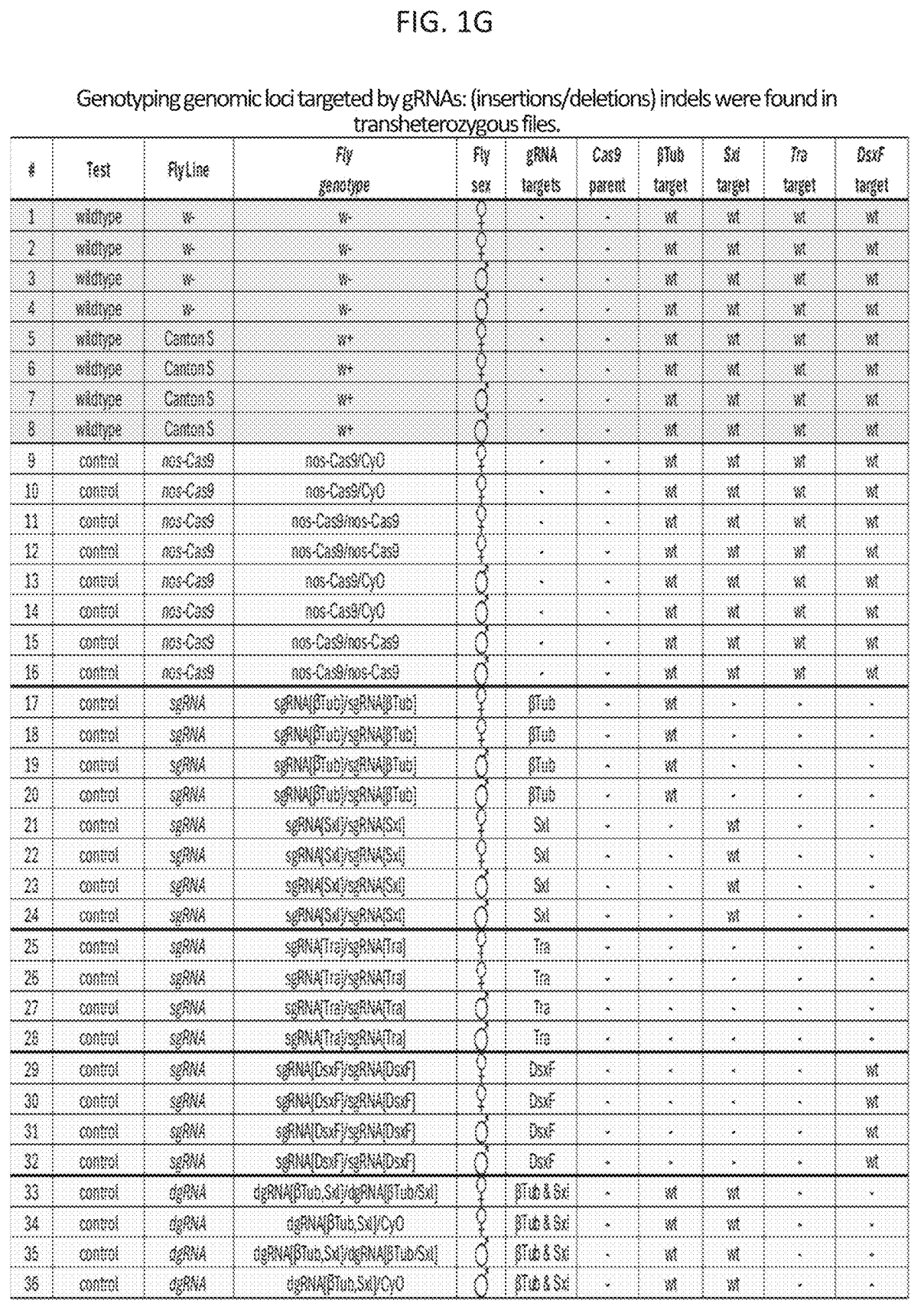

Genotyping genomic loci targeted by gRNAs: (insertions/deletions) indels were found in transheterozygous files.

| # | Test | Fly Line | Fly genotype | Fly sex | gRNA targets | Cas9 parent | βTub target | Sxl target | Tra target | DsxF target |
|---|---|---|---|---|---|---|---|---|---|---|
| 1 | wildtype | w- | w- | | · | · | wt | wt | wt | wt |
| 2 | wildtype | w- | w- | | · | · | wt | wt | wt | wt |
| 3 | wildtype | w- | w- | | · | · | wt | wt | wt | wt |
| 4 | wildtype | w- | w- | | · | · | wt | wt | wt | wt |
| 5 | wildtype | Canton S | w+ | | · | · | wt | wt | wt | wt |
| 6 | wildtype | Canton S | w+ | | · | · | wt | wt | wt | wt |
| 7 | wildtype | Canton S | w+ | | · | · | wt | wt | wt | wt |
| 8 | wildtype | Canton S | w+ | | · | · | wt | wt | wt | wt |
| 9 | control | nos-Cas9 | nos-Cas9/CyO | | · | · | wt | wt | wt | wt |
| 10 | control | nos-Cas9 | nos-Cas9/CyO | | · | · | wt | wt | wt | wt |
| 11 | control | nos-Cas9 | nos-Cas9/nos-Cas9 | | · | · | wt | wt | wt | wt |
| 12 | control | nos-Cas9 | nos-Cas9/nos-Cas9 | | · | · | wt | wt | wt | wt |
| 13 | control | nos-Cas9 | nos-Cas9/CyO | | · | · | wt | wt | wt | wt |
| 14 | control | nos-Cas9 | nos-Cas9/CyO | | · | · | wt | wt | wt | wt |
| 15 | control | nos-Cas9 | nos-Cas9/nos-Cas9 | | · | · | wt | wt | wt | wt |
| 16 | control | nos-Cas9 | nos-Cas9/nos-Cas9 | | · | · | wt | wt | wt | wt |
| 17 | control | sgRNA | sgRNA[βTub]/sgRNA[βTub] | | βTub | · | wt | · | · | · |
| 18 | control | sgRNA | sgRNA[βTub]/sgRNA[βTub] | | βTub | · | wt | · | · | · |
| 19 | control | sgRNA | sgRNA[βTub]/sgRNA[βTub] | | βTub | · | wt | · | · | · |
| 20 | control | sgRNA | sgRNA[βTub]/sgRNA[βTub] | | βTub | · | wt | · | · | · |
| 21 | control | sgRNA | sgRNA[Sxl]/sgRNA[Sxl] | | Sxl | · | · | wt | · | · |
| 22 | control | sgRNA | sgRNA[Sxl]/sgRNA[Sxl] | | Sxl | · | · | wt | · | · |
| 23 | control | sgRNA | sgRNA[Sxl]/sgRNA[Sxl] | | Sxl | · | · | wt | · | · |
| 24 | control | sgRNA | sgRNA[Sxl]/sgRNA[Sxl] | | Sxl | · | · | wt | · | · |
| 25 | control | sgRNA | sgRNA[Tra]/sgRNA[Tra] | | Tra | · | · | · | · | · |
| 26 | control | sgRNA | sgRNA[Tra]/sgRNA[Tra] | | Tra | · | · | · | · | · |
| 27 | control | sgRNA | sgRNA[Tra]/sgRNA[Tra] | | Tra | · | · | · | · | · |
| 28 | control | sgRNA | sgRNA[Tra]/sgRNA[Tra] | | Tra | · | · | · | · | · |
| 29 | control | sgRNA | sgRNA[DsxF]/sgRNA[DsxF] | | DsxF | · | · | · | · | wt |
| 30 | control | sgRNA | sgRNA[DsxF]/sgRNA[DsxF] | | DsxF | · | · | · | · | wt |
| 31 | control | sgRNA | sgRNA[DsxF]/sgRNA[DsxF] | | DsxF | · | · | · | · | wt |
| 32 | control | sgRNA | sgRNA[DsxF]/sgRNA[DsxF] | | DsxF | · | · | · | · | wt |
| 33 | control | dgRNA | dgRNA[βTub,Sxl]/dgRNA[βTub,Sxl] | | βTub & Sxl | · | wt | wt | · | · |
| 34 | control | dgRNA | dgRNA[βTub,Sxl]/CyO | | βTub & Sxl | · | wt | wt | · | · |
| 35 | control | dgRNA | dgRNA[βTub,Sxl]/dgRNA[βTub,Sxl] | | βTub & Sxl | · | wt | wt | · | · |
| 36 | control | dgRNA | dgRNA[βTub,Sxl]/CyO | | βTub & Sxl | · | wt | wt | · | · |

FIG. 1G continued

| # | Test | Fly Line | Fly genotype | Fly sex | gRNA targets | Cas9 parent | βTub target | Sxl target | Tra target | DsxF target |
|---|------|----------|--------------|---------|--------------|-------------|-------------|------------|------------|-------------|
| 37 | control | dgRNA | dgRNA[βTub,Tra]/dgRNA[βTub/Tra] | ♀ | βTub & Tra | - | wt | - | - | - |
| 38 | control | dgRNA | dgRNA[βTub,Tra]/CyO | ♀ | βTub & Tra | - | wt | - | - | - |
| 39 | control | dgRNA | dgRNA[βTub,Tra]/dgRNA[βTub/Tra] | ♂ | βTub & Tra | - | wt | - | - | - |
| 40 | control | dgRNA | dgRNA[βTub,Tra]/CyO | ♂ | βTub & Tra | - | wt | - | - | - |
| 41 | control | dgRNA | dgRNA[βTub,DsxF]/dgRNA[βTub/DsxF] | ♀ | βTub & DsxF | - | wt | - | - | wt |
| 42 | control | dgRNA | dgRNA[βTub,DsxF]/CyO | ♀ | βTub & DsxF | - | wt | - | - | wt |
| 43 | control | dgRNA | dgRNA[βTub,DsxF]/dgRNA[βTub/DsxF] | ♂ | βTub & DsxF | - | wt | - | - | wt |
| 44 | control | dgRNA | dgRNA[βTub,DSxF]/CyO | ♂ | βTub & DsxF | - | wt | - | - | wt |
| 45 | experiment | Cas9 & sgRNA | sgRNA[βTub]/+; nos-Cas9/+ | ♀ | βTub | ♀ | indels | - | - | - |
| 46 | experiment | Cas9 & sgRNA | sgRNA[βTub]/+; nos-Cas9/+ | ♀ | βTub | ♂ | indels | - | - | - |
| 47 | experiment | Cas9 & sgRNA | sgRNA[βTub]/+; nos-Cas9/+ | ♂ | βTub | ♀ | indels | - | - | - |
| 48 | experiment | Cas9 & sgRNA | sgRNA[βTub]/+; nos-Cas9/+ | ♂ | βTub | ♂ | indels | - | - | - |
| 49 | experiment | Cas9 & sgRNA | sgRNA[Sxl]/+; nos-Cas9/+ | ♀ | Sxl | ♀ | - | indels | - | - |
| 50 | experiment | Cas9 & sgRNA | sgRNA[Sxl]/+; nos-Cas9/+ | ♀ | Sxl | ♂ | - | indels | - | - |
| 51 | experiment | Cas9 & sgRNA | sgRNA[Tra]/+; nos-Cas9/+ | ♀ | Tra | ♀ | - | - | indels | - |
| 52 | experiment | Cas9 & sgRNA | sgRNA[Tra]/+; nos-Cas9/+ | ♀ | Tra | ♂ | - | - | indels | - |
| 53 | experiment | Cas9 & sgRNA | sgRNA[Tra]/+; nos-Cas9/+ | ♂ | Tra | ♀ | - | - | indels | - |
| 54 | experiment | Cas9 & sgRNA | sgRNA[Tra]/+; nos-Cas9/+ | ♂ | Tra | ♂ | - | - | indels | - |
| 55 | experiment | Cas9 & sgRNA | sgRNA[DsxF]/+; nos-Cas9/+ | ♀ | DsxF | ♀ | - | - | - | indels |
| 56 | experiment | Cas9 & sgRNA | sgRNA[DsxF]/+; nos-Cas9/+ | ♀ | DsxF | ♂ | - | - | - | indels |
| 57 | experiment | Cas9 & sgRNA | sgRNA[DsxF]/+; nos-Cas9/+ | ♂ | DsxF | ♀ | - | - | - | indels |
| 58 | experiment | Cas9 & sgRNA | sgRNA[DsxF]/+; nos-Cas9/+ | ♂ | DsxF | ♂ | - | - | - | indels |
| 59 | experiment | Cas9 & gRNAs | dgRNA[βTub, Sxl]/+; nos-Cas9/+ | ♂ | βTub & Sxl | ♀ | indels | indels | - | - |
| 60 | experiment | Cas9 & gRNAs | dgRNA[βTub, Sxl]/+; nos-Cas9/+ | ♂ | βTub & Sxl | ♀ | indels | indels | - | - |
| 61 | experiment | Cas9 & gRNAs | dgRNA[βTub, Sxl]/+; nos-Cas9/+ | ♂ | βTub & Sxl | ♂ | indels | indels | - | - |
| 62 | experiment | Cas9 & gRNAs | dgRNA[βTub, Sxl]/+; nos-Cas9/+ | ♀ | βTub & Sxl | ♂ | indels | indels | - | - |
| 63 | experiment | dgRNA+loaded Cas9 | dgRNA[βTub, Sxl]/+; TM3,sb/+ | ♂ | βTub & Sxl | ♀ | indels | indels | - | - |
| 64 | experiment | dgRNA+loaded Cas10 | dgRNA[βTub, Sxl]/+; TM3,sb/+ | ♂ | βTub & Sxl | ♀ | indels | indels | - | - |
| 65 | experiment | dgRNA+loaded Cas11 | dgRNA[βTub, Sxl]/+; TM3,sb/+ | ♂ | βTub & Sxl | ♀ | indels | indels | - | - |
| 66 | experiment | dgRNA+loaded Cas12 | dgRNA[βTub, Sxl]/+; TM3,sb/+ | ♂ | βTub & Sxl | ♀ | indels | indels | - | - |
| 67 | experiment | Cas9+loaded dgRNA | CyO/+; nos-Cas9/+ | ♂ | βTub & Sxl | ♀ | wt | wt | - | - |
| 68 | experiment | Cas9+loaded dgRNA | CyO/+; nos-Cas9/+ | ♂ | βTub & Sxl | ♂ | wt | wt | - | - |
| 69 | experiment | Cas9+loaded dgRNA | CyO/+; nos-Cas9/+ | ♀ | βTub & Sxl | ♀ | wt | wt | - | - |
| 70 | experiment | Cas9+loaded dgRNA | CyO/+; nos-Cas9/+ | ♀ | βTub & Sxl | ♂ | wt | wt | - | - |

FIG. 1G continued

| # | Test | Fly Line | Fly genotype | Fly sex | gRNA targets | Cas9 parent | βTub target | Sxl target | Tra target | DsxF target |
|---|------|----------|--------------|---------|--------------|-------------|-------------|-----------|-----------|-------------|
| 71 | experiment | Cas9 & dgRNA | dgRNA[βTub,Tra]/+; nos-Cas9/+ | ♀ | βTub & Tra | ♂ | indels | - | indels | - |
| 72 | experiment | Cas9 & dgRNA | dgRNA[βTub,Tra]/+; nos-Cas9/+ | ♂ | βTub & Tra | ♂ | indels | - | indels | - |
| 73 | experiment | Cas9 & dgRNA | dgRNA[βTub,Tra]/+; nos-Cas9/+ | ♂ | βTub & Tra | ♀ | indels | - | indels | - |
| 74 | experiment | Cas9 & dgRNA | dgRNA[βTub,Tra]/+; nos-Cas9/+ | ♂ | βTub & Tra | ♀ | indels | - | indels | - |
| 75 | experiment | Cas9 & dgRNA | dgRNA[βTub,Tra]/+; nos-Cas9/+ | ♀ | βTub & Tra | ♂ | indels | - | indels | - |
| 76 | experiment | Cas9 & dgRNA | dgRNA[βTub,Tra]/+; nos-Cas9/+ | ♀ | βTub & Tra | ♂ | indels | - | indels | - |
| 77 | experiment | Cas9 & dgRNA | dgRNA[βTub,Tra]/+; nos-Cas9/+ | ♀ | βTub & Tra | ♀ | indels | - | indels | - |
| 78 | experiment | Cas9 & dgRNA | dgRNA[βTub,Tra]/+; nos-Cas9/+ | ♀ | βTub & Tra | ♀ | indels | - | indels | - |
| 79 | experiment | dgRNA+loaded Cas9 | dgRNA[βTub,Tra]/+; TM3,Sb/+ | ♀ | βTub & Tra | ♂ | indels | - | indels | - |
| 80 | experiment | dgRNA+loaded Cas9 | dgRNA[βTub,Tra]/+; TM3,Sb/+ | ♀ | βTub & Tra | ♂ | indels | - | indels | - |
| 81 | experiment | dgRNA+loaded Cas9 | dgRNA[βTub,Tra]/+; TM3,Sb/+ | ♀ | βTub & Tra | ♀ | indels | - | indels | - |
| 82 | experiment | dgRNA+loaded Cas9 | dgRNA[βTub,Tra]/+; TM3,Sb/+ | ♀ | βTub & Tra | ♀ | indels | - | indels | - |
| 83 | experiment | Cas9+loaded dgRNA | Cyo/+;nos-Cas9/+ | ♀ | βTub & Tra | ♂ | wt | - | wt | - |
| 84 | experiment | Cas9+loaded dgRNA | Cyo/+;nos-Cas9/+ | ♂ | βTub & Tra | ♂ | wt | - | wt | - |
| 85 | experiment | Cas9+loaded dgRNA | Cyo/+;nos-Cas9/+ | ♂ | βTub & Tra | ♂ | wt | - | wt | - |
| 86 | experiment | Cas9+loaded dgRNA | Cyo/+;nos-Cas9/+ | ♀ | βTub & Tra | ♂ | wt | - | wt | - |
| 87 | experiment | Cas9 & dgRNA | dgRNA[βTub,DsxF]/+; nos-Cas9/+ | ♂ | βTub & DsxF | ♀ | indels | - | - | indels |
| 88 | experiment | Cas9 & dgRNA | dgRNA[βTub,DsxF]/+; nos-Cas9/+ | ♀ | βTub & DsxF | ♂ | indels | - | - | indels |
| 89 | experiment | Cas9 & dgRNA | dgRNA[βTub,DsxF]/+; nos-Cas9/+ | ♀ | βTub & DsxF | ♀ | indels | - | - | indels |
| 90 | experiment | Cas9 & dgRNA | dgRNA[βTub,DsxF]/+; nos-Cas9/+ | ♀ | βTub & DsxF | ♀ | indels | - | - | indels |
| 91 | experiment | Cas9 & dgRNA | dgRNA[βTub,DsxF]/+; nos-Cas9/+ | ♂ | βTub & DsxF | ♂ | indels | - | - | indels |
| 92 | experiment | Cas9 & dgRNA | dgRNA[βTub,DsxF]/+; nos-Cas9/+ | ♀ | βTub & DsxF | ♂ | indels | - | - | indels |
| 93 | experiment | Cas9 & dgRNA | dgRNA[βTub,DsxF]/+; nos-Cas9/+ | ♀ | βTub & DsxF | ♀ | indels | - | - | indels |
| 94 | experiment | Cas9 & dgRNA | dgRNA[βTub,DsxF]/+; nos-Cas9/+ | ♂ | βTub & DsxF | ♀ | indels | - | - | indels |
| 95 | experiment | dgRNA+loaded Cas9 | dgRNA[βTub,DsxF]/+; TM3,Sb/+ | ♂ | βTub & DsxF | ♀ | indels | - | - | indels |
| 96 | experiment | dgRNA+loaded Cas9 | dgRNA[βTub,DsxF]/+; TM3,Sb/+ | ♀ | βTub & DsxF | ♂ | indels | - | - | indels |
| 97 | experiment | dgRNA+loaded Cas9 | dgRNA[βTub,DsxF]/+; TM3,Sb/+ | ♀ | βTub & DsxF | ♂ | indels | - | - | indels |
| 98 | experiment | dgRNA+loaded Cas9 | dgRNA[βTub,DsxF]/+; TM3,Sb/+ | ♂ | βTub & DsxF | ♂ | indels | - | - | indels |
| 99 | experiment | Cas9+loaded dgRNA | Cyo/+;nos-Cas9/+ | ♂ | βTub & DsxF | ♀ | wt | - | - | wt |
| 100 | experiment | Cas9+loaded dgRNA | Cyo/+;nos-Cas9/+ | ♀ | βTub & DsxF | ♀ | wt | - | - | wt |
| 101 | experiment | Cas9+loaded dgRNA | Cyo/+;nos-Cas9/+ | ♀ | βTub & DsxF | ♀ | wt | - | - | wt |
| 102 | experiment | Cas9+loaded dgRNA | Cyo/+;nos-Cas9/+ | ♀ | βTub & DsxF | ♀ | wt | - | - | wt |

The F1 progeny from the crosses between homozygous double gRNA (sgRNA/dgRNA) and homozygous Cas9(Cas9/Cas9) lines

| | ♀ Maternal Cas9 | | | | | | | | | | | | | |
|---|---|---|---|---|---|---|---|---|---|---|---|---|---|---|
| | ♂ Wildtype [w-] | | | dgRNA(bTub, Sxl)/sgRNA(bTub, Sxl) | | | | dgRNA(bTub, Tra)/sgRNA(bTub, Tra) | | | | dgRNA(bTub,DsxF)/dgRNA(bTub,DsxF) | | | |
| | ♀ | ♂ | ♀ | ♀ | ♂ | ♂* | ♀** | ♀ | ♂ | ♂* | ♀** | ♀ | ♂ | ♂* | ♀** |
| ♀ Wildtype[w-] | - | - | - | 106 | 102 | 0 | 0 | 103 | 106 | 0 | 0 | 96 | 91 | 0 | 0 |
| ♀ Wildtype[w-] | - | - | - | 103 | 112 | 0 | 0 | 79 | 86 | 0 | 0 | 106 | 103 | 0 | 0 |
| ♀ Wildtype[w-] | - | - | - | 116 | 113 | 0 | 0 | 83 | 75 | 0 | 0 | 108 | 101 | 0 | 0 |
| ♀ nos-Cas9/nos-Cas9 | 84 | 83 | 0 | 0 | 0 | 104 | 0 | 0 | 0 | 65 | 48 | 0 | 0 | 74 | 58 |
| ♀ nos-Cas9/nos-Cas9 | 70 | 72 | 0 | 0 | 0 | 91 | 0 | 0 | 0 | 81 | 79 | 0 | 0 | 72 | 69 |
| ♀ nos-Cas9/nos-Cas9 | 52 | 49 | 0 | 0 | 0 | 121 | 0 | 0 | 0 | 119 | 105 | 0 | 0 | 71 | 77 |
| ♀ nos-Cas9/nos-Cas9 | - | - | - | 0 | 0 | 146 | 0 | 0 | 0 | 90 | 73 | 0 | 0 | 93 | 61 |
| ♀ Ubi-Cas9/Ubi-Cas9 | 54 | 58 | 0 | 0 | 0 | 91 | 0 | 0 | 0 | 61 | 44 | 0 | 0 | 106 | 91 |
| ♀ Ubi-Cas9/Ubi-Cas9 | 51 | 52 | 0 | 0 | 0 | 77 | 0 | 0 | 0 | 53 | 48 | 0 | 0 | 87 | 72 |
| ♀ Ubi-Cas9/Ubi-Cas9 | 66 | 65 | 0 | 0 | 0 | 113 | 0 | 0 | 0 | 58 | 51 | 0 | 0 | 116 | 105 |
| ♀ Ubi-Cas9/Ubi-Cas9 | - | - | - | 0 | 0 | 140 | 0 | 0 | 0 | 44 | 41 | 0 | 0 | 112 | 114 |
| ♀ vas-Cas9/vas-Cas9 | 84 | 87 | 0 | 0 | 0 | 176 | 0 | 0 | 0 | 108 | 69 | 0 | 0 | 121 | 76 |
| ♀ vas-Cas9/vas-Cas9 | 47 | 54 | 0 | 0 | 0 | 75 | 0 | 0 | 0 | 66 | 57 | 0 | 0 | 71 | 65 |
| ♀ vas-Cas9/vas-Cas9 | 95 | 76 | 0 | 0 | 0 | 96 | 0 | 0 | 0 | 61 | 64 | 0 | 0 | 84 | 78 |
| ♀ vas-Cas9/vas-Cas9 | - | - | - | 0 | 0 | 172 | 0 | 0 | 0 | 86 | 77 | 0 | 0 | 86 | 65 |

| | ♂ Paternal Cas9 | | | | | | | | | | | | | |
|---|---|---|---|---|---|---|---|---|---|---|---|---|---|---|
| | ♀ Wildtype [w-] | | | sgRNA(Sxl)/sgRNA(Sxl) | | | | sgRNA(Sxl)/sgRNA(Tra) | | | | sgRNA(DsxF)/sgRNA(DsxF) | | | |
| | ♀ | ♂ | ♀ | ♀ | ♂ | ♂* | ♀** | ♀ | ♂ | ♂* | ♀** | ♀ | ♂ | ♂* | ♀** |
| ♂ Wildtype[w-] | - | - | - | 111 | 99 | 0 | 0 | 82 | 61 | 0 | 0 | 77 | 77 | 0 | 0 |
| ♂ Wildtype[w-] | - | - | - | 121 | 110 | 0 | 0 | 88 | 65 | 0 | 0 | 82 | 76 | 0 | 0 |
| ♂ Wildtype[w-] | - | - | - | 11 | 96 | 0 | 0 | 83 | 61 | 0 | 0 | 88 | 88 | 0 | 0 |
| ♂ nos-Cas9/nos-Cas9 | 74 | 70 | 0 | 0 | 0 | 65 | 0 | 0 | 63 | | 67 | 0 | | 57 | 53 |
| ♂ nos-Cas9/nos-Cas9 | 70 | 67 | 0 | 0 | 0 | 127 | 0 | 0 | 72 | | 70 | 0 | | 108 | 130 |
| ♂ nos-Cas9/nos-Cas9 | 87 | 74 | 0 | 0 | 0 | 86 | 0 | 0 | 61 | | 79 | 0 | | 63 | 58 |
| ♂ nos-Cas9/nos-Cas9 | - | - | - | 0 | 0 | 111 | 0 | 0 | 0 | 83 | 54 | 0 | 0 | 59 | 40 |
| ♂ Ubi-Cas9/Ubi-Cas9 | 52 | 60 | 0 | 0 | 0 | 87 | 0 | 0 | 0 | 53 | 49 | 0 | 0 | 96 | 83 |
| ♂ Ubi-Cas9/Ubi-Cas9 | 54 | 51 | 0 | 0 | 0 | 97 | 0 | 0 | 0 | 46 | 41 | 0 | 0 | 68 | 42 |
| ♂ Ubi-Cas9/Ubi-Cas9 | 58 | 53 | 0 | 0 | 0 | 106 | 0 | 0 | 0 | 68 | 71 | 0 | 0 | 61 | 52 |
| ♂ Ubi-Cas9/Ubi-Cas9 | - | - | - | 0 | 0 | 125 | 0 | 0 | 0 | 59 | 29 | 0 | 0 | 79 | 67 |
| ♂ vas-Cas9/vas-Cas9 | 68 | 46 | 0 | 0 | 0 | 149 | 0 | 0 | 0 | 138 | 125 | 0 | 0 | 79 | 79 |
| ♂ vas-Cas9/vas-Cas9 | 72 | 71 | 0 | 0 | 0 | 54 | 0 | 0 | 0 | 171 | 160 | 0 | 0 | 270 | 145 |
| ♂ vas-Cas9/vas-Cas9 | 83 | 68 | 0 | 0 | 0 | 58 | 0 | 0 | 0 | 45 | 37 | 0 | 0 | 56 | 42 |
| ♂ vas-Cas9/vas-Cas9 | - | - | - | 0 | 0 | 115 | 0 | 0 | 0 | 110 | 102 | 0 | 0 | 89 | 72 |

Notes: At least ten females and ten males were set up for mating in each cross replicate, and their F1 progeny was scored and examined.

*100% sterility

** In some cases this is an underestimate due to difficulty to distinguish ♀ from ♂

FIG. 2F

Phenotype characteristics of trans-heterozygous flies carrying Cas9 and double gRNAs (dsRNA).

| Phenotype | $dgRNA^{βTub.\ Std}/+$; Cas9/+ | | $dgRNA^{βTub.\ Tra}/+$; Cas9/+ | | $dgRNA^{βTub.\ DsxF}/+$; Cas9/+ | |
|---|---|---|---|---|---|---|
| | ♂ | ♀ | ♂ | ♀ | ♂ | ♀ |
| Viability | viable | 100% lethal | viable | viable | viable | viable |
| External morphology | normal male | N/A | normal male | intersex | normal male | intersex |
| Fertility | 100% sterile | N/A | 100% sterile | 100% sterile | 100% sterile | 100% sterile |
| Ovaries | absent | N/A | absent | rudementary, variable | absent | developed or rudementary |
| Egg produced | N/A | N/A | N/A | few/rare | N/A | numerous, frequent |
| Egg laid | N/A | N/A | N/A | never | N/A | never |
| Testis | developed | N/A | developed | absent | developed | absent |
| Male accessory glands | developed | N/A | developed | developed | developed | developed |
| Sex combs | developed | N/A | developed | developed, variable | developed | absent |

Note: The phenotypic features other than lethality and sterility show variable manifestation independently of which Cas9 line (nos-Cas9, Ubi-Cas9, and vas-Cas9) was used or how Cas9 was inherited (maternal and paternal Cas9).

βTubulin 85D (βTub) target
CCTGAGTGTGCATCAGCTGG|TGG

The F1 progeny from the crosses between homozygous double gRNA/dgRNA and heterozygous Cas9 (Cas9/TM3, sb)

FIG. 4C

Competitiveness of dgRNAbTub,Sxl/+;nos-Cas9/+males

| Class # in Fig. 4 | genotype | laid eggs | unhatched eggs | hatched eggs | EggLaid % | hatching % |
|---|---|---|---|---|---|---|
| 2 | 2 wt ♂ | 131 | 6 | 125 | 65.83 | 95.42 |
| 2 | 2 wt ♂ | 60 | 18 | 42 | 30.15 | 70.00 |
| 2 | 2 wt ♂ | 141 | 10 | 131 | 70.85 | 92.91 |
| 2 | 2 wt ♂ | 146 | 5 | 141 | 73.37 | 96.58 |
| 2 | 2 wt ♂ | 89 | 26 | 63 | 44.72 | 70.79 |
| 1 | 1 wt ♂ | 124 | 6 | 118 | 62.31 | 95.16 |
| 1 | 1 wt ♂ | 129 | 24 | 105 | 64.82 | 81.40 |
| 1 | 1 wt ♂ | 127 | 18 | 109 | 63.82 | 85.83 |
| 1 | 1 wt ♂ | 104 | 5 | 99 | 52.26 | 95.19 |
| 1 | 1 wt ♂ | 165 | 32 | 133 | 82.91 | 80.61 |
| 3 | 1 wt ♂ & 1 bTub*, sxl* ♂ | 144 | 50 | 94 | 72.36 | 65.28 |
| 3 | 1 wt ♂ & 1 bTub*, sxl* ♂ | 108 | 71 | 37 | 54.27 | 34.26 |
| 3 | 1 wt ♂ & 1 bTub*, sxl* ♂ | 85 | 56 | 29 | 42.71 | 34.12 |
| 3 | 1 wt ♂ & 1 bTub*, sxl* ♂ | 72 | 31 | 41 | 36.18 | 56.94 |
| 3 | 1 wt ♂ & 1 bTub*, sxl* ♂ | 139 | 71 | 68 | 69.85 | 48.92 |
| 4 | 2 bTub*, Sxl* ♂ | 145 | 145 | 0 | 72.86 | 0.00 |
| 4 | 2 bTub*, Sxl* ♂ | 169 | 169 | 0 | 84.92 | 0.00 |
| 4 | 2 bTub*, Sxl* ♂ | 97 | 97 | 0 | 48.74 | 0.00 |
| 4 | 2 bTub*, Sxl* ♂ | 199 | 199 | 0 | 100.00 | 0.00 |
| 4 | 2 bTub*, Sxl* ♂ | 101 | 101 | 0 | 50.75 | 0.00 |

FIG. 4E

| replicate # | description of ♀ \ day# | 1 | 3 | 6 | 9 | 12 | 15 | 18 | 21 | 24 | 27 | 30 | 33 | 36 | 39 | 42 |
|---|---|---|---|---|---|---|---|---|---|---|---|---|---|---|---|---|
| 1 | ♀ control w- | 50 | 47 | 45 | 45 | 45 | 44 | 44 | 39 | 34 | 26 | 25 | 18 | 12 | 5 | 1 |
| 2 | ♀ control w- | 50 | 43 | 39 | 38 | 38 | 37 | 32 | 32 | 30 | 25 | 24 | 16 | 13 | 7 | 1 |
| 3 | ♀ control w- | 50 | 49 | 45 | 45 | 45 | 45 | 45 | 44 | 44 | 42 | 35 | 25 | 13 | 3 | 1 |
| 4 | ♀ control w- | 75 | 62 | 62 | 60 | 58 | 58 | 58 | 57 | 55 | 54 | 51 | 49 | 42 | 23 | 19 |
| 5 | ♀ control w- | 50 | 47 | 47 | 46 | 46 | 41 | 41 | 40 | 40 | 38 | 37 | 35 | 24 | 17 | 16 |
| 1 | ♀ dgRNA[bTub.Sxl]/+;nos-cas9{♂}/+ | 50 | 50 | 43 | 43 | 43 | 42 | 42 | 42 | 41 | 40 | 39 | 38 | 38 | 37 | 33 |
| 2 | ♀ dgRNA[bTub.Sxl]/+;nos-cas9{♂}/+ | 50 | 50 | 48 | 43 | 42 | 41 | 41 | 40 | 40 | 40 | 40 | 39 | 39 | 37 | 33 |
| 3 | ♀ dgRNA[bTub.Sxl]/+;nos-cas9{♂}/+ | 40 | 39 | 39 | 38 | 37 | 37 | 37 | 37 | 36 | 36 | 36 | 36 | 36 | 35 | 33 |
| 4 | ♀ dgRNA[bTub.Sxl]/+;nos-cas9{♂}/+ | 40 | 38 | 38 | 37 | 37 | 35 | 35 | 34 | 33 | 33 | 33 | 33 | 31 | 29 | 27 |
| 5 | ♀ dgRNA[bTub.Sxl]/+;nos-cas9{♂}/+ | 40 | 40 | 39 | 39 | 38 | 37 | 37 | 37 | 37 | 36 | 35 | 35 | 32 | 32 | 30 |
| 1 | ♀ dgRNA[bTub.Sxl]/+;nos-cas9{♀}/+ | 50 | 45 | 43 | 42 | 42 | 42 | 42 | 41 | 41 | 41 | 41 | 40 | 38 | 38 | 38 |
| 2 | ♀ dgRNA[bTub.Sxl]/+;nos-cas9{♀}/+ | 50 | 50 | 50 | 50 | 50 | 48 | 47 | 46 | 46 | 46 | 41 | 46 | 43 | 42 | 41 |
| 3 | ♀ dgRNA[bTub.Sxl]/+;nos-cas9{♀}/+ | 50 | 49 | 49 | 48 | 48 | 47 | 47 | 47 | 46 | 45 | 41 | 38 | 38 | 37 | 36 |
| 4 | ♀ dgRNA[bTub.Sxl]/+;nos-cas9{♀}/+ | 75 | 73 | 72 | 72 | 72 | 71 | 70 | 69 | 68 | 68 | 66 | 65 | 64 | 59 | 56 |
| 5 | ♀ dgRNA[bTub.Sxl]/+;nos-cas9{♀}/+ | 50 | 49 | 49 | 49 | 48 | 48 | 48 | 46 | 46 | 45 | 45 | 45 | 43 | 42 | 39 |

FIG. 4F

| Strategy | Parameter | Value | Reference |
|---|---|---|---|
| General | Egg production per female (day⁻¹) | 20 | Otero et al., Bull. Math. Biol. 68, 1945–1974 (2006). |
| | Duration of egg stage (days) | 5 | Christophers et al., 1960–please provide full citation |
| | Duration of larval stage (days) | 6 | Christophers et al., 1960 (*supra*). |
| | Duration of pupal stage (days) | 4 | Christophers et al., 1960 (*supra*). |
| | Daily population growth rate (day⁻¹) | 1 175 | Simoy et al., 2015-please provide full citation |
| | Daily mortality risk of adult stage (day⁻¹) | 0.090 | Focks et al., J. Med. Entomol., 30:1018-1028, (1993), Focks et al., J. Med. Entomol., 30:1003-1017, (1993); Horsfall, J. Econ. Entomol, 65:891-892, (1972); and Fay 1964- please provide full citation |
| | Adult female population size | 10,000 | Carvalho et al., PLoS Negl. Trop. Dis. 9, e0003864 (2015). |
| IIT | Reduction in adult male lifespan | 0.50 | Yamada et al., J. Med. Entomol. 51, 811–816 (2014); Zhang et al., PLoS One 10, e0121126 (2015)[1]; and Zhang et al., PLoS One 10, e0135194 (2015)[2]. |
| | Male mating competitiveness | 1.00 | Bellini et al., J. Med. Entomol., 50:94-102, (2013); and Atyame et al., PLoS One, e0146834, doi:10.1371/journal.pone.0146834, (2016). |
| RIDL/fsRIDL | Reduction in adult male lifespan | 0.18 | Massonnet-Bruneel et al., PLoS One, e62711, (2013). |
| | Male mating competitiveness | 0.05 | Carvalho et al., PLoS Negl. Trop. Dis. 9, e0003864 (2015); Harris et al., Nat. Biotechnol. 29, 1034–1037 (2011). |
| pgSIT | Reduction in adult male lifespan | 0.18 | Massonnet-Bruneel et al., (2013) (*supra*). |
| | Male mating competitiveness | 0.78 | FIG. 4B |

ENDONUCLEASE SEXING AND STERILIZATION IN INSECTS

CROSS-REFERENCE TO RELATED APPLICATION

The present application claims priority to and the benefit of U.S. Provisional Application Ser. No. 62/589,405 filed on Nov. 21, 2017, entitled "NOVEL STERILE INSECT TECHNIQUE," the entire content of which is incorporated herein by reference.

STATEMENT REGARDING FEDERALLY SPONSORED RESEARCH OR DEVELOPMENT

This invention was made with government support under Grant No(s). 5K22AI113060 and 1R21AI123937 awarded by the National Institutes of Health and Grant No: HR0011-17-2-0047 awarded by the Defense Advanced Research Project Agency. The government has certain rights in the invention.

BACKGROUND

Mass-production and release of sterile males, known as the Sterile Insect Technique (SIT), has historically been used to control, and eradicate, insect pest populations dating back to the mid-1930s. Previous methodologies have relied on DNA-damaging agents for sterilization, substantially reducing overall fitness and mating competitiveness of released males. To overcome these issues, microbe-mediated infertility techniques such as *Wolbachia*-based incompatible insect technique (IIT) and modern genetic SIT-like systems such as the Release of Insects carrying a Dominant Lethal (RIDL), and other methodologies to release fertile males that genetically kill females such as female-specific RIDL (fsRIDL), and autosomal-linked X-chromosome shredders have been developed. While these first-generation genetic SIT technologies represent significant advances, IIT strictly requires no infected females to be released which is difficult to achieve in the field, and the use of tetracycline known to ablate the microbiota compromises the fitness of RIDL/fsRIDL males, and X-chromosome shredders can in principle only be developed in species with heterogametic sex chromosomes, thereby limiting wide applicability to other species. Therefore, it would be logistically advantageous to employ more efficient SIT-based technologies that can be deployed as eggs by which only sterile males would survive.

SUMMARY

Aspects of embodiments of the present disclosure are directed to methods including precision guided sterile insect technique (pgSIT).

In some embodiments of the present disclosure, a method of directing male sexing in a genetically modified insect includes: integrating at least one nucleic acid sequence into a genome of a first insect, the at least one nucleic acid sequence having at least one first guide polynucleotide targeting a female-essential genomic sequence that is required for female-specific viability; introducing an endonuclease into a second insect, the second insect capable of being genetically crossed with the first insect; and genetically crossing the first insect and the second insect thereby producing progeny expressing the endonuclease and the at least one nucleic acid sequence from which male insect eggs mature to adulthood.

In some embodiments of the present disclosure, a method of producing a progeny of genetically modified sterile male insect eggs includes: integrating at least one nucleic acid sequence into a genome of a first insect, the at least one nucleic acid sequence having at least one first guide polynucleotide targeting a female-essential genomic sequence that is required for female-specific viability; introducing an endonuclease into a second insect, the second insect capable of being genetically crossed with the first insect, wherein the at least one nucleic acid sequence further includes at least one second guide polynucleotide targeting a male sterility genomic sequence that is required for male-specific sterility; and genetically crossing the first insect and the second insect to produce a progeny of genetically modified sterile male insect eggs.

In some embodiments of the present disclosure, the integrating at least one nucleic acid sequence into the genome of the first insect includes homozygous integration into all chromosome copies in the genome. In some embodiments, the integrating the at least one nucleic acid sequence includes introducing the at least one nucleic acid sequence into the first insect during an embryonic stage.

In some embodiments of the present disclosure, the at least one first guide polynucleotide and the at least one second guide polynucleotide each include at least one guide ribonucleic acid (gRNA).

In some embodiments of the present disclosure, the female-essential genomic sequence includes a gene essential for female-specific viability or a female-specific exon essential for female-specific development and/or female-specific viability.

In some embodiments of the present disclosure, the at least one first guide polynucleotide includes more than one first guide polynucleotide each of which targets a different region of the same female-essential genomic sequence that is required for female-specific viability.

In some embodiments of the present disclosure, the at least one first guide polynucleotide includes more than one first guide polynucleotide each of which targets a different female-essential genomic sequence that is required for female-specific viability.

In some embodiments of the present disclosure, the female-essential genomic sequence is a gene or a splice-variant of a gene, the gene selected from the group of sex lethal (Sxl), transformer (Tra), doublesex (Dsx), homologs thereof, orthologs thereof, paralogs thereof, or combinations thereof.

In some embodiments of the present disclosure, the at least one first guide polynucleotide includes more than one first guide polynucleotide each of which targets a different gene selected from Sxl, Tra, or Dsx including homologs thereof, orthologs thereof, or paralogs thereof.

In some embodiments of the present disclosure, the more than one first guide polynucleotide includes two first guide polynucleotides each of which targets a different gene selected from Sxl, Tra, or Dsx including homologs thereof, orthologs thereof or paralogs thereof.

In some embodiments of the present disclosure, the more than one first guide polynucleotide includes two first guide polynucleotides each of which targets a different gene selected from Sxl or Dsx including homologs thereof, orthologs thereof or paralogs thereof.

In some embodiments of the present disclosure, the male sterility genomic sequence is a gene selected from βTubulin 85D (βTub), fuzzy onions (Fzo), protamine A (ProtA), or spermatocyte arrest (Sa) including homologs thereof, orthologs thereof or paralogs thereof.

In some embodiments of the present disclosure, when the second insect is a male, the introducing the endonuclease into the second insect includes homozygously integrating a gene encoding the endonuclease, and when the second insect is a female, the introducing the endonuclease into the second insect includes homozygously or heterozygously integrating a gene encoding the endonuclease or depositing an endonuclease protein into the second insect.

In some embodiments of the present disclosure, introducing an endonuclease into a second insect includes introducing the endonuclease into the second insect during an embryonic stage.

In some embodiments of the present disclosure, a progeny of genetically modified insect eggs include up to 100% male insect eggs produced according to the methods of the present disclosure.

In some embodiments of the present disclosure, a progeny of genetically modified insect eggs include up to 100% sterile male insect eggs produced according to the methods of the present disclosure.

In some embodiments, a genetically modified sterile male insect produced according to the methods of the present disclosure is capable of increasing the rate of unhatched eggs by mating with wild-type female insects.

In some embodiments of the present disclosure, a method of reducing a wild-type insect population includes introducing a genetically modified sterile male produced according to the methods of the present disclosure into the wild-type insect population.

Figure 1A:
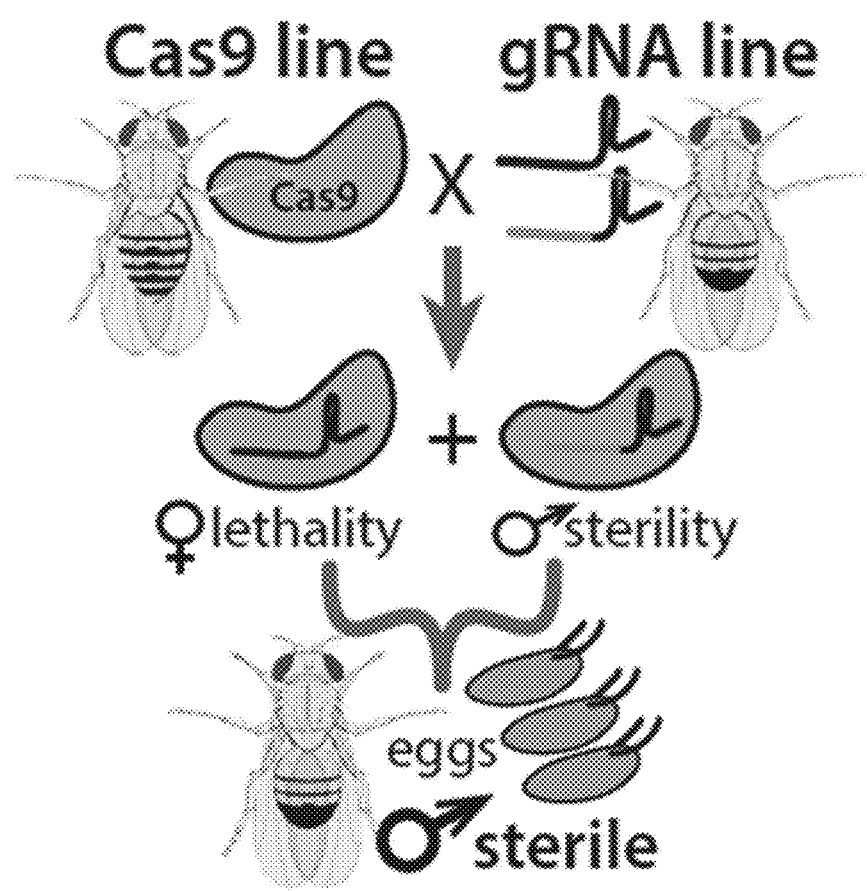
FIG. 1A is a schematic of pgSIT utilizing two components of the binary CRISPR/Cas9 system, the endonuclease Cas9 and guide ribonucleic acids (gRNAs) (with blue or green target-specific sequences), maintained as separated homozygous lines, their cross results in concurrent or simultaneous knockouts of a gene required for female viability and a gene required for male sterility resulting in survival of only $F_1$ sterile males, according to embodiments of the present disclosure.

FIG. 1E shows bar graphs of average gender frequencies in $F_1$ progeny of crosses with the engineered parental insects according to embodiments of the present disclosure. Two top panels depict gender frequencies from bidirectional control crosses of homozygous sgRNA lines to wild type (wt) indicating that both fertile females and males (♀ and ♂) are present at similar ratios, but no sterile intersexes (□) were identified. The fertile females are shown in pink, fertile males are shown in blue, sterile females in orange, and sterile males in grey. The bottom two panels show gender frequencies from crosses of homozygous nanos-Cas9 (nos-Cas9) to wt (control) and four homozygous sgRNA lines (experiment). Independent of maternal or paternal Cas9 inheritance, 100% of trans-heterozygous sgRNA$^{Sxl}$ ♀ were lethal, 100% of trans-heterozygous sgRNA$^{Tra}$ and sgR-NA$^{DsxF}$ ♀ were masculinized into sterile intersexes □, and 100% of trans-heterozygous sgRNA$^{\beta Tu}$ ♂ were sterile. Gender frequencies and fertility in trans-heterozygotes were compared to those in corresponding progeny of control crosses with nos-Cas9 (solid lines) or sgRNAs (dashed lines) and wt flies. Each bar shows an average gender frequency and one standard deviation. Statistical significance was calculated with t tests assuming unequal variance, and for male sterilization, P values were calculated using Pearson's Chi-squared test for contingency tables (red*). (P>0.001***).

FIG. 1F is a table of the $F_1$ progeny from the crosses between homozygous single gRNA (sgRNA/sgRNA) and homozygous nos-Cas9 (nos-Cas9/nos-Cas9), according to embodiments of the present disclosure.

FIG. 1G is a table of Genotyping genomic loci targeted by gRNAs using methods according to embodiments of the present disclosure, where (insertions/deletions) indels (red text) were found in transheterozygous flies.

Figure 1B:
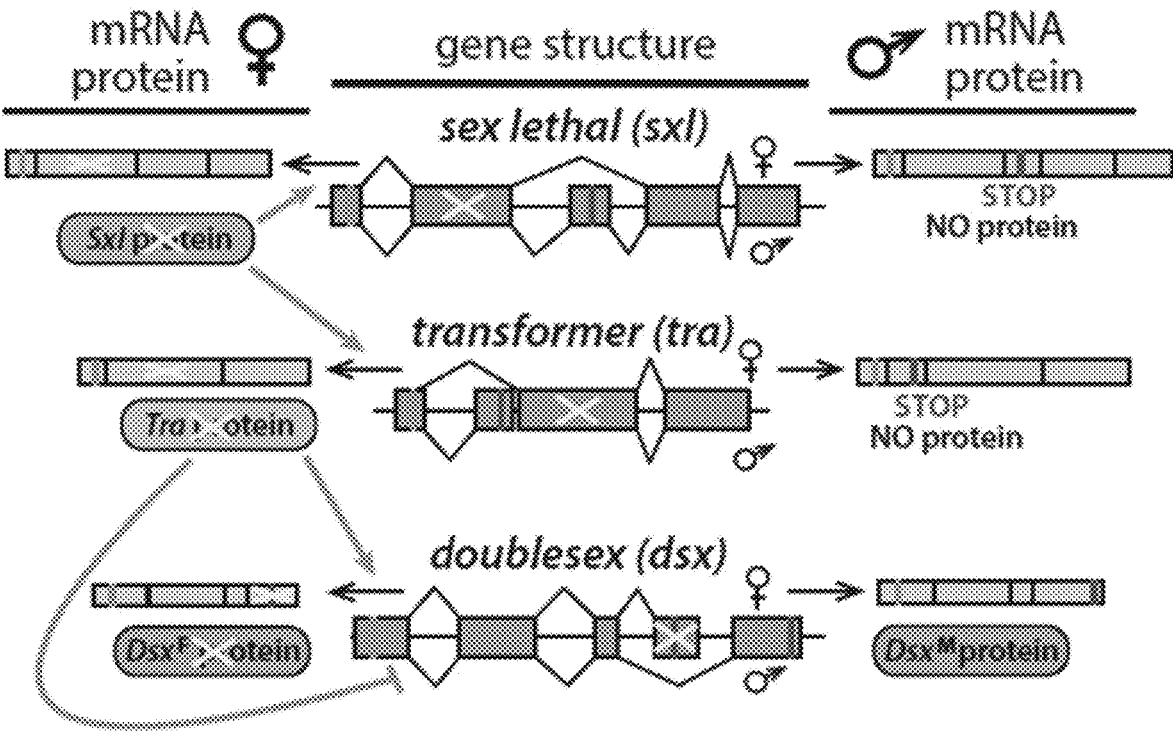
FIG. 1B is a schematic of sex specific alternative splicing in the sxl, tra and dsx genes regulated by female expression of Sxl (green) and Tra (yellow) proteins (gray lines); disruption of female-specific exons of key sex-determination genes, sxl, tra and dsx, disrupts female development; and the pgSIT exon targets are indicated by yellow crosses, according to embodiments of the present disclosure.
Figure 1C:
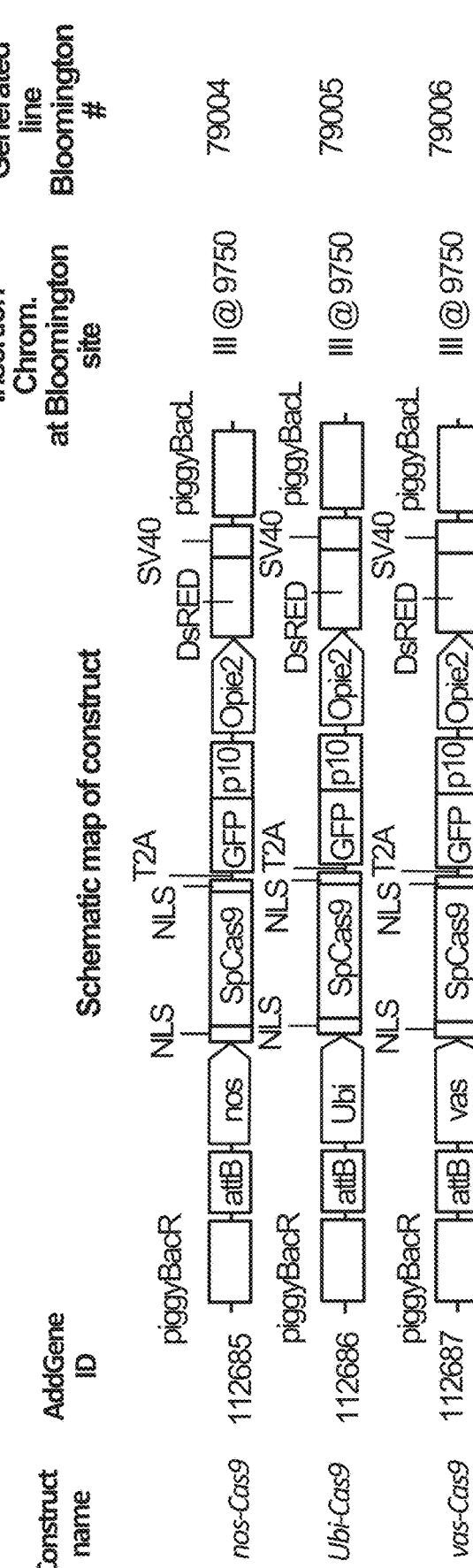
FIG. 1C presents schematics of all constructs engineered according to embodiments of the present disclosure, with functional constructs and flies deposited to Addgene.org and Bloomington *Drosophila* Stock Center, respectively. Gene names and gRNA target site sequences are presented in the box. The coding sequence of a SpCas9 was flanked by two nuclear localization signals (NLS) at both ends and a self-cleaving T2A peptide with eGFP coding sequence at the C-end, serving as a visual indicator of Cas9 expression.
Figure 1C:
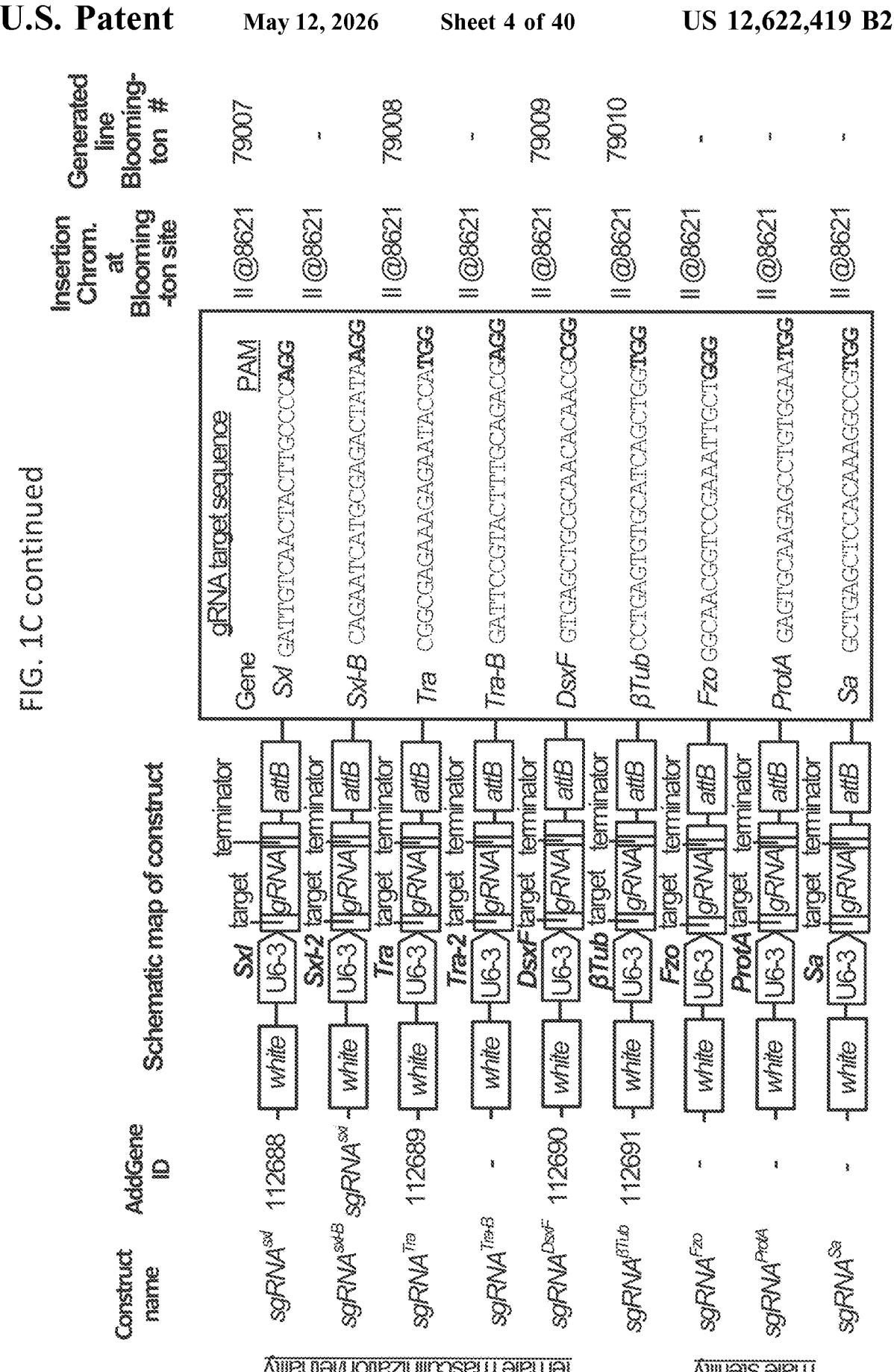
Figure 1C:
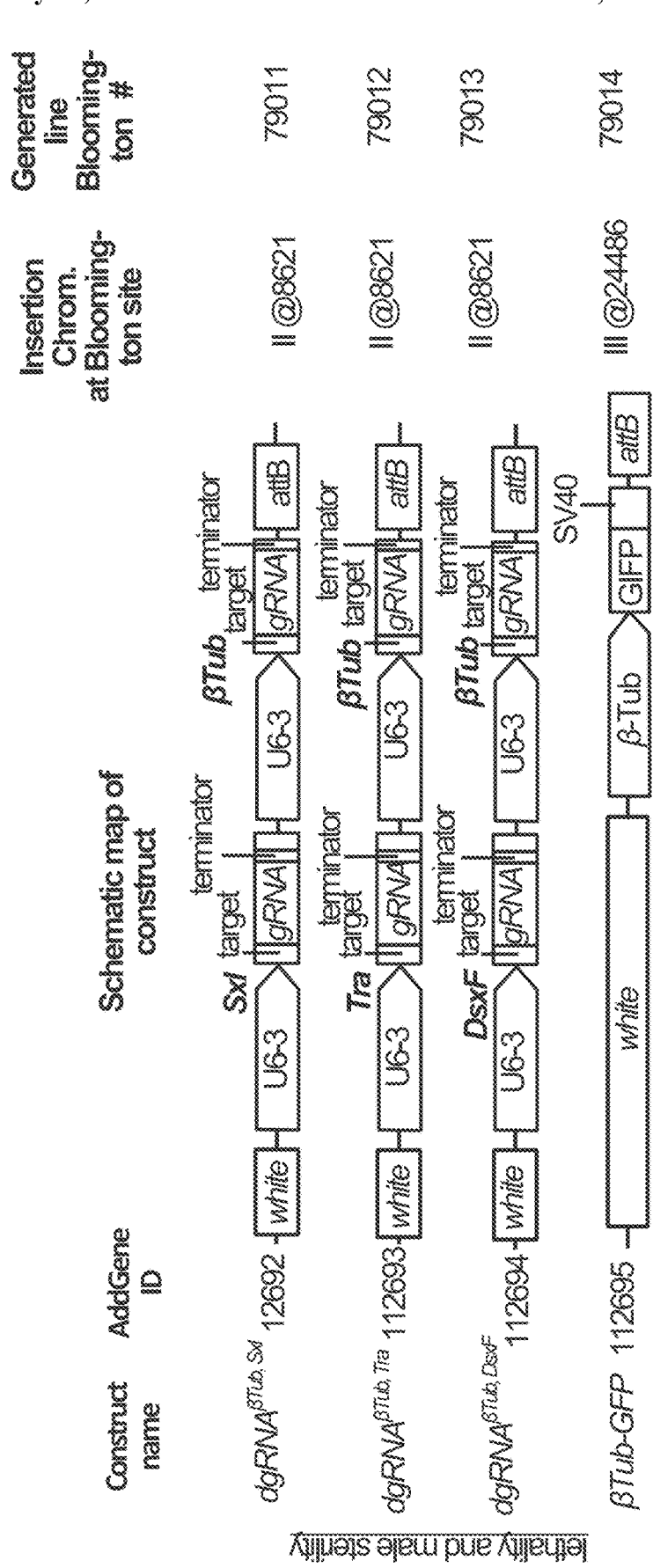
Figure 1D:
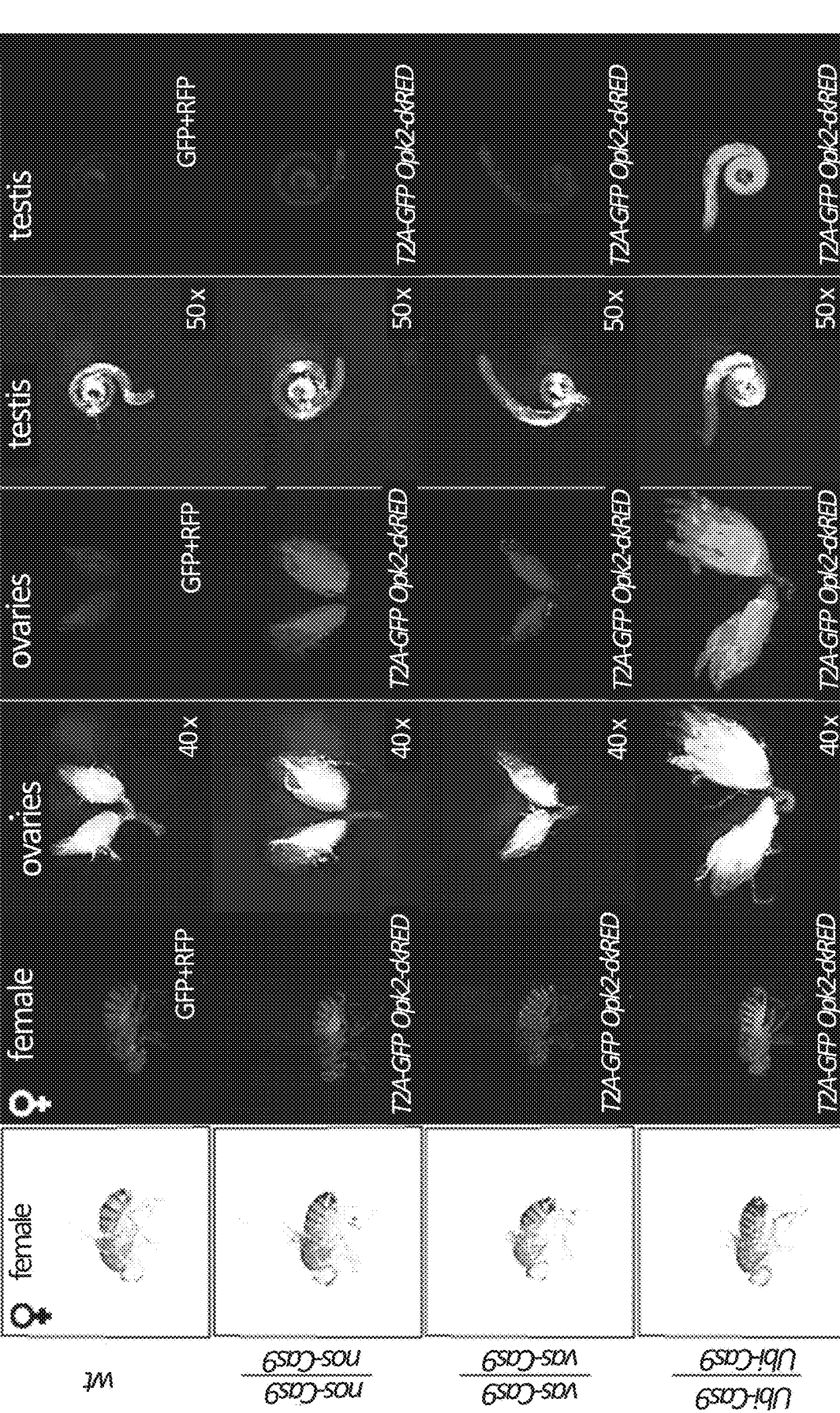
FIG. 1D are fluorescent stereo microscope images of three new homozygous lines expressing *Streptococcus pyogenes* Cas9 (SpCas9) engineered according to embodiments of the present disclosure. Three *Drosophila* lines supporting expression of SpCas9 in strictly germ line or germ line together with somatic cells were developed. Nanos-Cas9 (nos-Cas9), vasa-Cas9 (vas-Cas9), and Ubiquitin-63E (Ubi-Cas9) were inserted at the same site on the 3rd chromosome using φC31-mediated integration. Opie2-dsRed transgene served as a transgenesis marker and a self-cleaving T2A- eGFP sequence, which was attached to the 3'-end of SpCas9 coding sequence, provided an indicator of Cas9 expression as shown in FIG. 1C. Expression levels of dsRed and eGFP in each Cas9 line were compared to wild type (wt) flies. The Cas9-T2A-eGFP expression was mostly limited to female germ line in nos-Cas9 and vas-Cas9 with a strong expression in nos-Cas9. Ubi-Cas9 supported the strongest expression of Cas9, measured by eGFP, in both female and male germline, and in soma.
Figure 1E:
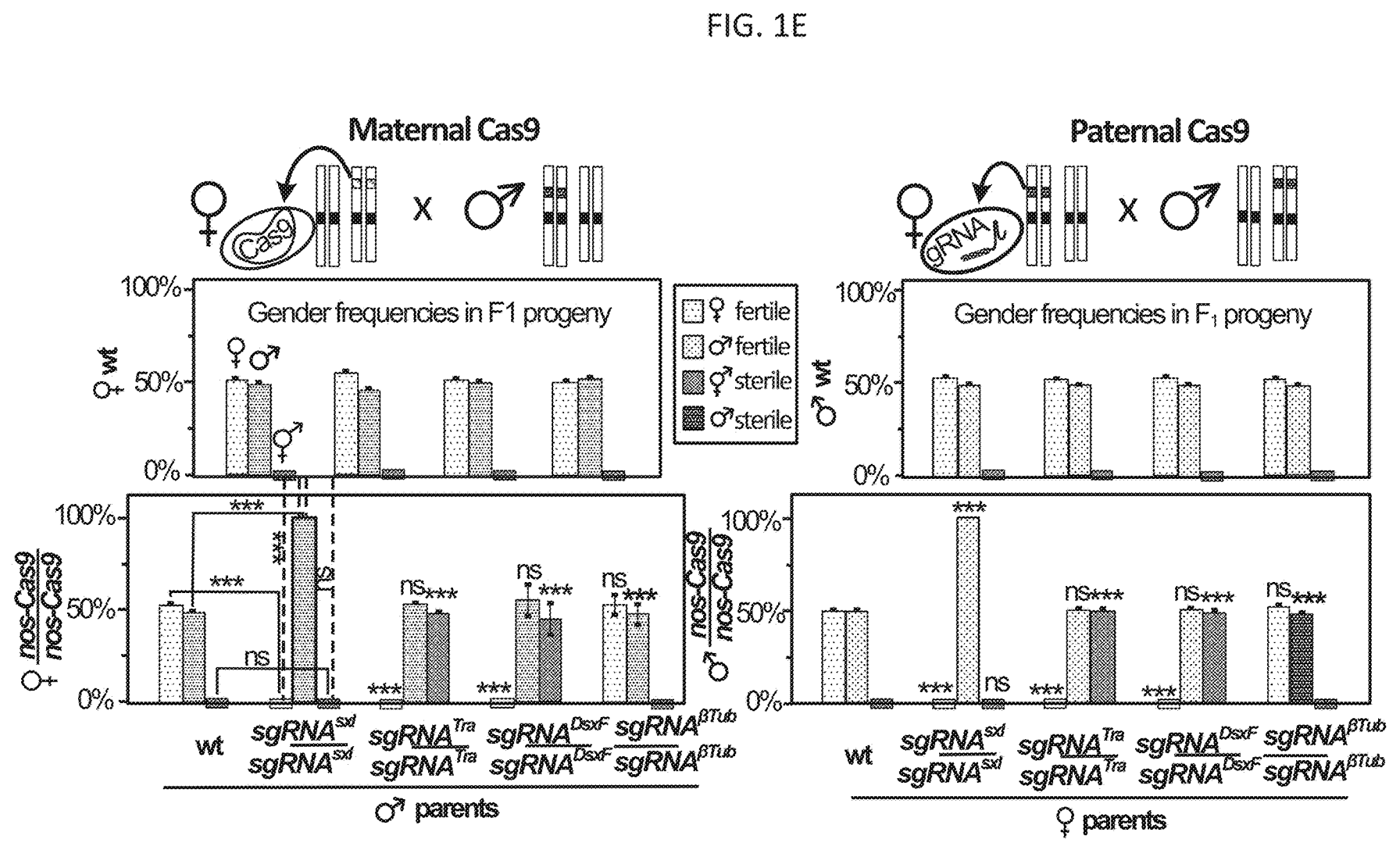
Figure 2A:
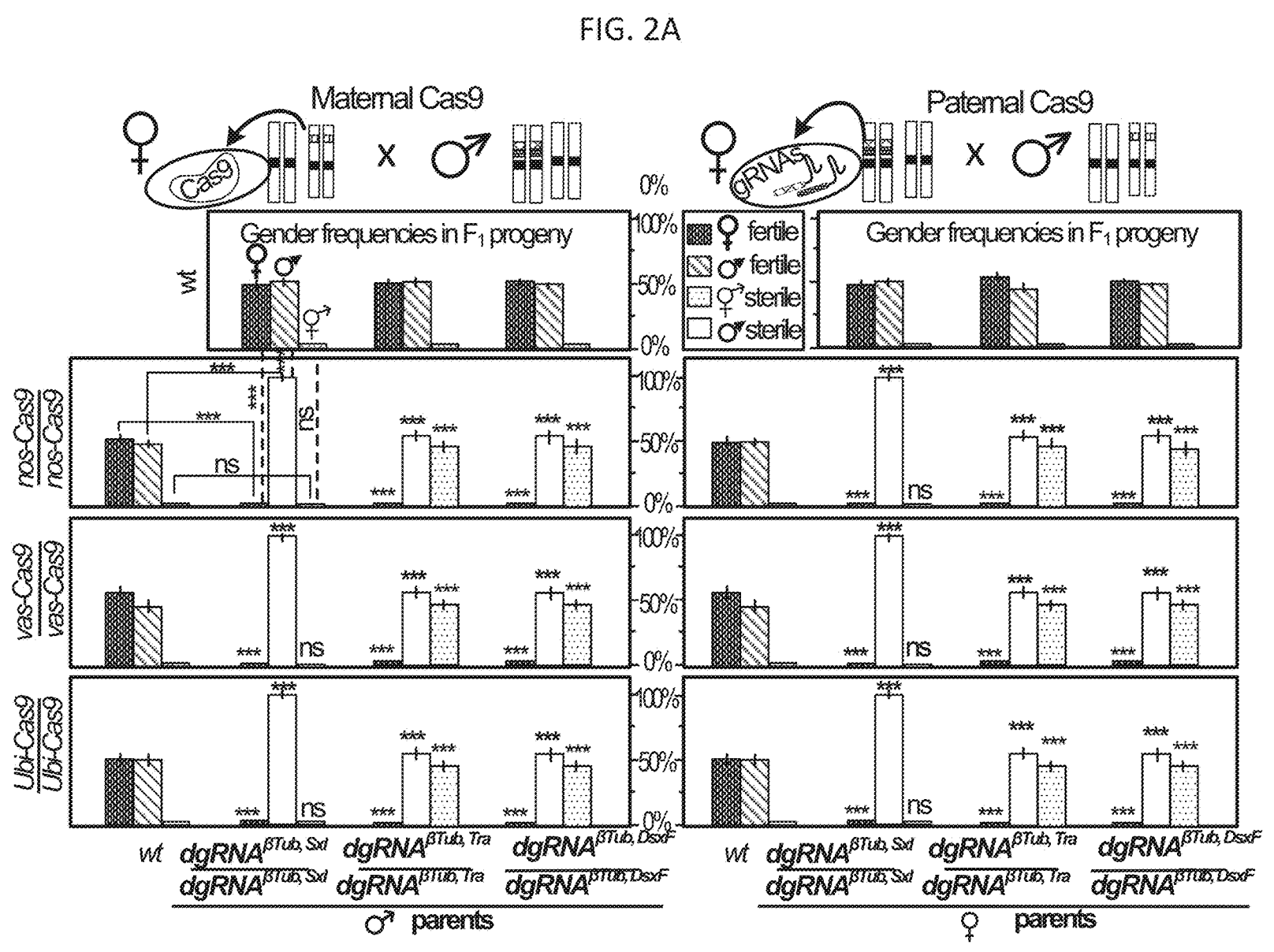

FIG. 2A shows bar graphs of Gender (♀ (female), ♂ (male), and □ intersex) frequencies of trans-heterozygous $F_1$ progeny resulting from crosses between double gRNAs (dsRNA) and Cas9 homozygous lines according to embodiments of the present disclosure. Three double guide RNAs (dgRNAs), each targeting sxl, tra or dsx combined with βTub, were bidirectionally crossed with three Cas9 lines driven by nanos (nos), vasa (vas), and Ubiquitin-63E (Ubi) promoters and were sufficient to ensure complete penetrance of both female lethality/masculinization and male sterility in each reciprocal cross as indicated in FIGS. 1C-1D. Gender frequencies and fertility in trans-heterozygotes were compared to those in corresponding progeny of control crosses with Cas9 (bar groups to the left, solid lines) or dgRNAs (top panels, dashed lines) and wt flies. Each bar shows an average gender frequency and one standard deviation. Statistical significance was calculated with t tests assuming unequal variance, and for male sterilization, P values were calculated using Pearson's Chi-squared test for contingency tables (red *). (P>0.01, P>0.001*).

FIG. 2B is a table of the $F_1$ progeny from the crosses between homozygous double gRNA (sgRNA/dgRNA) and homozygous Cas9 (Cas9/Cas9) lines, according to embodiments of the present disclosure.

Figure 2C:
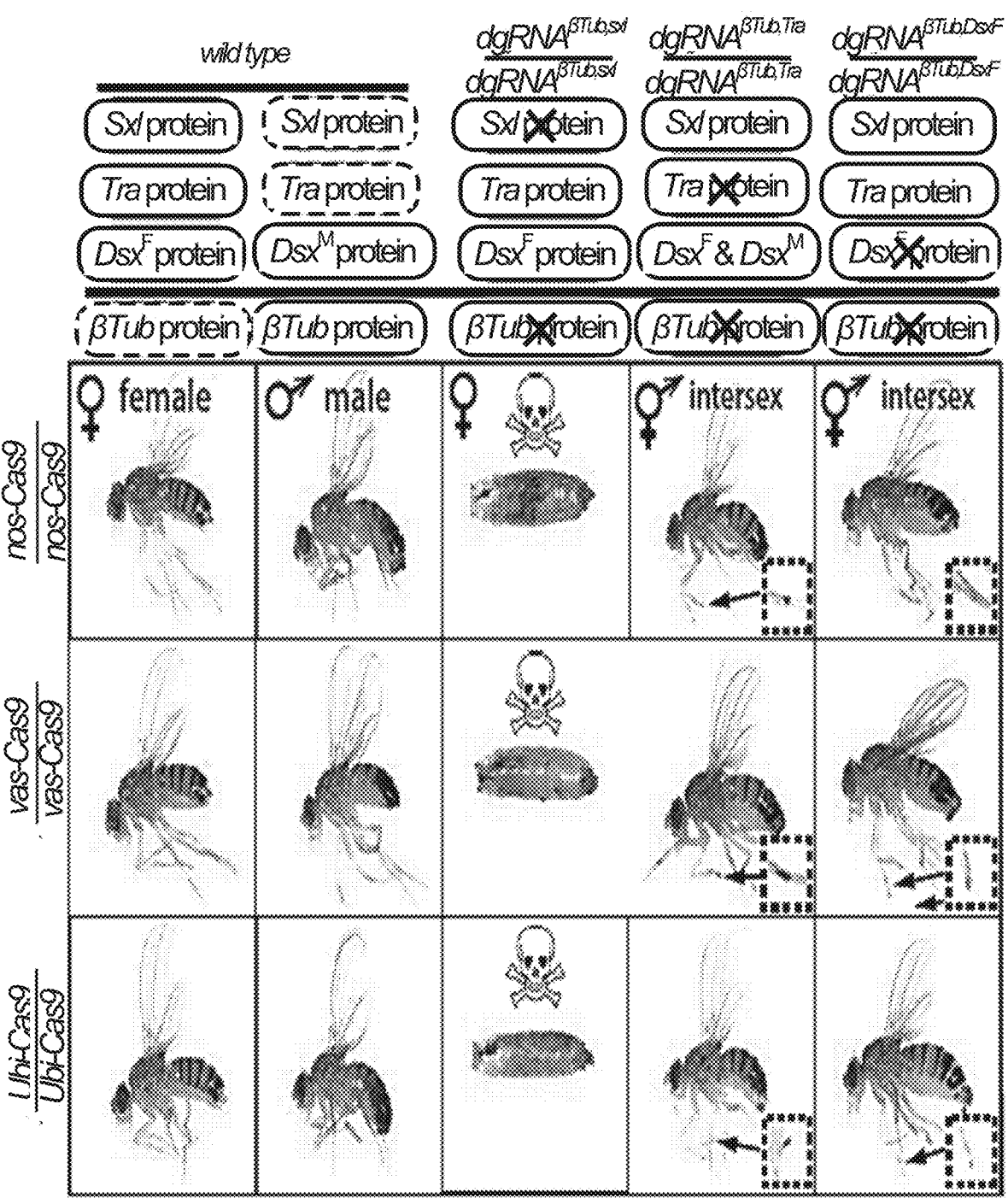
Figure 2D:
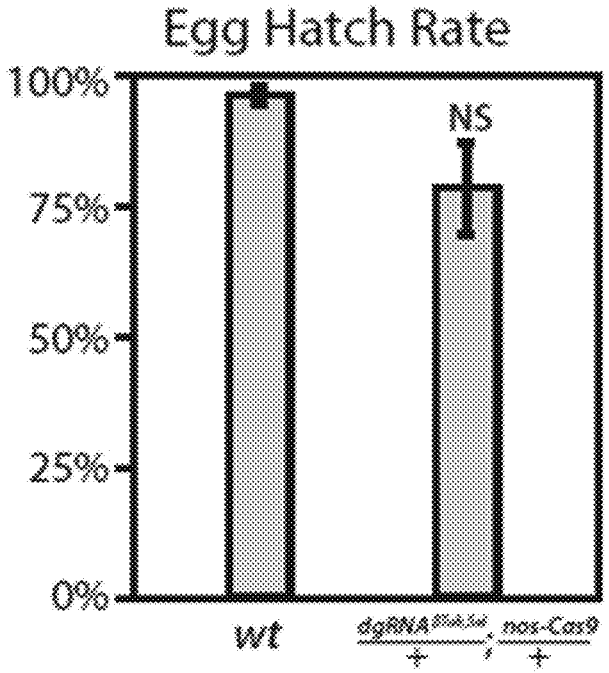
Figure 2E:
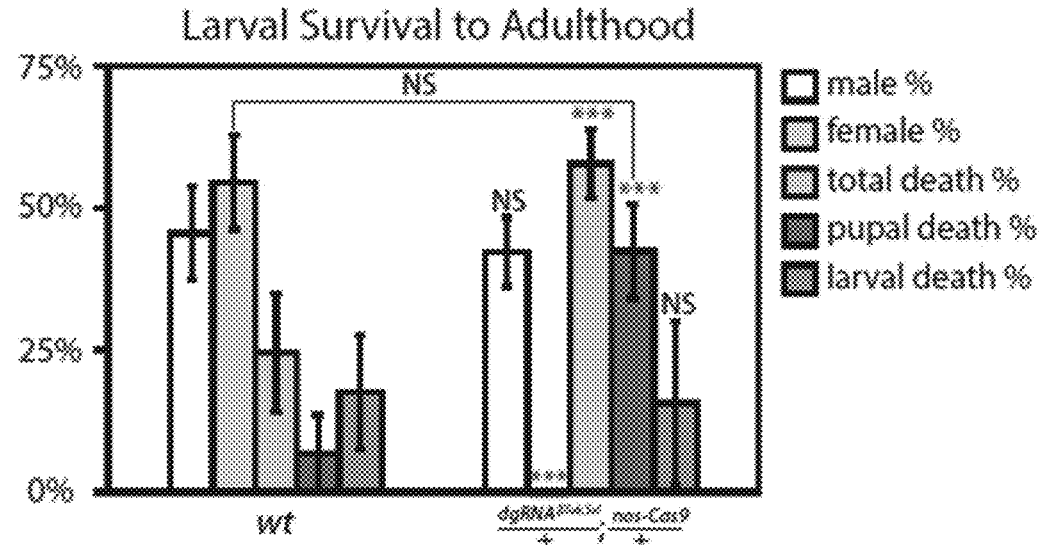

FIG. 2C is a data table showing the order of targeted gene in sex-determination pathway (top) and corresponding knockout phenotype (with images) in progeny according to embodiments of the present disclosure. Phenotypes of dgR-NAs directed-knockouts and intersex morphology in comparison to wt ♀ and §. βTub, Sxl knockouts ♀ perish during pupal stages as indicated in FIGS. 2D-2E. As shown, dgRNA$^{\beta Tub,Tra}$/+; nos-Cas9/+ intersexes (♀), but not dgRNA$^{\beta Tub,DsxF}$/+; nos-Cas9/+ ♀, had sex combs—see magnified inside inserts.

FIG. 2D shows bar graphs showing that the hatching rate (percentage) estimated for dgRNA$^{\beta Tub,Sxl}$/+; nos-Cas9/+ eggs generated by crossing homozygous nos-Cas9/nos-Cas9 ♀ and dgRNA$^{\beta Tub,Sxl}$/dgRNA$^{\beta Tub,Sxl}$ § was not statistically different from that of the wild type (wt) eggs as indicated in Example 6, according to embodiments of the present disclosure. Statistical significance was calculated with a t test assuming unequal variance. (P<0.05$^{NS}$, P>0.001***).

FIG. 2E shows bar graphs showing the rates of different outcomes for hatched dgRNA$^{\beta Tub,Sxl}$/+; nos-Cas9/+ larvae, according to embodiments of the present disclosure, for which batches of 50 hatched larvae were raised to adults, their gender or developmental time of death was recorded as indicated in Example 6. The majority of additional larval deaths happened during a pupal transition, and the percentage of pupal death was not statistically different from the wt ♀ percentage. Statistical significance was calculated with a t test assuming unequal variance. (P<0.05$^{NS}$, P>0.001***).

FIG. 2F is a table of the phenotypic characteristics of trans-heterozygous flies carrying Cas9 and double gRNAs (dsRNA), according to embodiments of the present disclosure.

Figure 2G:
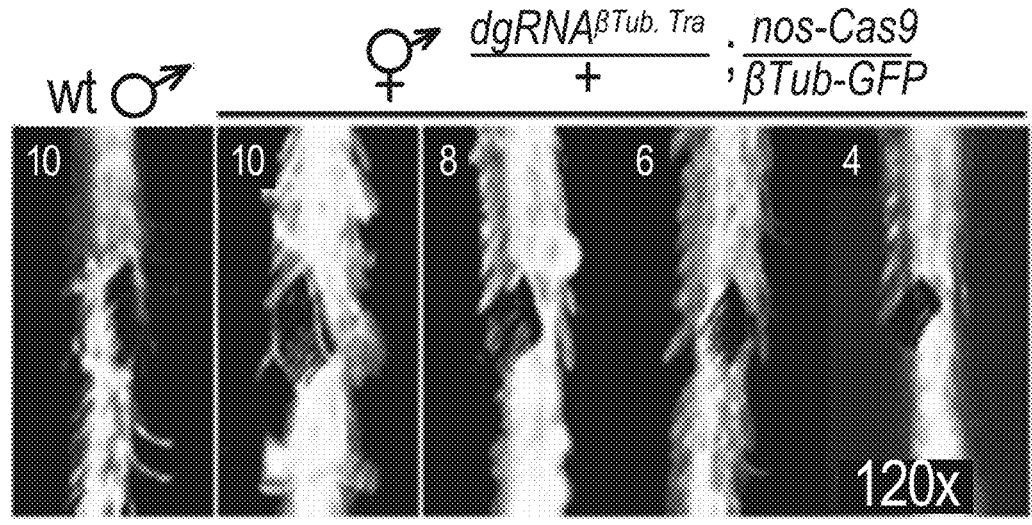

FIG. 2G shows microscope images of variable expressivity of the number of sex comb bristles in βTub, Tra knockouts □, according to embodiments of the present disclosure.

Figure 2H:
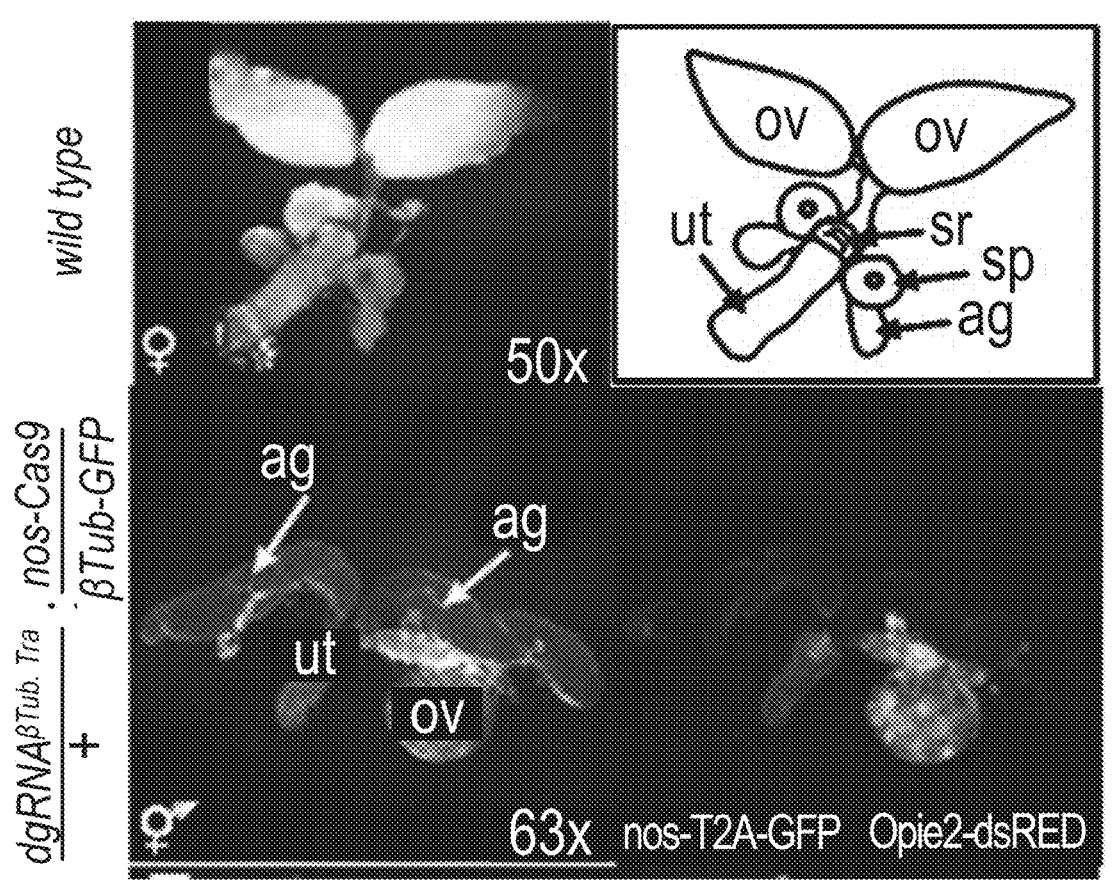

FIG. 2H shows microscope images of internal reproductive organs in wt females (upper image): two ovaries (ov), seminal receptacle (sr), double spermatheca (sp), two accessory glands (ag), and uterus (ut), and the dgRNA$^{\beta Tub,Tra}$/+; nos-Cas9/+ □ intersex fly (lower image) had one rudimentary ovary, and organs that resembled male accessory glands, according to embodiments of the present disclosure.

Figure 2I:
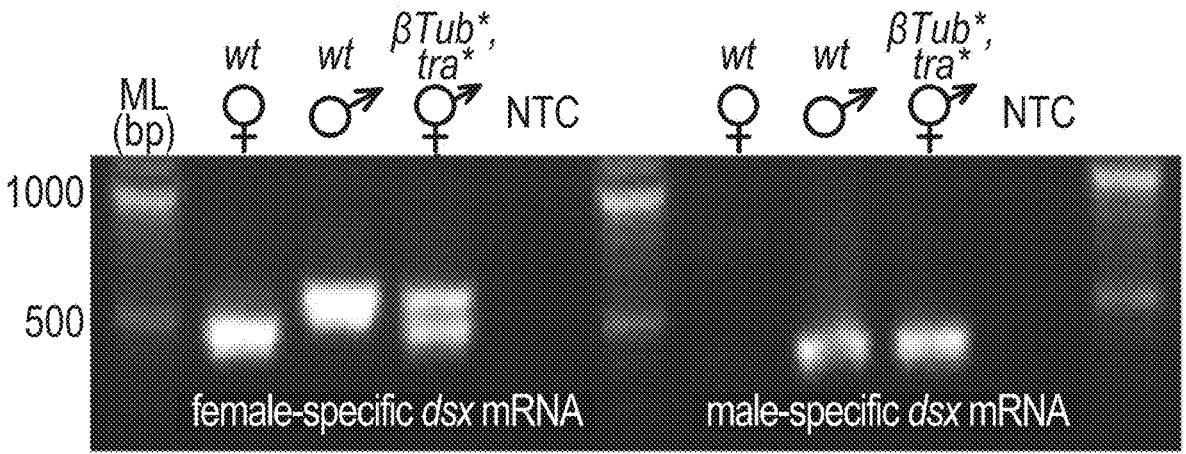

FIG. 2I is an agarose gel image of amplified transcripts indicating that both male and female splice variants of the Dsx gene are expressed in βTub, Tra knockout intersexes, according to embodiments of the present disclosure. RT-PCR was used to assess female-specific and male-specific alternative splice variants of dsx comparing wild type (wt) females (♀), wt males (♂) and dgRNA$^{\beta Tub,Tra}$/+; nos-Cas9/+ intersexes (βTub*, Tra*□). Both female and male-specific dsx transcripts were identified in βTub*, Tra*□. Molecular ladder (ML) of double stranded DNA and No template control (NTC) are indicated.

Figure 2J:
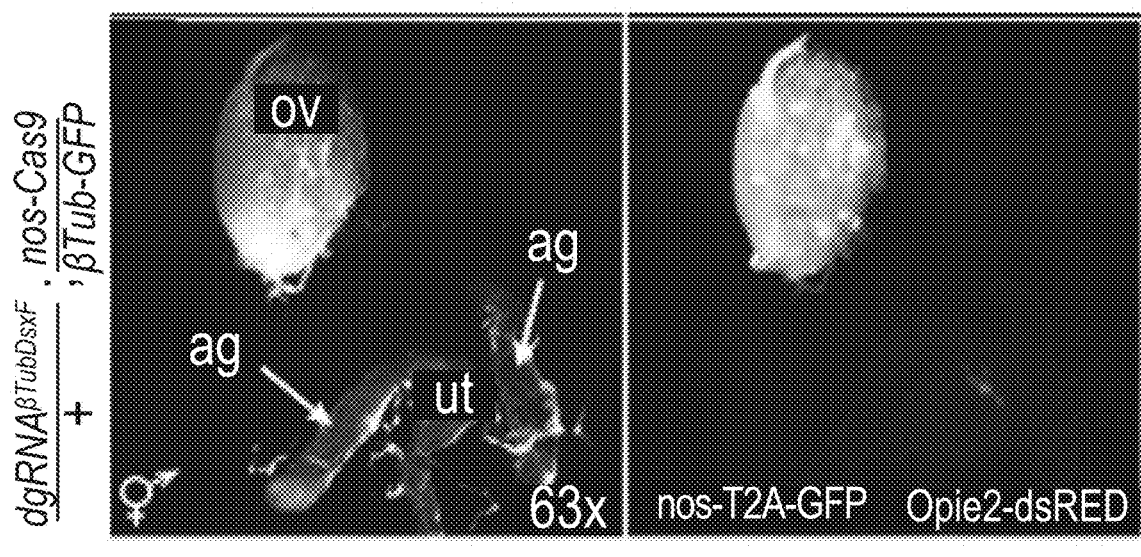

FIG. 2J shows microscope images of dgRNA$^{\beta Tub,DsxF}$/+, nos-Cas9/+ □ intersex flies have developed only a single ovary (ov) often times not connected with an oviduct and organs that resembled male-specific accessory glands (ag) as indicated, according to embodiments of the present disclosure.

Figure 2K:
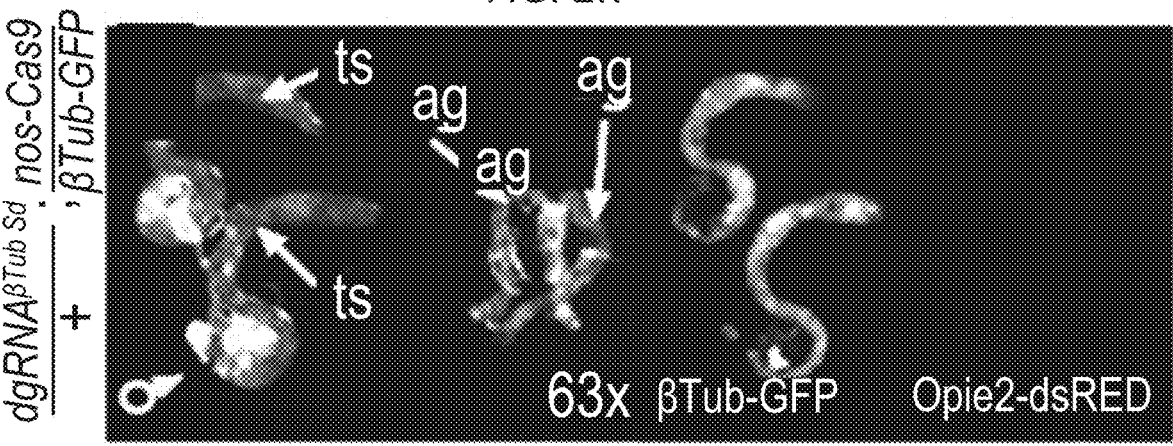

FIG. 2K shows microscope images of male internal reproductive system in dgRNA$^{\beta Tub,Sxl}$/+; nos-Cas9/+ ♂ flies with testis (ts) and adrenal glands (ag) as indicated, according to embodiments of the present disclosure.

Figure 2L:
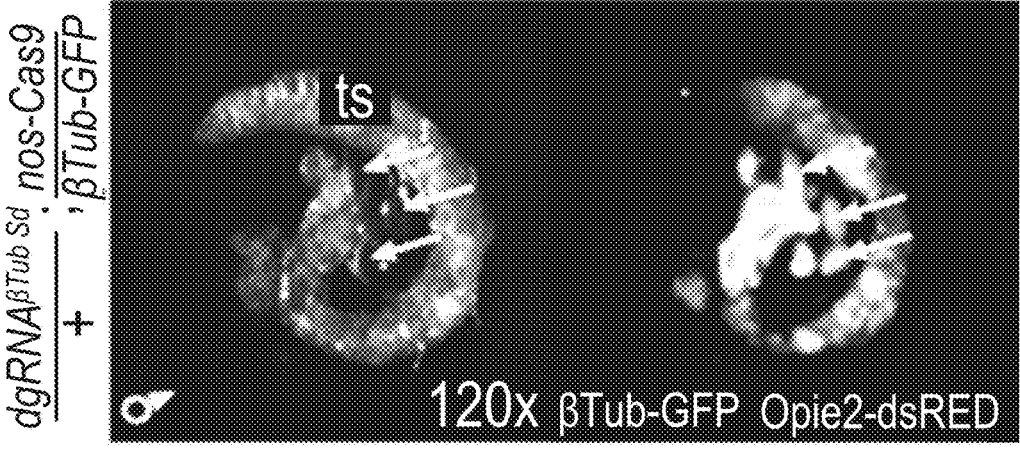

FIG. 2L shows microscope images of male internal reproductive system in dgRNA$^{\beta Tub,Sxl}$/+; nos-Cas9/+ ♂ flies with testis (ts) and adrenal glands (ag) as indicated, according to embodiments of the present disclosure.

Figure 2M:
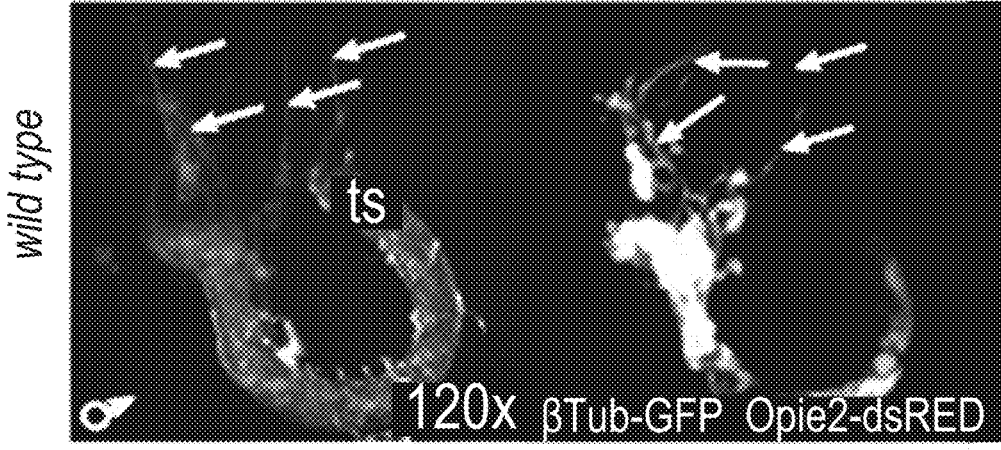

FIG. 2M shows microscope images of wild type wt testis (left image) having, elongated cysts with maturing spermatids which were not found in the dgRNA$^{\beta Tub,Sxl}$/+; nos-Cas9/+ testis (ts) as indicated here and in FIGS. 2K-2L, according to embodiments of the present disclosure.

Figure 2N:
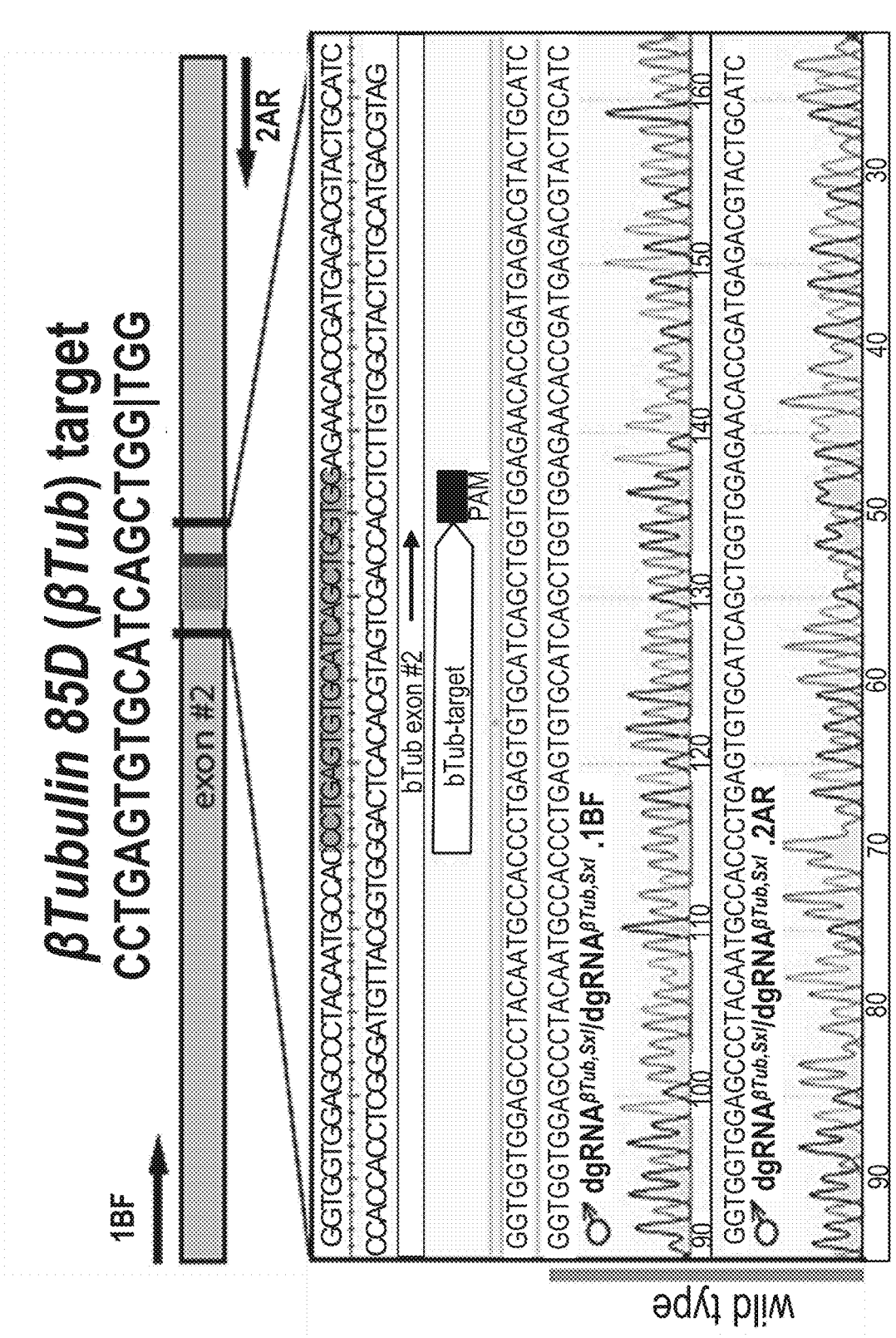
Figure 2N:
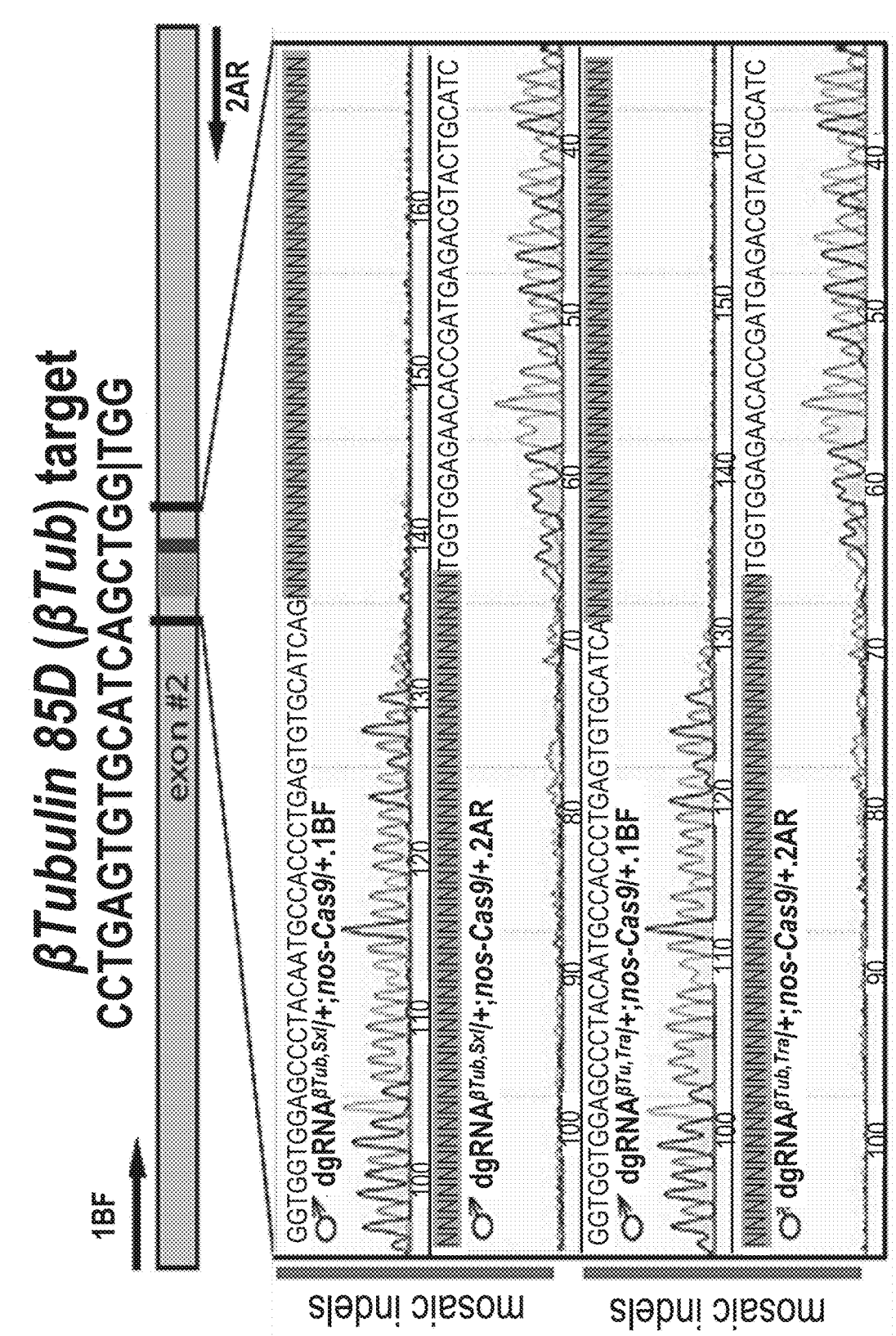
Figure 20:
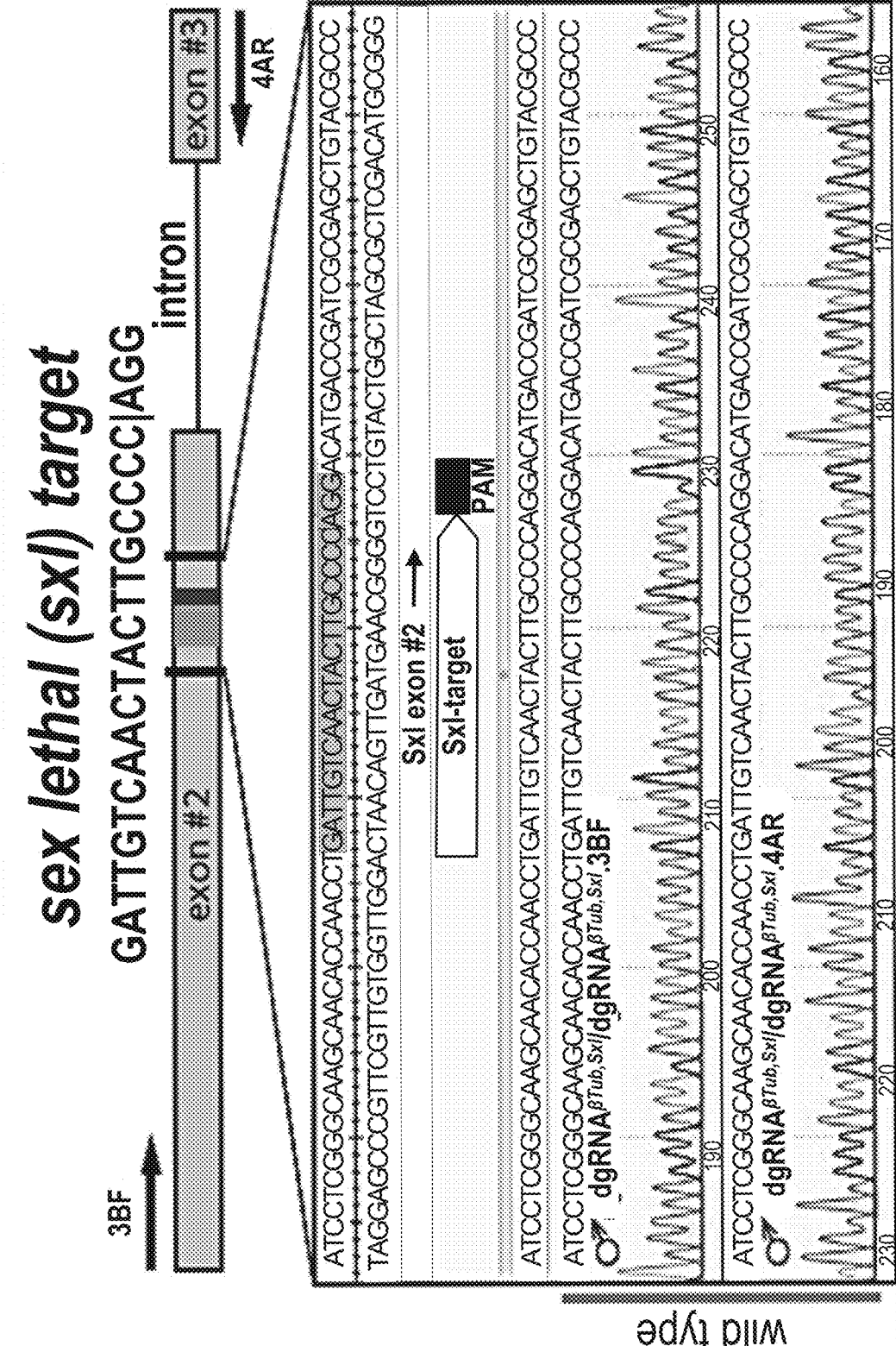

FIG. 2N is a schematic of the sequence information with respect to the βTubulin85D (βTub) target in the trans-heterozygous dgRNA$^{\beta Tub,Sxl}$/+; nos-Cas9/+ (double knockout) sterile males (♂) showing mosaic insertions/deletions (indels) precisely at the βTub target site, according to embodiments of the present disclosure. Diagrams on the top present positions of gRNA target sites and primers used for PCR relative to genetic structures of targeted genes. Sequence reads from both ends inferred diversity of templates that specifically localized at the sites targeted with gRNAs in the sterile ♂, while the wild type ♂ had single alleles without any sequence ambiguity.

Figure 2O:
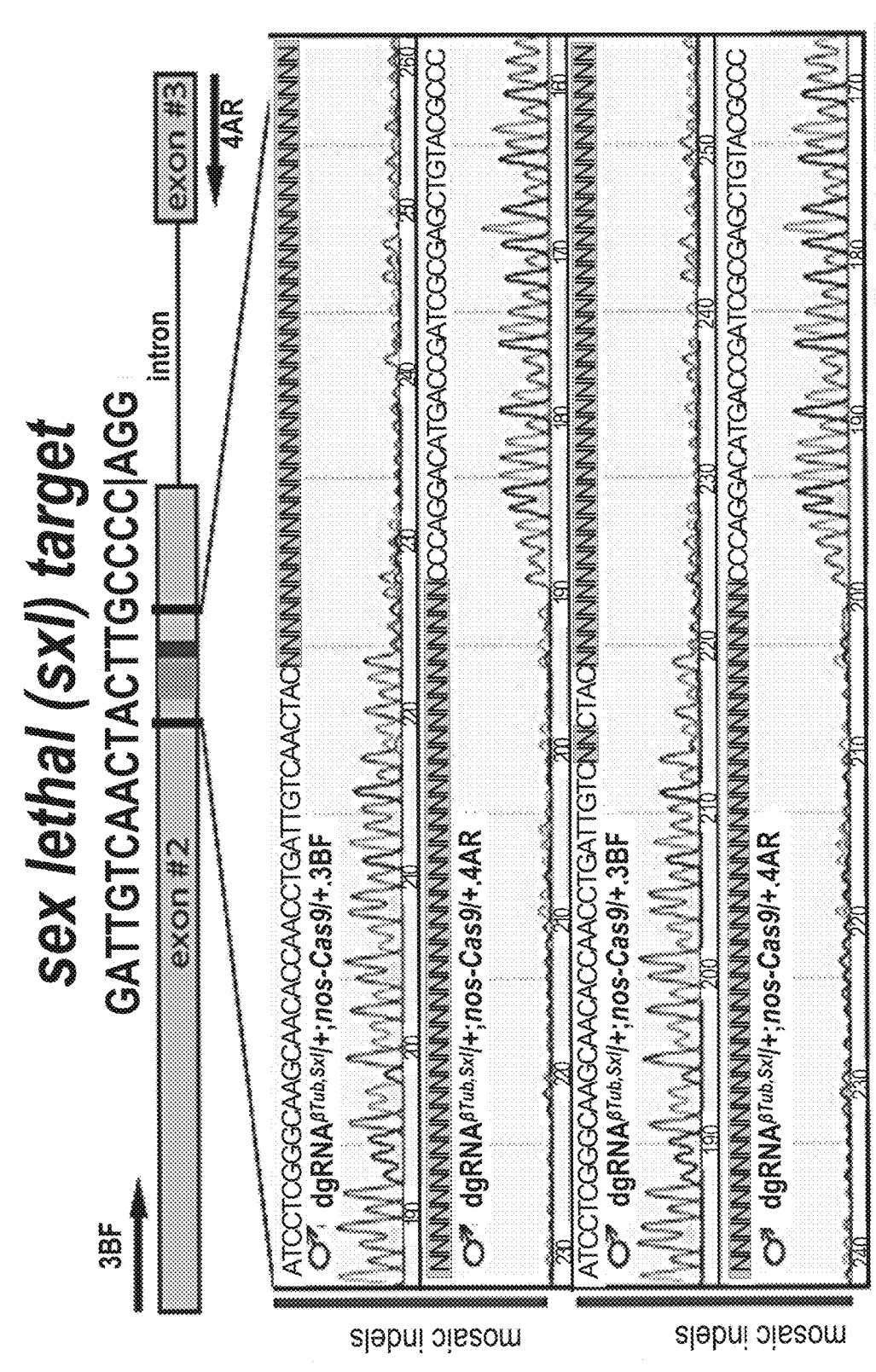

FIG. 2O is a schematic of the sequence information with respect to the Sex Lethal (Sxl) target in the trans-heterozygous dgRNA$^{\beta Tub,Sxl}$/+; nos-Cas9/+ (double knockout) sterile males (♂) showing mosaic indels identified at the Sxl target site in the same dgRNA$^{\beta Tub,Sxl}$/+; nos-Cas9/+ sterile males (♂) and may be related to pupal lethality of trans-heterozygous females observed in FIGS. 2D-2E, according to embodiments of the present disclosure. Diagrams on the top present positions of gRNA target sites and primers used for PCR relative to genetic structures of targeted genes. Sequence reads from both ends inferred diversity of templates that specifically localized at the sites targeted with gRNAs in the sterile ♂, while the wild type ♂ had single alleles without any sequence ambiguity.

Figure 2P:
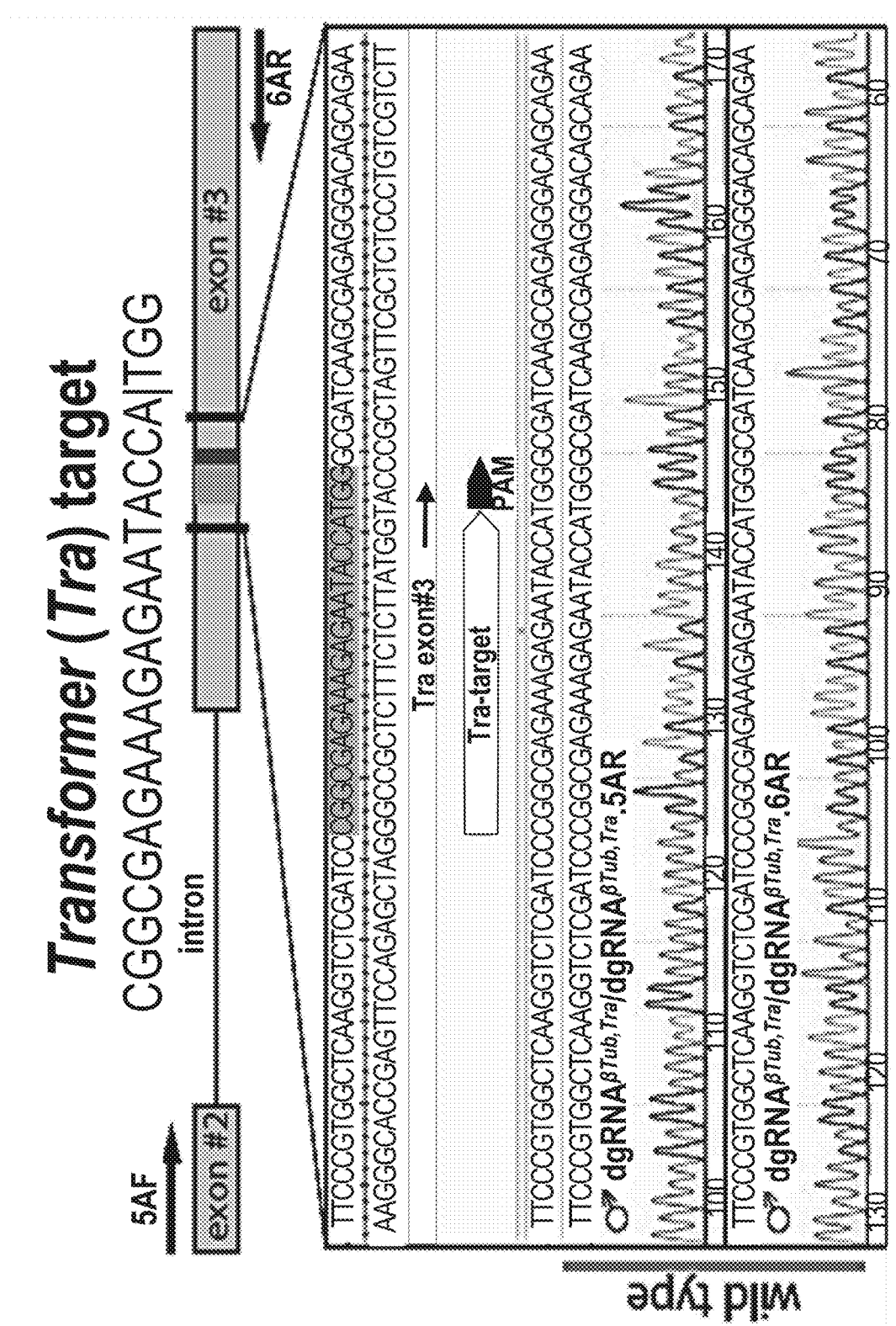
Figure 2P:
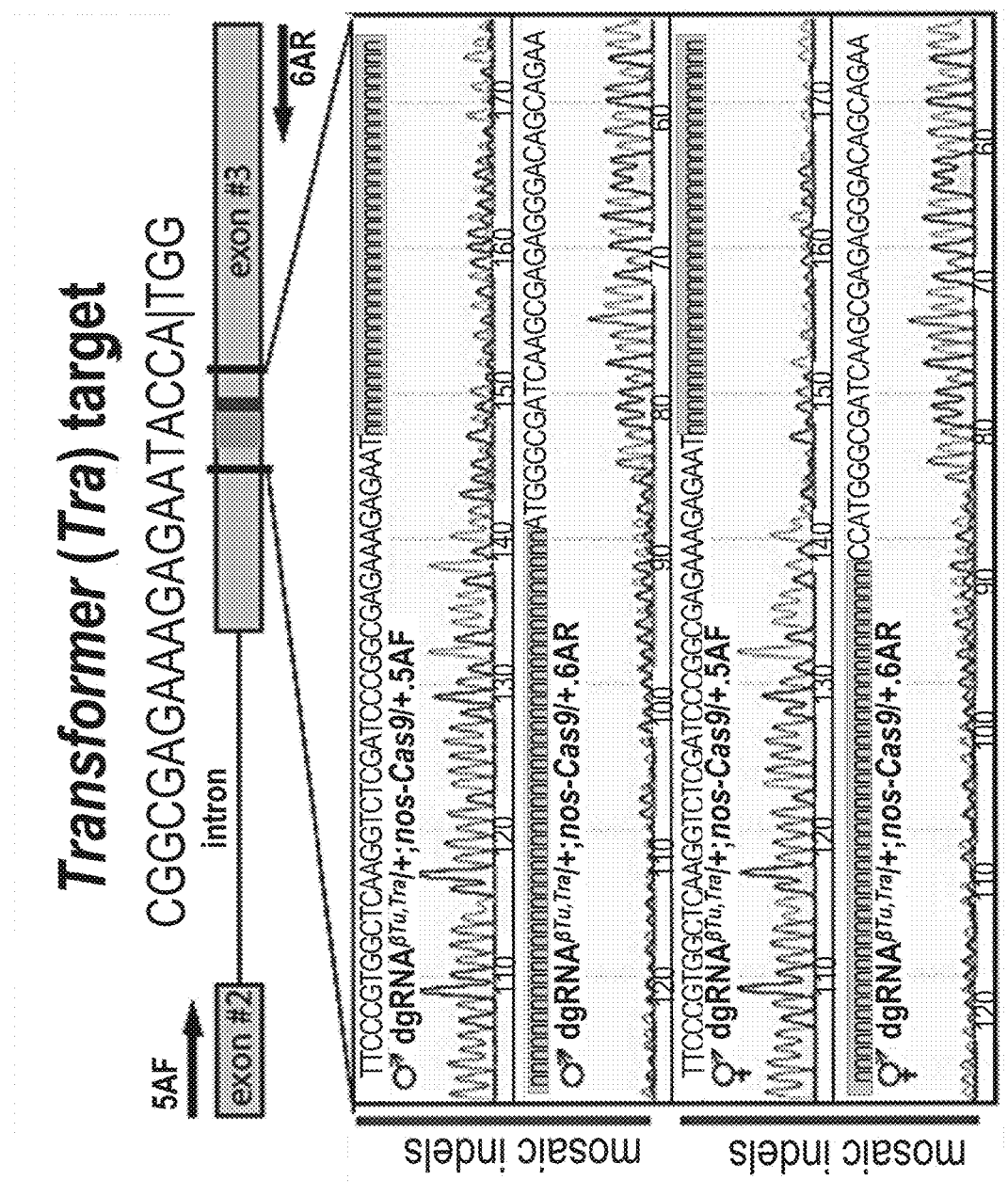

FIG. 2P is a schematic of the sequence information with respect to the Transformer (Tra) target in the trans-heterozygous dgRNA$^{\beta Tub,Tra}$/+; nos-Cas9/+ double knock-out sterile males (♂) and intersexes (□) showing mosaic insertions/deletions (indels) located at the Tra site targeted by dgRNA$^{\beta Tub,\ Tra}$ double guide RNAs (dgRNA), according to embodiments of the present disclosure. Diagrams on the top show positions of gRNA targets and primers used for PCR relative to genetic structures of targeted genes. Sequence reads from both ends inferred diversity of templates that specifically localized at the sites targeted with gRNAs in sterile ♂ and □, though the wild type ♂ had single alleles without any sequence ambiguity at both sites.

Figure 2Q:
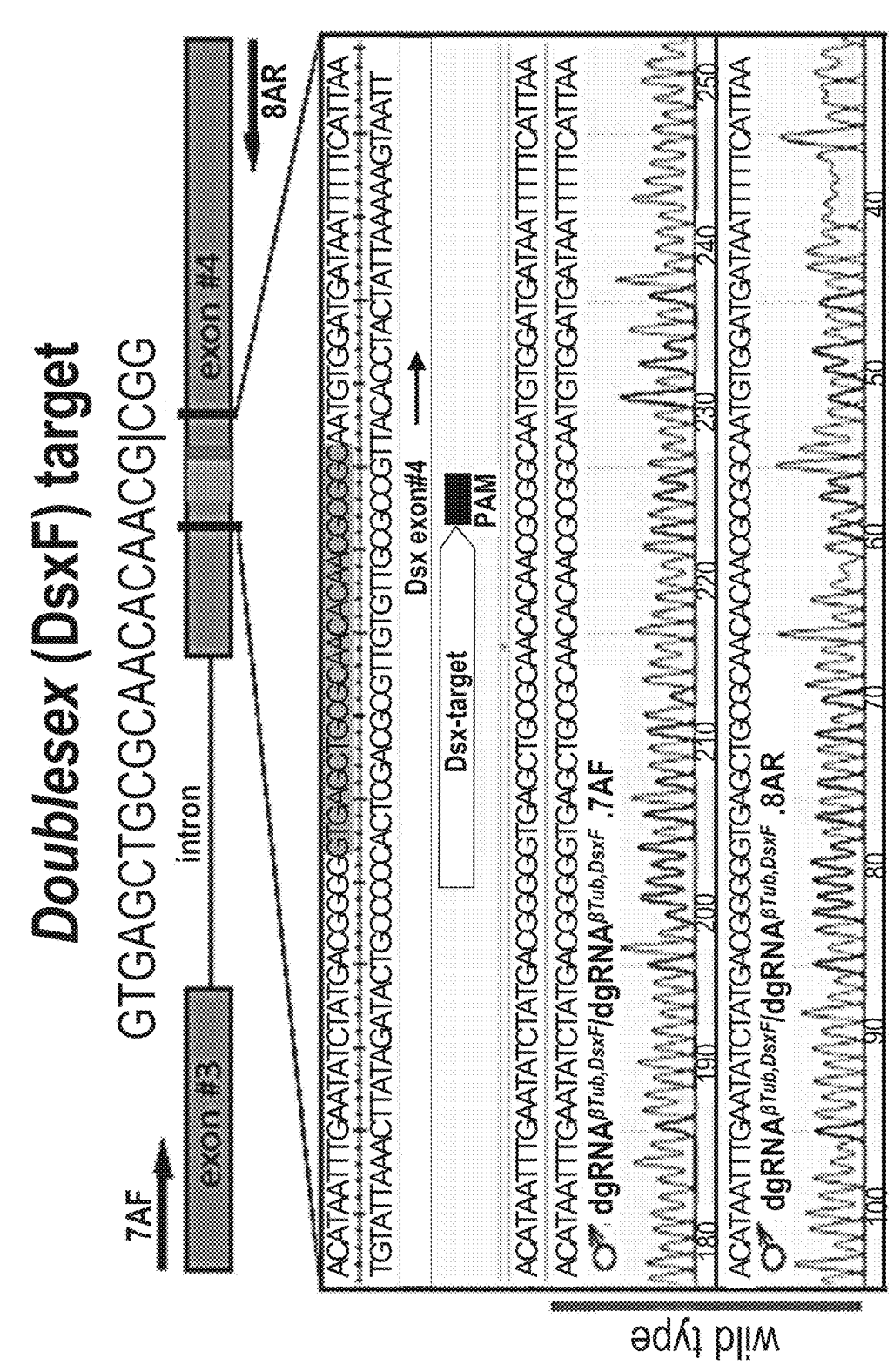
Figure 2Q:
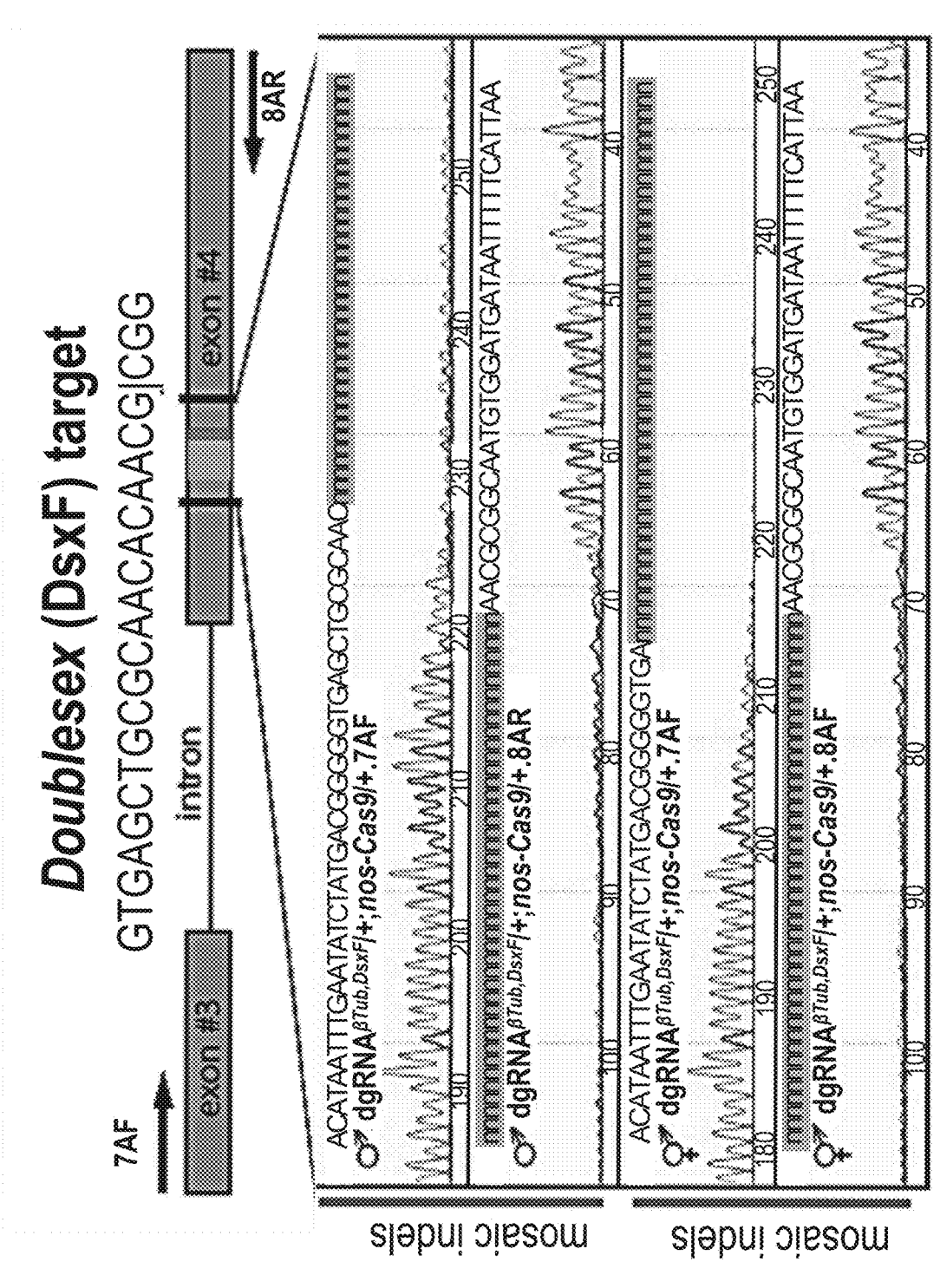

FIG. 2Q is a schematic of the sequence information with respect to the Doublesex (DsxF) target in the trans-heterozygous dgRNA$^{\beta Tub,DsxF}$ double gRNAs in dgRNA$^{\beta Tub,DsxF}$+; nos-Cas9/+ sterile ♂ and □ showing mosaic indels were identified at the DsxF site target, according to embodiments of the present disclosure. Diagrams on the top show positions of gRNA targets and primers used for PCR relative to genetic structures of targeted genes. Sequence reads from both ends inferred diversity of templates that specifically localized at the sites targeted with gRNAs in sterile ♂ and □, though the wild type ♂ had single alleles without any sequence ambiguity at both sites.

Figure 3A:
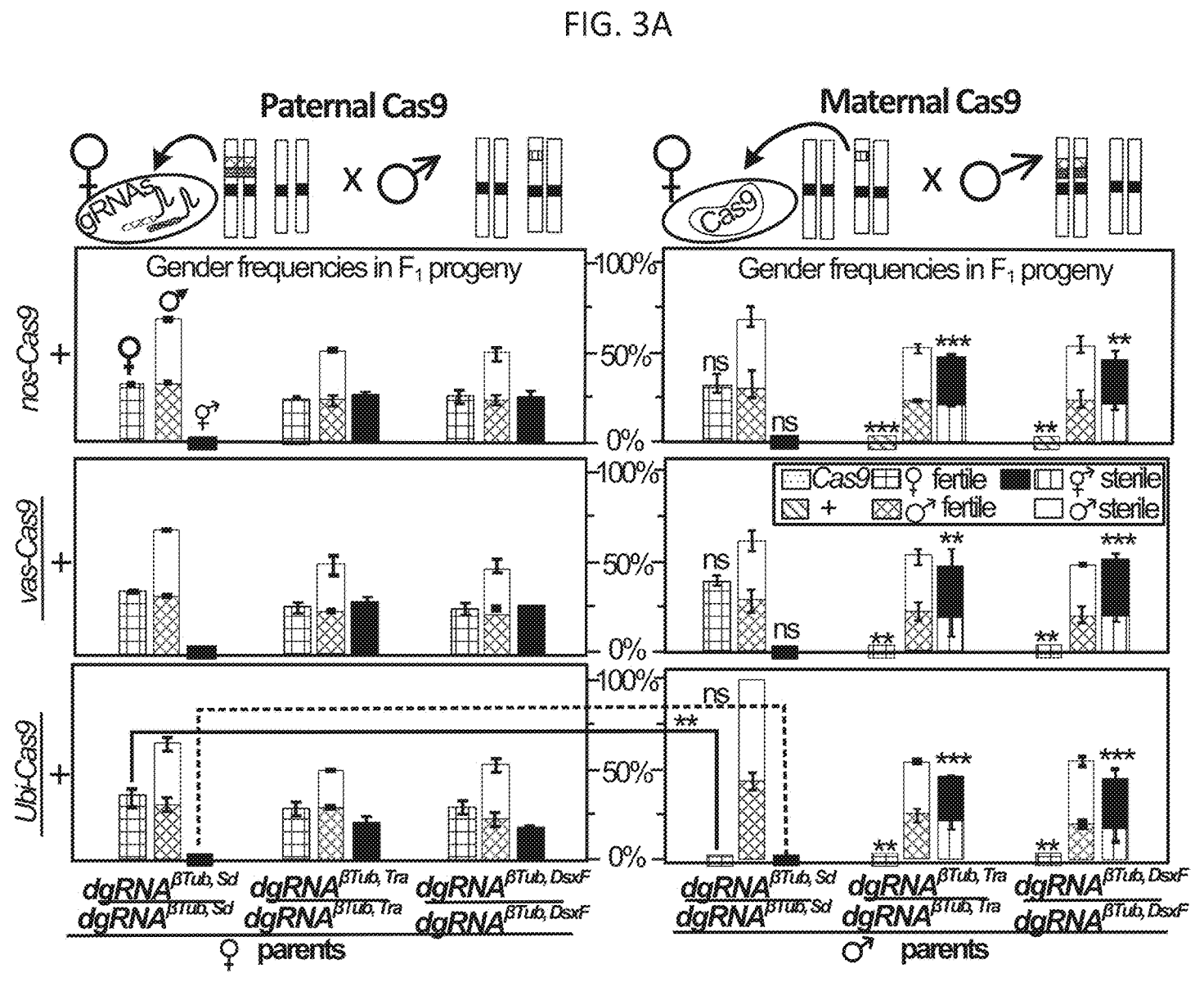

FIG. 3A shows bar graphs representing genetic quantification of the dominant effect by maternal loading of Cas9, in which genotypes, gender frequencies, and fertility of flies generated by reciprocal crosses between homozygous dgRNAs and heterozygous Cas9 flies are indicated by the pink, blue, orange, or grey solid or striped bars as shown in the figure legends. The progeny from crosses with heterozygous paternal Cas9 are shown in the left panels and the heterozygous maternal Cas9 are shown in the right panels. Each bar shows an average gender frequency and one standard deviation. Statistical significance was calculated with t tests assuming unequal variance. (P>0.01, P>0.001*). Striped bars indicate inheritance of Cas9 as a gene, while solid bars indicate inheritance of + allele.

Figure 3B:
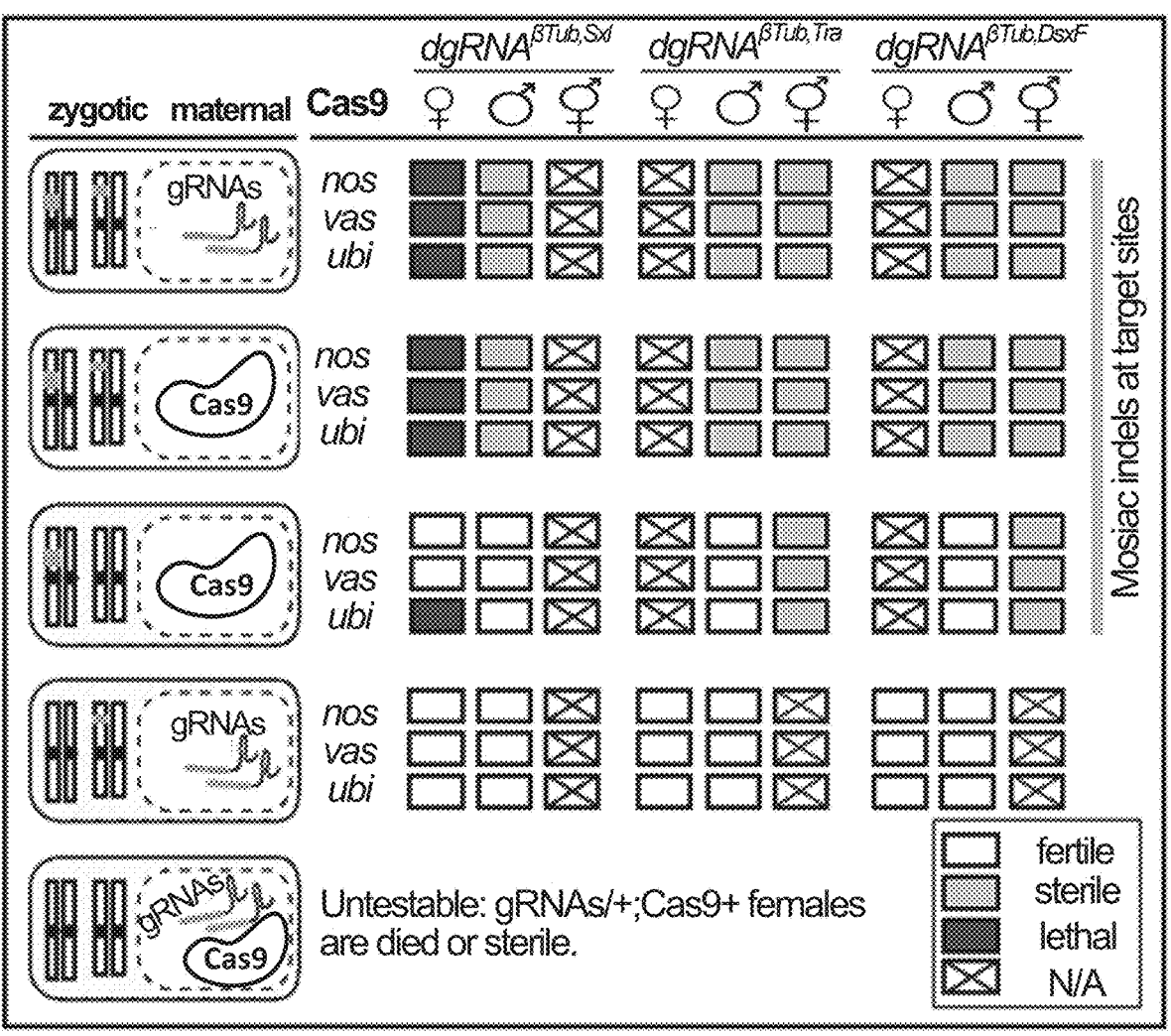

FIG. 3B is a schematic table showing combinations of genotypes and maternal/zygotic contributions in embryos, and their penetrance, according to embodiments of the present disclosure.

Figure 3C:
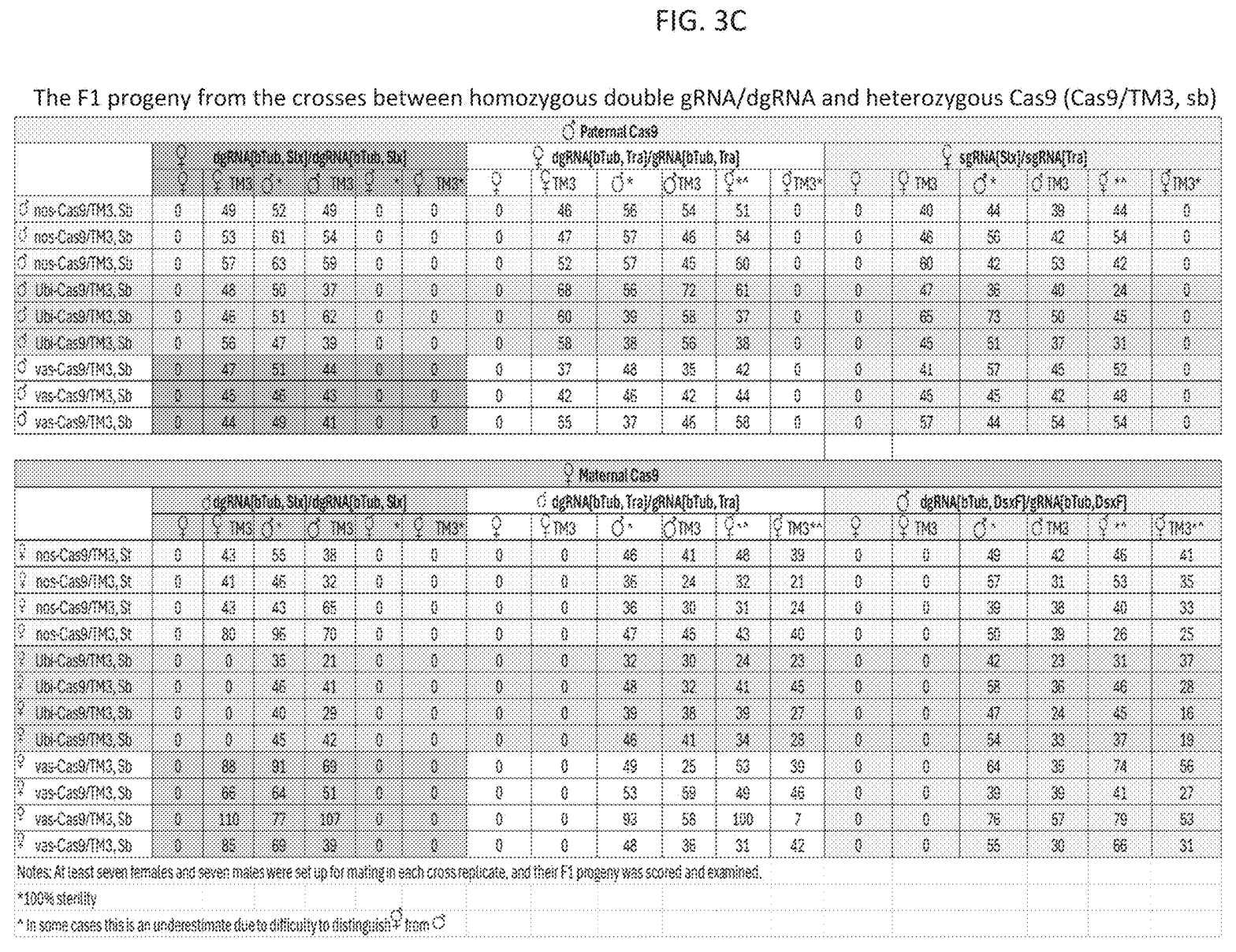

FIG. 3C is a table of the $F_1$ progeny from the crosses between homozygous double gRNAs (dgRNAs/dgRNAs) and heterozygous Cas9 (Cas9/TM3, Sb), according to embodiments of the present disclosure.

Figure 3D:
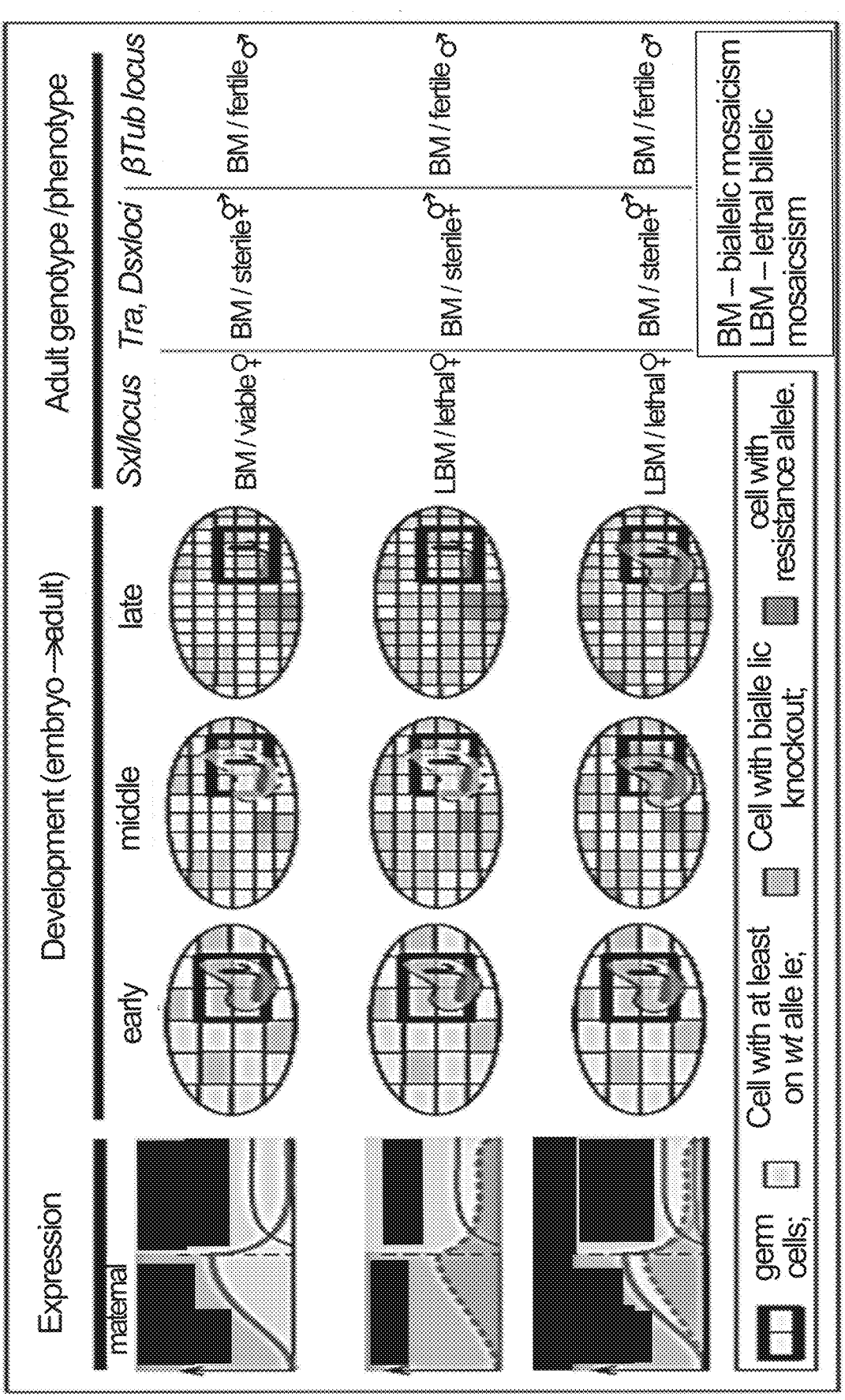

FIG. 3D is a schematic table showing accumulation of high levels of biallelic mosaicism (BM) throughout insect development leads to the loss of gene function at the organismic level and ensures complete penetrance of induced phenotypes: lethality (lethal biallelic mosaicism (LBM)) (pink boxes), female masculinization, or male sterility, as indicated. Complementation of gene function in some cells by uncleaved wt alleles (light green boxes), and resistance alleles (yellow boxes) generated by NHEJ, are not sufficient to rescue the induced phenotype at the organismic level and therefore 100% of trans-heterozygous progeny have the induced phenotypes. Boxes get smaller and more abundant as cells divide.

Figure 4A:
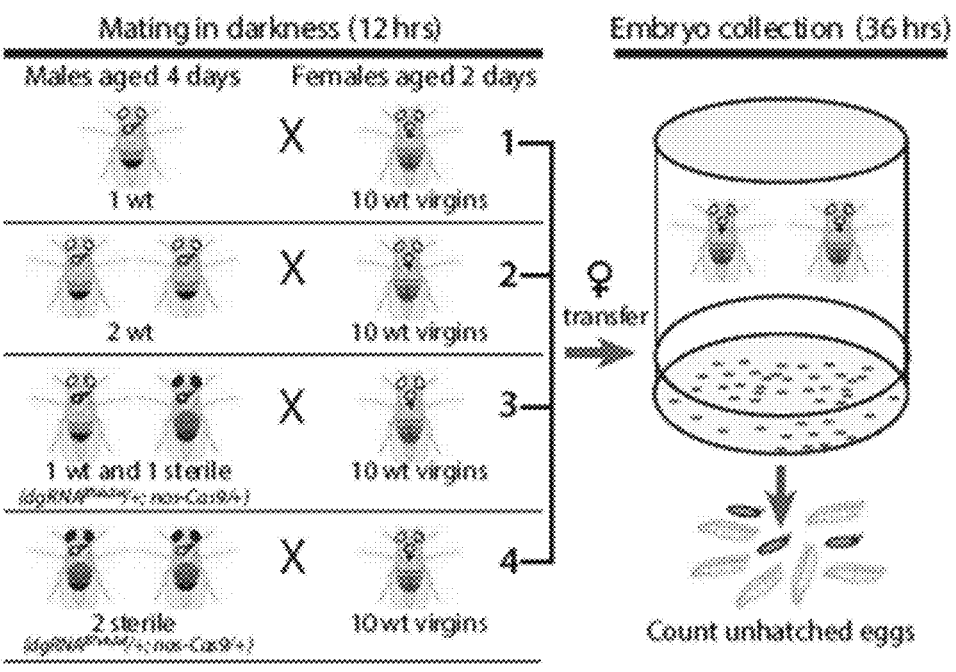

FIG. 4A is a schematic of an experimental setup to estimate the mating competitiveness of dgRNA$^{\beta Tub,Sxl}$/+; nos-Cas9/+ sterile males (marked with red) competing against wt males to secure matings with wt females, according to embodiments of the present disclosure. A mated female is resistant to the next mating for around 24 hours, and the mating success of sterile males was evaluated by fertility decrease (e.g., by the increase of unhatched egg rate).

Figure 4B:
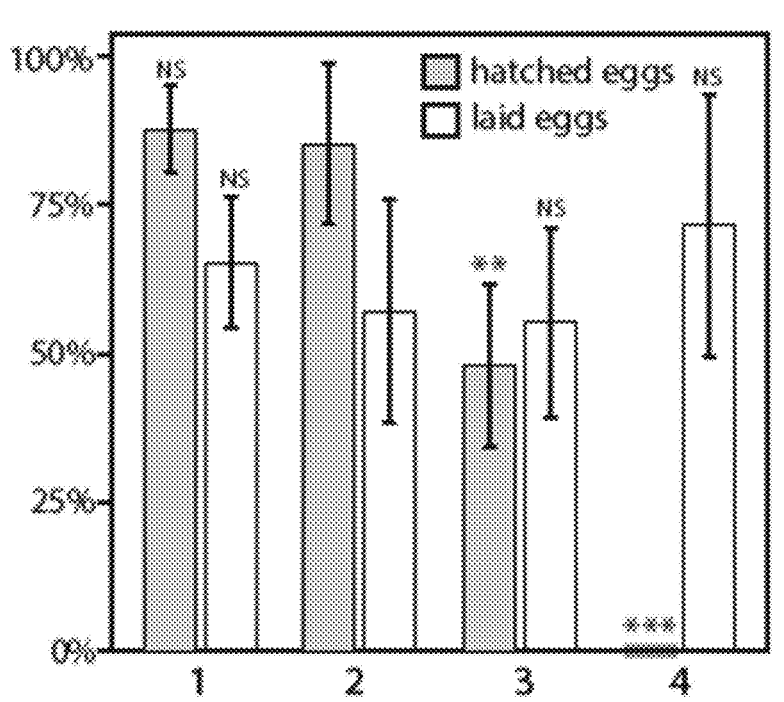

FIG. 4B shows bar graphs showing percentages of laid and hatched eggs where the number of laid eggs were normalized against the highest egg number (n=199) to convert them to the percentile as indicated in the table of FIG. 4C. The presence of one sterile male resulted in a significant decrease in female fertility (#3 vs #2) that could not be accounted by removal of one wt male (#2 vs #1). Statistical significance was calculated with a t test assuming unequal variance comparing group #3 to #2 and #1 (P>0.003, P>0.0001*).

FIG. 4C is a table of mating competitiveness based on laid, unhatched, and hatched eggs for dgRNA$^{bTub,Sxl}$/+; nos-Cas9/+ males compared to wild type males with the indicated crosses, according to embodiments of the present disclosure.

Figure 4D:
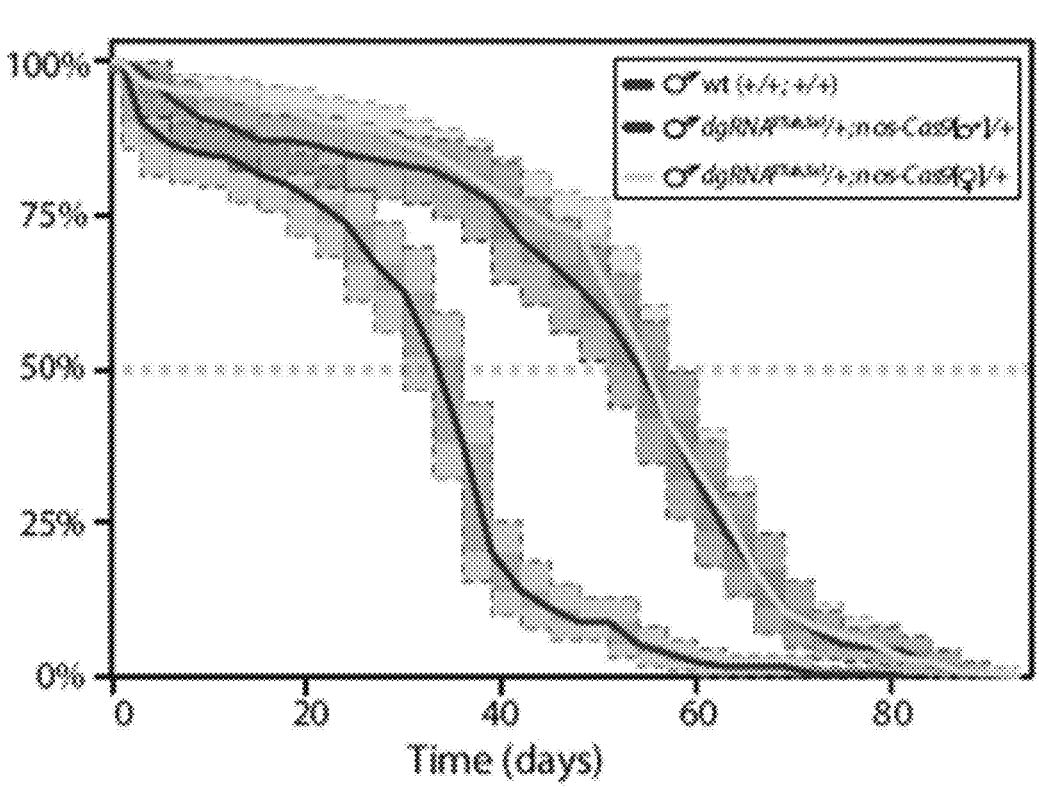

FIG. 4D is a graph of survival curves of wt males (blue line) and two types of dgRNA$^{\beta Tub,Sxl}$/+; nos-Cas9/+ sterile males, with paternal (red line) or maternal (green line) Cas9 inheritance, according to embodiments of the present disclosure. Survival curves shows non-parametric maximum likelihood estimates (NPMLE) for three male groups, along with bootstrap estimated 95% confidence intervals shown with light shade, and representational non-uniqueness shown with dark shade. The y-axis shows the estimated survival percentage. Both types of pgSIT males lived significantly longer than wt males (P<2.2$^{-16}$), while no statistically significant difference was found between two types of pgSIT males. Sun's generalization of the logrank test was used to test for differences in survival curves.

FIG. 4E is a table of longevity data (lifespan in days) for dgRNA$^{bTub,Sxl}$/+; nos-Cas9/+ males compared to control w− males, according to embodiments of the present disclosure.

FIG. 4F is a table of the input parameters used in *Aedes aegypti* population suppression model, as disclosed herein, according to embodiments of the present disclosure. The entire contents of all of the cited references as indicated in the table are incorporated herein by reference.

Figure 4G:
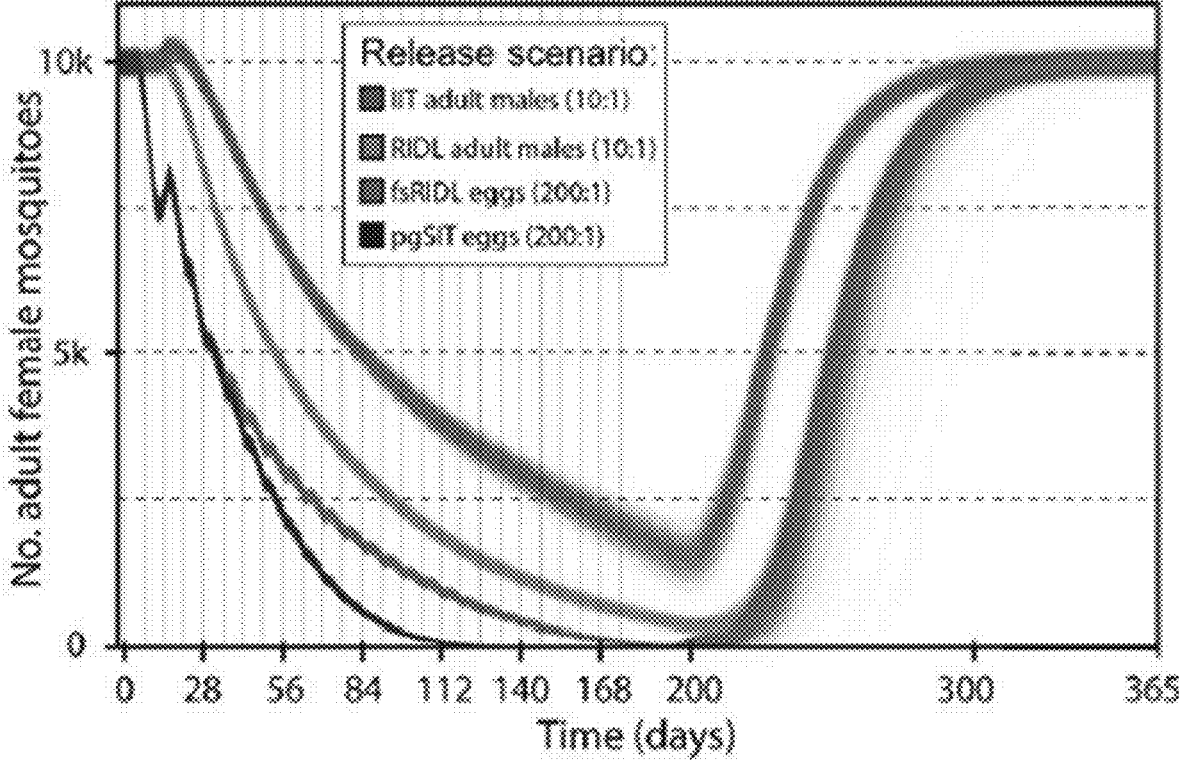

FIG. 4G is a graph of the model-predicted impact of releases of pgSIT eggs (dark blue) on *Aedes aegypti* mosquito population density with comparison to releases of *Wolbachia*-based incompatible insect technique (IIT) (purple), release of insects carrying a dominant lethal gene (RIDL) (light blue), and female-specific RIDL (fsRIDL) (red) using a suppression model as described herein, according to embodiments of the present disclosure. Releases are carried out weekly over a six-month period with release ratios (relative to wild adults) as indicated in the inset legend. Model predictions were computed using 2000 realizations of the stochastic implementation of the MGDrivE simulation framework for a randomly-mixing *Ae. aegypti* population of 10,000 adult females and model parameters described in the table of FIG. 4F. As shown, pgSIT releases outcompete those of all other suppression or reduction technologies, showing the highest potential to eliminate the local population.

Figure 4H:
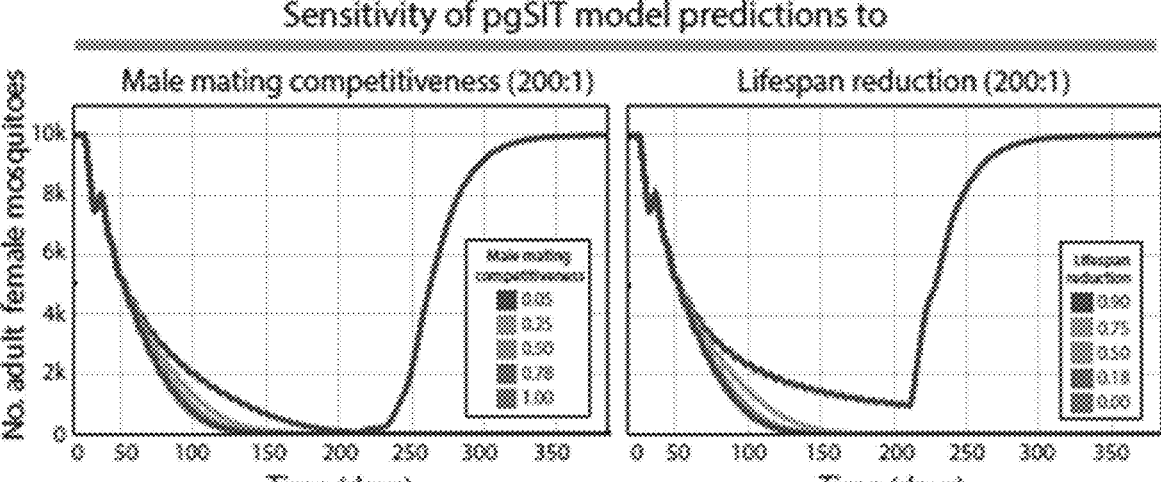

FIG. 4H shows graphs measuring the sensitivity of pgSIT model predictions to male mating competitiveness, lifespan reduction with a release ratio of 200 eggs per wild adult, keeping all other parameters constant as set forth in the table of FIG. 4F. Model predictions were computed using 250 realizations of the stochastic implementation of the MGDrivE simulation framework for a randomly-mixing *Ae. aegypti* population of 10,000 adult females. As shown in the left graph, with a weekly release ratio of 200 eggs per wild adult and keeping lifespan reduction due to the pgSIT construct constant at 18%, elimination can be reliably achieved for a male mating competitiveness of 25%; but not for 5%, as is the case for RIDL adult males, according to embodiments of the present disclosure. As shown in the right graph, with a weekly release ratio of 200 eggs per wild adult and keeping male mating competitiveness constant at 78%, elimination can be reliably achieved for lifespan reductions less than or equal to 75%, according to embodiments of the present disclosure.

Figure 4I:
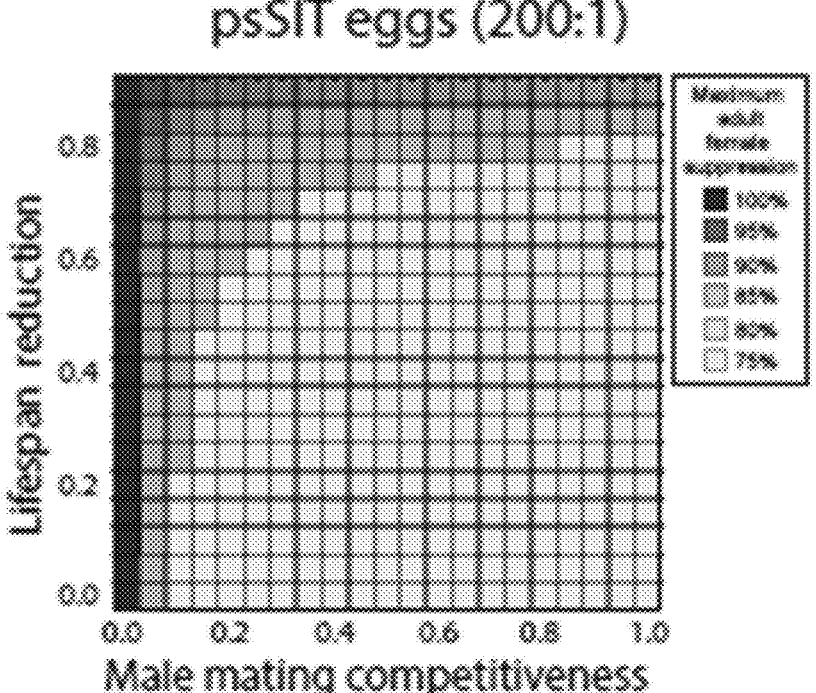

FIG. 4I is a graph showing a wide range of parameter values (varying lifespan reduction and male mating competitiveness concurrently as indicated) for which local *Ae. aegypti* elimination can be reliably achieved (tan tiles) given a weekly release ratio of 200 eggs per wild adult, according to embodiments of the present disclosure.

Figure 4J:
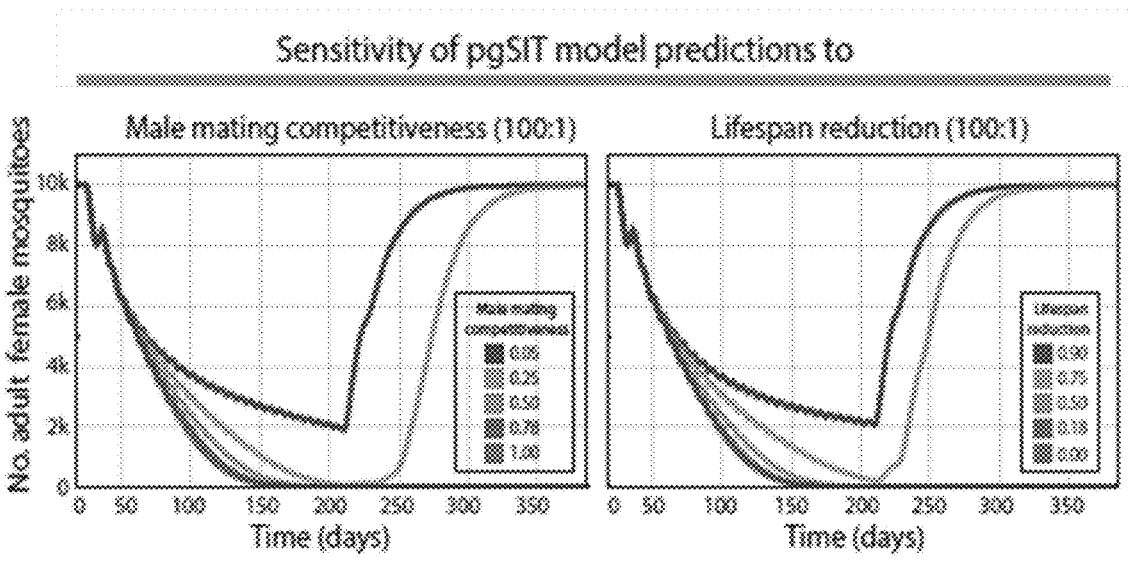

FIG. 4J shows graphs measuring the sensitivity of pgSIT model predictions to male mating competitiveness, lifespan reduction with a release ratio of 100 eggs per wild adult, keeping all other parameters constant as set forth in the table of FIG. 4F. As shown in the left graph, with a weekly release ratio of 100 eggs per wild adult and keeping lifespan reduction due to the pgSIT construct constant at 18%, elimination can be reliably achieved for a male mating competitiveness of 50%; but not for 25%, according to embodiments of the present disclosure. As shown in the right graph, with a weekly release ratio of 100 eggs per wild adult and keeping male mating competitiveness constant at 78%, elimination can be reliably achieved for lifespan reductions less than or equal to 50%, according to embodiments of the present disclosure.

Figure 4K:
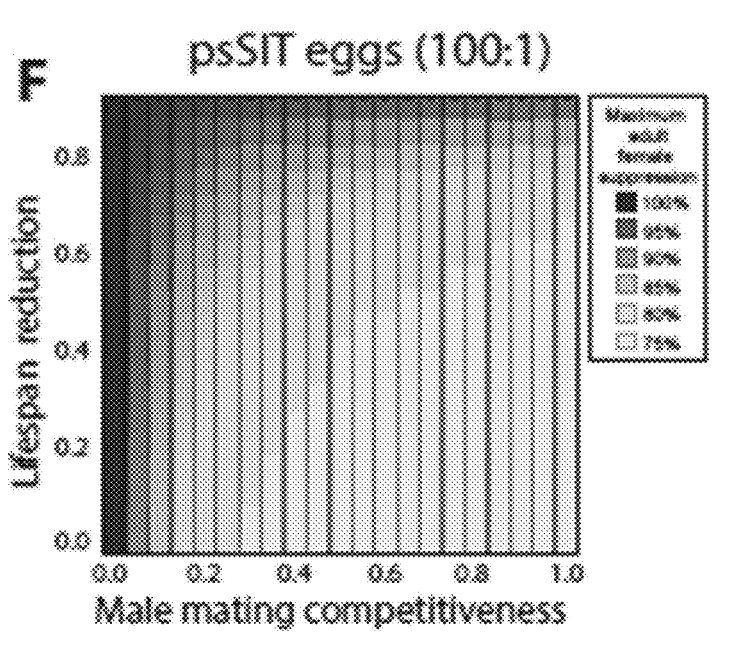

FIG. 4K is a graph showing a wide range of parameter values (varying lifespan reduction and male mating competitiveness concurrently as indicated) for which local *Ae. aegypti* elimination can be reliably achieved (tan tiles) given a weekly release ratio of 100 eggs per wild adult, according to embodiments of the present disclosure.

Figure 5:
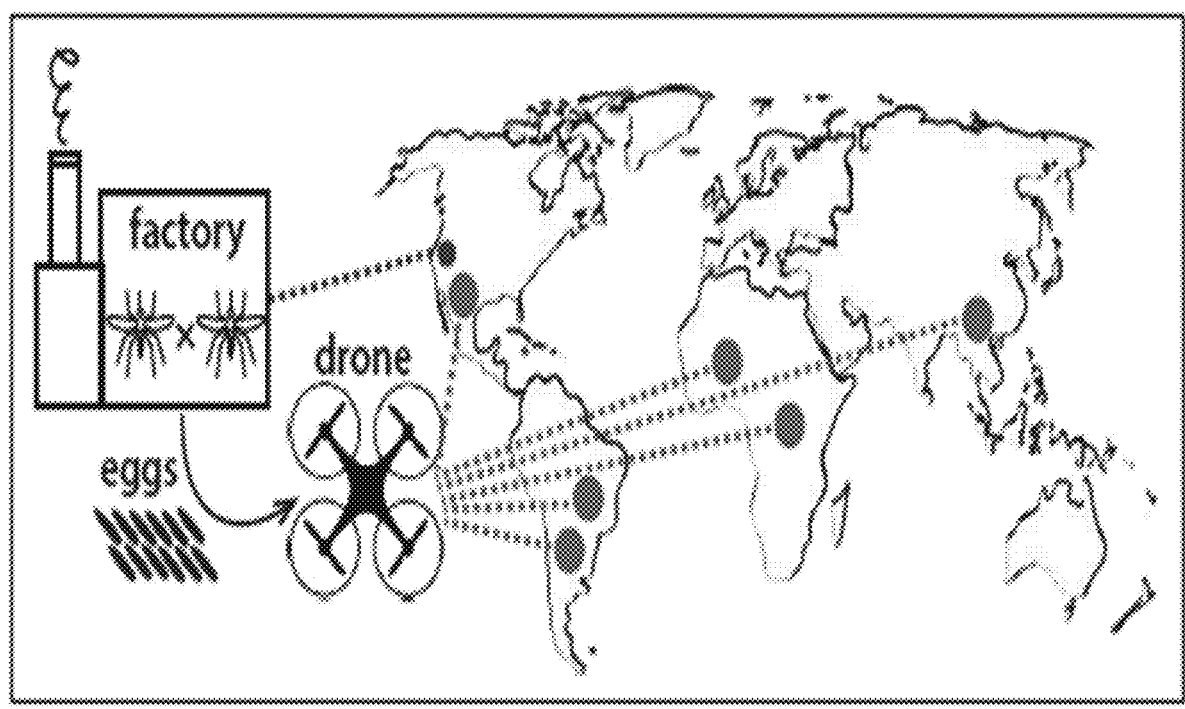

FIG. 5 is a schematic showing a factory located in the United States (blue dot) for producing pgSIT eggs for distribution (e.g., by drone) and released at remote locations worldwide (e.g., in South America, Africa, and Asia (pink dots)), according to embodiments of the present disclosure.

DETAILED DESCRIPTION

The sterile insect technique (SIT) is an environmentally safe and proven technology to suppress to reduce wild populations. Embodiments of the present disclosure include methods for genetically modifying insects using a CRISPR-based technology referred to herein as "precision guided SIT" (pgSIT) methods. As disclosed in more detail throughout the present disclosure, pgSIT methods mechanistically rely on a dominant genetic technology that enables sexing as well as concurrent or simultaneous sexing and sterilization in insects. The concurrent or simultaneous sexing and sterilization of insect eggs, allows for the capability to release eggs into the environment ensuring sterile adult males emerge. For field applications, the release of eggs eliminates the burden of manually sexing and sterilizing males, thereby reducing overall effort and increasing scalability.

In order to demonstrate the efficacy of the pgSIT technology according to embodiments of the present disclosure, multiple pgSIT systems were engineered and demonstrated in *Drosophila* as an example insect. The genetic techniques and methods described and referenced herein are understood to be applicable to a broad range of insects.

The presently disclosed pgSIT methods of male sexing and methods of male sexing and sterility use the precision and accuracy of CRISPR-based technology to disrupt genes essential for female viability (for male sexing) or concurrently or simultaneously disrupt genes essential for female viability and male fertility. The pgSIT methods of the present disclosure utilize a simple breeding scheme requiring two insect strains (a first parent strain and a second parental strain), one expressing an endonuclease (e.g., Cas9) and the other expressing a nucleic acid sequence construct having at least one guide polynucleotide directed to the gene or genes to be disrupted. A single mating between these two parental strains mechanistically results in synchronous polynucleotide-guided (e.g., RNA-guided) dominant allelic or dominant biallelic knockouts of the target gene or genes throughout development.

CRISPR technology refers to clustered regularly interspaced short palindromic repeats and has been extensively studied and modified for genome editing in most studied organisms as disclosed in Sternberg and Doudna, Mol. Cell 58, 568-574 (2015), the entire contents of which are herein incorporated by reference.

As used herein, with respect to the CRISPR-based technology, the term "guide polynucleotide" refers to a polynucleotide having a "synthetic sequence" capable of binding the corresponding endonuclease enzyme protein (e.g., Cas9) and a variable target sequence capable of binding the genomic target (e.g., a nucleotide sequence found in an exon of a target gene). In some embodiments of the present disclosure, a guide polynucleotide is a guide ribonucleic acid (gRNA). In some embodiments, the variable target sequence of the guide polynucleotide is any sequence within the target that is unique with respect to the rest of the genome and is immediately adjacent to a Protospacer Adjacent Motif (PAM). The exact sequence of the PAM sequence may vary as different endonucleases require different PAM sequences. As used herein, the expression "single heterologous construct having two different single guide RNAs (sgRNAs)" refers to a double guide RNA (dgRNA).

With respect to the endonuclease enzyme protein of the CRISPR-based technology, the term "endonuclease" refers to any suitable endonuclease enzyme protein or a variant thereof that will be specifically directed by the selected guide polynucleotide to enzymatically knock-out the target sequence of the guide polynucleotide. As used herein, the term "variant thereof," as used with respect to an endonuclease, refers to the referenced endonuclease in its enzymatically functional form expressed in any suitable host organism or expression system and/or including any modifications to enhance the enzymatic activity of the endonuclease.

The examples disclosed throughout the present disclosure represent methods for producing sterile male insect progeny in which both a female viability gene and a male fertility gene are disrupted using at least two guide polynucleotides. However, as would be understood by one of ordinary skill in the art, methods for directing male sexing include the presently disclosed method in which a gene essential for female viability is targeted and genes for male sterility are not targeted. For example, with reference to FIG. 1A, the endonuclease parent insect (labeled Cas9 line) is crossed with the guide RNA parent (gRNA line) having two gRNAs (one blue, one green) targeting a female-essential gene and a male sterility gene. However, for methods of directing male sexing, the gRNA line would not be genetically modified to express the male sterility gene.

As used herein, the terms "integrating," "integration," and like terms refers to the introduction of a heterologous recombinant nucleic acid sequence into the target insect. As would be understood by one of ordinary skill in the art, techniques for genetic modification of insects are known and described, for example in Cockburn et al., Biotechnology and Genetic Engineering Reviews, 2: 68-99, (1984), the entire contents of which are incorporate herein by reference. Integrating, as used herein, may refer to the integration of recombinant nucleic acid sequence into the genome of the target insect. The genome of the target insect includes at least one chromosome of the target insect, but may include all relevant chromosome copies. As such, integration into the genome may be heterozygous or homozygous.

As used herein, the term "introducing an endonuclease" into a target insect refers to the recombinant introduction of an endonuclease into the insect such that the endonuclease is present in the insect. Introduction of an endonuclease into an insect does not require genomic integration, but may include genomic integration. For example, introduction of an endonuclease includes "depositing" the endonuclease into the insect as described, for example, in Lin and Potter, G3, (2016), doi:10.1534/g3.116.034884, the entire content of which is incorporate herein by reference.

Additionally, while the examples of the present disclosure include methods for obtaining up to 100% male sterile progeny, methods for producing less than 100% male sterile progeny are also included within the scope of the present disclosure. For example, in some embodiments of the present disclosure, the parental insect strain expressing the guide polynucleotide may be heterozygous or homozygous for the guide polynucleotide (single, double, or more guide polynucleotides). In some embodiments, the parental insect strain expressing the guide polynucleotide is homozygous for the guide polynucleotide, thereby ensuring that all progeny receive the guide polynucleotide.

With reference to FIGS. 2A and 3A, in further embodiments of the present disclosure, if the parental insect strain expressing the endonuclease is male, the male parent may be heterozygous or homozygous for the endonuclease, whereas if the parental insect strain expressing the endonuclease is female, the endonuclease may be deposited in the female, expressed heterozygously, or homozygously.

With reference to FIG. 2F, if both parental strains are homozygous for their respective endonuclease or guide polynucleotide, all or almost all progeny receive the endonuclease and the guide polynucleotide(s) as a result of non-Mendelian complete penetrance. Accordingly, the desired phenotypes (e.g., all male insects or all male and sterile insects) in all progeny may be produced in a single generation. As used herein, the term "almost all progeny" refers to at least 70%, 75% 80%, 85%, 90%, 91%, 92%, 93%, 94%, 95%, 96%, 97%, 98%, or 99% of the progeny. In some embodiments of the present disclosure, viability of the progeny is determined at the adult stage.

In some embodiments of the present disclosure, methods for directing male sexing include introducing an endonuclease in a first insect parent and integrating at least one nucleic acid sequence construct into the genome of the second insect parent (e.g., a plasmid vector) the nucleic acid sequence having at least one first guide polynucleotide (e.g., a sgRNA or a dgRNA) targeting a nucleotide sequence in a female-essential genomic sequence) and mating the first insect parent and the second insect parent to produce all or almost all male progeny. As used herein, the term "female-essential genomic sequence" encompasses any genomic sequence or gene specific to the female insect. Examples of a female-essential genomic sequence include a sex-determination gene or a female-specific splice variant thereof, a gene or splice variant of a gene not found in the male, a gene or splice variant of a gene essential for female gonadal development, and/or a gene or splice variant of a gene not essential for male viability. With reference to FIG. 1B, non-limiting examples of female-essential genomic sequences include the female-specific exons in the sex-determination *Drosophila* genes Sxl, Tra, and Dsx including homologs, orthologs, and paralogs thereof. As used herein, the term "homolog" refers to the comparable gene of an organism found in another organism conferring the same function. As used herein, the terms "orthologs" and "paralogs" refer to types of homologs. Orthologs are corresponding genes in different lineages and are a result of speciation, and paralogs result from a gene duplication.

The regulation and sex-specific alternative splicing mediated by the TRA protein or the TRA/TRA-2 complex in insects is known and discussed in Pane et al., Development 129: 3715-3725 (2002), the entire content of which is incorporated herein by reference. The male- and female-specific splice products of the Dsx gene are known and discussed in Suzuki et al., Insect Biochem Mol Biol 31: 1201-1211 (2001), Salvemini et al., BMC Evol. Biol. 11, 41 (2011), and Scali et al., J. Exp. Biol. 208, 3701-3709 (2005), the entire contents of all of which are incorporated herein by reference.

In some embodiments of the present disclosure, a method for directing male sexing includes introducing an endonuclease in a first insect parent and integrating at least one nucleic acid sequence construct into the genome of the second insect parent, the nucleic acid sequence having at least one first guide polynucleotide targeting a nucleotide sequence in a female-essential genomic sequence selected from female-specific exons in the Tra and/or Dsx genes, including homologs, orthologs, or paralogs thereof, where the first insect parent and the second insect parent are mated to produce all or almost all male progeny.

In some embodiments of the present disclosure, a method for producing male sterile insect eggs includes introducing an endonuclease in a first insect parent and integrating at least one nucleic acid sequence construct into a genome of a second insect parent, the at least one nucleic acid sequence construct having at least one first guide polynucleotide targeting a female-essential genomic sequence required for female-specific viability or development and at least one second guide polynucleotide targeting a male sterility genomic sequence that is required for male fertility, and mating the first insect parent and the second insect parent to produce all or almost all sterile male progeny. As used herein, the term "male sterility genomic sequence" refers to any male-specific genomic sequence required for male fertility in an insect which does not affect the development of the male insect or the viability of the male insect. Non-limiting examples of a male-specific genomic sequence required for male fertility in an insect include the genes βTubulin 85D (βTub), fuzzy onions (Fzo), protamine A (ProtA), and spermatocyte arrest (Sa) and homologs, orthologs, and paralogs thereof. In some embodiments, the nucleic acid sequence construct includes one or more second guide polynucleotides targeting one or more male-specific genomic sequence required for male fertility. The functional conservation of βTubulin 85D including *Anopheles* and *Aedes aegypti* is described in Catteruccia et al., Nat. Biotechnol. 23, 1414-1417 (2005) and Smith et al., Insect Mol. Biol. 16, 61-71 (2007), the entire contents of both of which are incorporated herein by reference.

As would be understood by a person of ordinary skill in the art, many genes important for female viability and male fertility may be targeted. Additional female/male specific insect genes for disruption are discussed in Akbari et al., G3 3, 1493-1509 (2013) and Papa et al., (2016) doi:10.1101/081620, the entire contents of both of which are incorporated herein by reference.

In some embodiments of the present disclosure, the genetically modified insects and methods for generating the genetically modified insects include insects from the Order Diptera, Lepidoptera, or Coleoptera.

In some embodiments of the present disclosure, the genetically modified insects and methods for generating the genetically modified insects include an insect selected from a mosquito of the genera *Stegomyia, Aedes, Anopheles,* or *Culex.* Of these genera, example mosquito species include *Aedes aegypti, Aedes albopictus, Ochlerotatus triseriatus* (*Aedes triseriatus*), *Anopheles stephensi, Anopheles albimanus, Anopheles gambiae, Anopheles quadrimaculatus, Anopheles freeborni, Culex* species, or *Culiseta melanura.*

Additionally, Cas9-expressing strains have been developed in major dengue and malaria disease vectors including *Ae. aegypti, Anopheles gambiae,* and *Anopheles stephensi,* as respectively described in Li et al., (2017) doi:10.1101/156778, Hammond et al., Nat. Biotechnol. 34, 78-83 (2016), and Gantz et al. Proc. Natl. Acad. Sci. U.S.A. 112, E6736-43 (2015), the entire contents of all of which are incorporated herein by reference.

In some embodiments, the genetically modified insects and methods for generating the genetically modified insects include any insect selected from one of the following: tephritid fruit fly selected from Medfly (*Ceratitis capitata*), Mexfly (*Anastrepha ludens*), Oriental fruit fly (*Bactrocera dorsalis*), Olive fruit fly (*Bactrocera oleae*), Melon fly (*Bactrocera cucurbitae*), Natal fruit fly (*Ceratitis rosa*), Cherry fruit fly (*Rhagoletis cerasi*), Queensland fruit fly (*Bactrocera tyroni*), Peach fruit fly (*Bactrocera zonata*), Caribbean fruit fly (*Anastrepha suspensa*), Oriental Fruit Fly (*Bactrocera dorsalis*), West Indian fruit fly (*Anastrepha obliqua*), the New World screwworm (*Cochliomyia hominivorax*), the Old World screwworm (*Chrysomya bezziana*), Australian sheep blowfly/greenbottle fly (*Lucilia cuprina*), the pink bollworm (*Pectinophora gossypiella*), the European Gypsy moth (*Lymantria dispar*), the Navel Orange Worm (*Amyelois transitella*), the Peach Twig Borer (*Anarsia lineatella*), the rice stem borer (*Tryporyza incertulas*), the noctuid moths, Heliothinae, the Japanese beetle (*Papilla japonica*), White-fringed beetle (*Graphognatus* spp.), Boll weevil (*Anthonomous grandis*), the Colorado potato beetle (*Leptinotarsa decemlineata*), the vine mealybug (*Planococcus ficus*), Asian citrus psyllid (*Diaphorina citri*), Spotted wing *Drosophila* (*Drosophila suzukii*), Bluegreen sharpshooter (*Graphocephala atropunctata*), Glassy winged sharpshooter (*Homalodisca vitripennis*), Light brown apple moth (*Epiphyas postvittana*), Bagrada bug (*Bagrada hilaris*), Brown marmorated stink bug (*Halyomorpha halys*), Asian Gypsy Moth selected from the group of *Lymantria dispar asiatica, Lymantria dispar japonica, Lymantria albescens, Lymantria umbrosa,* and *Lymantria postalba*, Asian longhorned beetle (*Anoplophora glabripennis*), Coconut Rhinoceros Beetle (*Oryctes rhinoceros*), Emerald Ash Borer (*Agrilus planipennis*), European Grapevine Moth (*Lobesia botrana*), European Gypsy Moth (*Lymantria dispar*), False Codling Moth (*Thaumatotibia leucotreta*), fire ants selected from *Solenopsis invicta* Buren, and *S. richteri* Forel, Old World Bollworm (*Helicoverpa armigera*), Spotted Lanternfly (*Lycorma delicatula*), Africanized honeybee (*Apis mellifera scutellata*), Fruit and shoot borer (*Leucinodes orbonalis*), corn root worm (*Diabrotica* spp.), Western corn rootworm (*Diabrotica virgifera*), Whitefly (*Bemisia tabaci*), House Fly (*Musca domestica*), Green Bottle Fly (*Lucilia cuprina*), Silk Moth (*Bombyx mori*), Red Scale (*Aonidiella aurantia*), Dog heartworm (*Dirofilaria immitis*), Southern pine beetle (*Dendroctonus frontalis*), Avocado thrip (*Thysanoptera* Spp.), Botfly selected from *Oestridae* spp. and *Dermatobia hominis*), Horse Fly (*Tabanus sulcifrons*), Horn Fly (*Haematobia irritans*), Screwworm Fly selected from *Cochliomyia macellaria* (*C. macellaria*), *C. hominivorax, C. aldrichi,* or *C. minima*, Tsetse Fly (*Glossina* spp.), Warble Fly selected from *Hypoderma bovis* or *Hypoderma lineatum*, Spotted lanternfly (*Lycorma delicatula*), Khapra beetle (*Trogoderma granarium*), Honeybee mite (*Varroa destructor*), Termites (*Coptotermes formosanus*), Hemlock woolly adelgid (*Adelges tsugae*), Walnut twig beetle (*Pityophthorus juglandis*), European wood wasp (*Sirex noctilio*), Pink-spotted bollworm (*Pectinophora scutigera*), Two spotted spider mite (*Tertanychus urticae*), Diamondback moth (*Plutella xylostella*), Taro caterpillar (*Spodoptera litura*), Red flour beetle (*Tribolium castaneum*), Green peach aphid (*Myzus persicae*), Cotton Aphid (*Aphis gossypii*), Brown planthopper (*Nilaparvata lugens*), Beet armyworm (*Spodotera exigua*), Western flower thrips (*Frankliniella occidentalis*), Codling moth (*Cydia pomonella*), Cowpea weevil (*Callosobruchus maculatus*), Pea aphid (*Acyrthosiphon pisum*), Tomato leafminer (*Tuta absoluta*), Onion thrips (*Thrips tabaci*), and Cotton bollworm (*Helicoverpa armigera*).

In some embodiments of the present disclosure, a suitable endonuclease includes a CRISPR-associated sequence 9 (Cas9) endonuclease or a variant thereof, a CRISPR-associated sequence 13 (Cas13) endonuclease or a variant thereof, CRISPR-associated sequence 6 (Cas6) endonuclease or a variant thereof, a CRISPR from *Prevotella* and *Francisella* 1 (Cpf1) endonuclease or a variant thereof, or a CRISPR from Microgenomates and Smithella 1 (Cms1) endonuclease or a variant thereof.

In some embodiments of the present disclosure, a suitable endonuclease includes a *Streptococcus pyogenes* Cas9 (SpCas9), a *Staphylococcus aureus* Cas9 (SaCas9), a *Francisella novicida* Cas9 (FnCas9), or a variant thereof. Variants may include a protospacer adjacent motif (PAM) SpCas9 (xCas9), high fidelity SpCas9 (SpCas9-HF1), a high fidelity SaCas9, or a high fidelity FnCas9.

In other embodiments of the present disclosure, the endonuclease comprises a Cas fusion nuclease comprising a Cas9 protein or a variant thereof fused with a FokI nuclease or variant thereof. Variants of the Cas9 protein of this fusion nuclease include a catalytically inactive Cas9 (e.g., dead Cas9).

In some embodiments of the present disclosure, the endonuclease may be a Cas9, Cas13, Cas6, Cpf1, CMS1 protein, or any variant thereof that is derived or expressed from *Methanococcus maripaludis* C7, *Corynebacterium diphtheria, Corynebacterium efficiens* YS-314, *Corynebacterium glutamicum* (ATCC 13032), *Corynebacterium glutamicum* (ATCC 13032), *Corynebacterium glutamicum* R, *Corynebacterium kroppenstedtii* (DSM 44385), *Mycobacterium abscessus* (ATCC 19977), *Nocardia farcinica* IFM10152, *Rhodococcus erythropolis* PR4, *Rhodococcus jostii* RHA1, *Rhodococcus opacus* B4 (uid36573), *Acidothermus cellulolyticus* 11B, *Arthrobacter chlorophenolicus* A6, *Kribbella flavida* (DSM 17836, uid43465), *Thermomonospora curvata* (DSM43183), *Bifidobacterium dentium* Bd1, *Bifidobacterium longum* DJO10A, *Slackia heliotrinireducens* (DSM 20476), *Persephonella marina* EX H1, *Bacteroides fragilis* NCTC 9434, *Capnocytophaga ochracea* (DSM 7271), *Flavobacterium psychrophilum* JIP02 86, *Akkermansia muciniphila* (ATCC BAA 835), *Roseiflexus castenholzii* (DSM 13941), *Roseiflexus* RS1, *Synechocystis* PCC6803, *Elusimicrobium minutum* Pei191, uncultured Termite group 1 bacterium phylotype Rs D17, *Fibrobacter succinogenes* S85, *Bacillus cereus* (ATCC 10987), *Listeria innocua, Lactobacillus casei, Lactobacillus rhamnosus* GG, *Lactobacillus salivarius* UCC118, *Streptococcus agalactiae*-5-A909, *Streptococcus agalactiae* NEM316, *Streptococcus agalactiae* 2603, *Streptococcus dysgalactiae equisimilis* GGS 124, *Streptococcus equi zooepidemicus* MGCS10565, *Streptococcus gallolyticus* UCN34 (uid46061), *Streptococcus gordonii* Challis subst CH1, *Streptococcus mutans* NN2025 (uid46353), *Streptococcus mutans, Streptococcus pyogenes* M1 GAS, *Streptococcus pyogenes* MGAS5005, *Streptococcus pyogenes* MGAS2096, *Streptococcus pyogenes* MGAS9429, *Streptococcus pyogenes* MGAS10270, *Streptococcus pyogenes* MGAS6180, *Streptococcus pyogenes* MGAS315, *Streptococcus pyogenes* SSI-1, *Streptococcus pyogenes* MGAS10750, *Streptococcus pyogenes* NZ131, *Streptococcus thermophiles* CNRZ1066, *Streptococcus thermophiles* LMD-9, *Streptococcus thermophiles* LMG 18311, *Clostridium botulinum* A3 Loch Maree, *Clostridium botulinum* B Eklund 17B, *Clostridium botulinum* Ba4 657, *Clostridium botulinum* F Langeland, *Clostridium cellulolyticum* H10, *Finegoldia magna* (ATCC 29328), *Eubacterium rectale* (ATCC 33656), *Mycoplasma gallisepticum, Mycoplasma mobile* 163K, *Mycoplasma penetrans, Mycoplasma synoviae* 53, *Streptobacillus moniliformis* (DSM 12112), *Bradyrhizobium* BTAi1, *Nitrobacter hamburgensis* X14, *Rhodopseudomonas palustris* BisB18, *Rhodopseudomonas palustris* BisB5, *Parvibaculum lavamentivorans* DS-1, *Dinoroseobacter shibae.* DFL 12, *Gluconacetobacter diazotrophicus* Pal 5 FAPERJ, *Gluconacetobacter diazotrophicus* Pal 5 JGI, *Azospirillum* B510 (uid46085), *Rhodospirillum*

*rubrum* (ATCC 11170), *Diaphorobacter* TPSY (uid29975), *Verminephrobacter eiseniae* EF01-2, *Neisseria meningitides* 053442, *Neisseria meningitides* alpha14, *Neisseria meningitides* Z2491, *Desulfovibrio salexigens* DSM 2638, *Campylobacter jejuni doylei* 269 97, *Campylobacter jejuni* 81116, *Campylobacter jejuni, Campylobacter lari* RM2100, *Helicobacter hepaticus, Wolinella succinogenes, Tolumonas auensis* DSM 9187, *Pseudoalteromonas atlantica* T6c, *Shewanella pealeana* (ATCC 700345), *Legionella pneumophila* Paris, *Actinobacillus succinogenes* 130Z, *Pasteurella multocida, Francisella tularensis novicida* U112, *Francisella tularensis holarctica, Francisella tularensis* FSC 198, *Francisella tularensis tularensis, Francisella tularensis* WY96-3418, or *Treponema denticola* (ATCC 35405).

With reference to FIGS. 4A-4C, the mating competitiveness of the sterile males produced using the pgSIT methods according to embodiments of the present disclosure, indicate that these sterile males are able to successfully mate and are able to successfully compete for female mates in the wild. Furthermore, with reference to FIGS. 4D-4E, the lifespan of the sterile males produced using the pgSIT methods according to embodiments of the present disclosure indicate that these sterile males have a lifespan (in total number of days) that is at least as long if not longer than the corresponding wild type males. Mating competitiveness and longevity are dominant factors in achieving local elimination, as once initial suppression or reduction has been achieved, larval resources are abundant and hence greater consumption by released immature forms is less impactful. Egg releases result in rapid population suppression or reduction from the outset, as hatching larvae consume resources that would otherwise be available to fertile larvae. Furthermore, pgSIT male sterile eggs according to embodiments of the present disclosure upon release in the wild may result in hatching larvae, as female lethality occurs during embryo/larval stages, resulting in maximum consumption of larval resources by released immature forms.

Additionally, the pgSIT methods as disclosed herein do not rely on chromosome translocations, chemosterilants, irradiation, antibiotics or bacterial infections, which can severely compromise the fitness and mating competitiveness of released sterile males.

With reference to FIGS. 4F-4K, using the MGDrivE simulation framework as described in Example 5 herein, simulated weekly releases of 200 pgSIT male sterile eggs per wild adult, indicate a wide range of parameter values for which local *Ae. aegypti* elimination is reliably achieved.

With reference to FIG. 5, methods for suppressing or reducing insect populations of insect species including disease vectors and agricultural pests include introducing male sterile eggs produced using the pgSIT methods of the present disclosure into an area in need of targeted insect suppression or reduction.

Some embodiments of the present disclosure include the development of a rearing facility to propagate homozygous endonuclease (e.g., Cas9) and dgRNA expressing strains separately. In some embodiments, an automated workflow is implemented to sex-sort immature stages (e.g. Cas9 females with dgRNA males) and combine into cages for maturation, mating and propagation of eggs. Sex sorting may be achieved in any number of suitable ways including mechanical size separation, automated copas sex sorting platform (Union Biometrica) combined with a genetic sexing strain, or automated robotic optical sorting. Suitable methods of sex sorting are discussed in Papathanos et al., Transgenic insects: techniques and applications 83-100, (October, 2014)

and Gilles et al., Acta Trop. 132, S178-S187 (2014), the entire contents of both of which are incorporated herein by reference.

In some embodiments, the pgSIT methods of producing sterile male eggs are particularly effective for the insect species with a diapause during the egg stage. Insects having a diapause during the egg stage, include, for example, *Ae. aegypti* and *Ae. albopictus*, as described in Diniz et al., Parasit. Vectors 10, 310 (2017), the entire content of which is incorporated herein by reference. This diapause would enable scalable egg accumulation for inundative releases. Accordingly, as depicted in general in FIG. 5, a single efficient pgSIT egg production facility may distribute pgSIT eggs to many remote field sites all over the world, where they can simply be hatched, reared, and released, eliminating or reducing the logistical burden of manual sex-sorting, sterilization, and releasing fragile adult males in each field location, thereby increasing scalability, and efficiency, enabling broader wide-scale population suppression or reduction capacity.

The following examples are presented for illustrative purposes only, and do not limit the scope or content of the present application.

EXAMPLES

Example 1. Binary CRISPR Induced Female Masculinization/Lethality, or Male Infertility To engineer pgSIT, single guide RNA (sgRNA) and spCas9 (Cas9 from hereon) expressing lines were generated in *Drosophila*. In total nine homozygous sgRNAs lines were developed to target genes essential for female viability, or genes important for male fertility. For female viability, these genes included sex-specific alternatively spliced sex-determination genes including sex lethal (Sxl, two separate transgenic lines—sgRNA$^{Sxl}$, sgRNA$^{Sxl-B}$), transformer (tra, two separate lines—sgRNA$^{Tra}$, sgRNA$^{Tra-B}$), or doublesex (dsxF, sgRNA$^{DsxF}$) as shown in FIGS. 1B-1C and described in Slee and Bownes, Q. Rev. Biol. 65, 175-204 (1990); Bell et al., Cell 65, 229-239 (1991); Boggs et al., Cell 50, 739-747 (1987), and Burtis and Baker, Cell 56, 997-1010 (1989), the entire contents of all of which are incorporated herein by reference. To disrupt male fertility, genes active during spermatogenesis were targeted, such as βTubulin 85D (βTub, sgRNA$^{βTub}$), fuzzy onions (fzo, sgRNA$^{Fzo}$) protamine A (ProtA, sgRNA$^{ProtA}$), or spermatocyte arrest (sa, sgRNA$^{Sa}$) as shown in FIG. 1C and described in Kemphues et al., Cell 21, 445-451 (1980), Hales and Fuller, Cell 90, 121-129 (1997), Kanippayoor et al., Spermatogenesis 3, e24376 (2013), and Lim et al., Spermatogenesis 2, 158-166 (2012), the entire contents of all of which are incorporated herein by reference. To promote robust Cas9 expression, three homozygous Cas9 expressing lines under control of two strong predominantly germ line specific promoters were established including nanos (nos-Cas9) or vasa (vas-Cas9) as described in Sano et al., Mech. Dev. 112, 129-139 (2002) and Doren et al., Curr. Biol. 8, 243-246 (1998), the entire content of both of which are incorporated herein by reference. In addition, the ubiquitous promoter Ubiquitin 63E (Ubi-Cas9)https://paperpile.com/c/cKXxhc/zEwAO as described in Akbari et al., BMC Cell Biol. 10, 8 (2009) and shown in FIG. 1D was established to enable robust expression in both somatic and germ line tissues during nearly all developmental life stages. A self-cleaving T2A peptide and eGFP coding sequence were inserted downstream (3') to the promoter-driven Cas9 together serving as a visual indicator of promoter activity as shown in FIGS. 1C-1D and described in Li et al., (2017). doi:10.1101/156778, the entire content of which is incorporated herein by reference.

To assess the genetic activity of the sgRNA lines, each strain was crossed to nos-Cas9, and the resulting trans-heterozygous $F_1$ progeny were analyzed. From these crosses, 4/9 of the sgRNAs, including sgRNA$^{Sxl}$, sgRNA$^{Tra}$, sg RNA$^{DsxF}$, sgRNA$^{\beta Tub}$, displayed expected phenotypes and were subjected to further characterization. To further evaluate these four sgRNAs, each of these selected four strains was bidirectionally crossed to wild type wt (replicate number of crosses between 10♀ and 10♀, N=24; progeny number, n=3519), or to homozygous nos-Cas9 (N=28, n=3628) as shown in FIG. 1F. With reference to FIGS. 1E-1F, the wt crosses did not produce significant gender ratio deviations or compromised fertility (N=30, n=4371). With continued reference to FIGS. 1E-1F, regardless of whether nos-Cas9 was maternally or paternally inherited, all $F_1$ trans-heterozygotes inheriting sgRNA$^{Sxl}$ were 100% male (N=7, n=540), and 100% of trans-heterozygous females inheriting sgRNA$^{Tra}$ or sgRNA$^{DsxF}$ were converted into sterile masculinized intersexes unable to oviposit eggs (N=14, n=942), and 100% of sgRNA$^{\beta Tub}$ trans-heterozygous males were sterile (N=7, n=517). These phenotypes were molecularly explored at the targeted genetic loci, and all sequenced flies (n=16) had mosaic insertions/deletions (indels) at the targeted loci as shown in FIG. 1G.

Example 2. Creation of Populations of Up to 100% Sterile Males

In some embodiments of the present disclosure, the disclosed pgSIT methodology may be used to disrupt genes essential for female viability and/or male sterility. In some embodiments, the disclosed pgSIT methodology may be used to concurrently or simultaneously disrupt genes essential for female viability and male sterility to genetically direct the majority or all (up to 100%) of surviving $F_1$ offspring to be sterile males. To achieve this directed sexing and sterility, three additional homozygous strains expressing multiplexed double gRNA (dgRNA) combinations, including dgRNA$^{\beta Tub,Sxl}$, dgRNA$^{\beta Tub,Tra}$ and dgRNA$^{\beta Tub,DsxF}$ were generated as shown in FIG. 1C. To genetically assess the activity of these pgSIT strains, each strain was bidirectionally crossed to wt or homozygous Cas9 (either nos-Cas9, vas-Cas9, or Ubi-Cas9). With reference to FIGS. 2A-2B, wt crosses produced no significant gender deviations or compromised fertility (N=36, n=5747). With continued reference to FIG. 2B, the crosses between dgRNA$^{\beta Tub,Sxl}$ with each Cas9 strain resulted in 100% female lethality due to disruption of sxl, in addition to 100% male sterility due to concurrent or simultaneous disruption of βTub (N=24, n=2521). Also, 100% of the females from the crosses between each Cas9 strain and dgRNA$^{\beta Tub,Tra}$ (N=24, n=1697) or dgRNA$^{\beta Tub,DsxF}$ (N=24, n=1791) were masculinized into sterile intersexes due to disruption of either tra or dsx, and 100% male offspring were sterile due to concurrent or simultaneous disruption of βTub (N=48, n=4231). Accordingly, with reference to FIGS. 2A-2C, the pgSIT methodology of the present disclosure renders highly active Cas9-gRNA complexes that are not saturated by dgRNAs and produce up to 100% sterile male adult offspring reproducibly and with unprecedented efficiency.

With respect to phenotypic analysis of the F1 progeny of the crosses of FIGS. 2A-2C, 100% of the dgRNA$^{\beta Tub,Sxl}$ knockout females perished during pre-adult stages with the majority dying during pupal transition as shown in FIGS. 2D-2E. For intersex phenotypes, fertility was always compromised, however as shown in FIGS. 2C and 2F, variable expressivity was observed as the extent of anatomical masculinization varied between individuals and was more pronounced in the dgRNA$^{\beta Tub,Tra}$ knockouts as compared to the dgRNA$^{\beta Tub,DsxF}$. For example, with reference to FIGS. 2F and 2H, dgRNA$^{\beta Tub,Tra}$ knockout intersexes had sexcombs with variable bristle numbers and rarely developed more than one rudimentary ovary. In addition, with reference to FIG. 2I, molecularly the dgRNA$^{\beta Tub,Tra}$ knockout intersexes expressed both female and male-specific alternative splice variants of dsx gene, presumably due to the absence of Tra which is important for inhibiting the male-specific and promoting the female-specific alternative splicing of dsx as described in Nagoshi et al., Cell 53, 229-236 (1988), the entire content of which is incorporated herein by reference. In contrast, with reference to FIGS. 2C, 2F, and 2J, the dgRNA$^{\beta Tub,DsxF}$ knockout intersexes were not observed to develop sexcombs, and some instersexes had normal ovaries enabling them to become gravid, although unable to oviposit.

In order to analyze male infertility phenotypes, the anatomy of testes and developing spermatids in the $F_1$ sterile males was visualized using a generated transgenic line expressing eGFP under control from the βTub85D-promoter (βTub-GFP) to fluorescently label the testes and sperm as depicted in FIG. 1C. was introgressed with the dgRNA strains. With reference to FIG. 2K, when introgressed with homozygous nos-Cas9, the trans-heterozygous dgRNA$^{\beta Tub,Sxl}$/+; βTub-GFP/nos-Cas9 $F_1$ sterile males showed fully developed coiled testes (ts) and accessory glands (ag). However, spermatid development in these $F_1$ sterile males was completely disrupted with phenotypes consistent with previous βTub disruption reports as described in Kemphues et al., Cell 21, 445-451 (1980), the entire contents of which are herein incorporated by reference. For example, with reference to FIG. 2L, only round cysts and early spermatocytes were identified in the testes (ts) of sterile males marked with GFP, while with reference to FIG. 2M, wt testes (ts) had robust GFP-labeled cysts with elongated late spermatids. With reference to FIG. 2F, although no GFP-positive testes were identified in either dgRNA$^{\beta Tub,Tra}$ or gRNA$^{\beta Tub,DsxF}$ knockout intersexes (n>20), paired putative male accessory gland like organs were present in both intersex types as shown in FIGS. 2H, 2J, and 2K. To confirm the molecular changes that resulted in knockout phenotypes, both of the targeted loci from individual $F_1$ flies were sequenced. With reference to FIGS. 1G and 2N-2Q, compared to the control flies (n=32), each examined double knockout fly (n=20) had mosaic indels precisely at the cleavage sites that prevented sequencing through both ends of PCR amplicons.

Example 3. Complete Penetrance Resulting From Zygotic Expression

Maternal deposition of Cas9/gRNA complexes into developing embryos is sufficient to ensure non-Mendelian inheritance of mutations in receiving progeny, even if those progeny do not genetically inherit the genes encoding the editing components. This phenomenon is known as dominant maternal effect, as described in Lin and Potter, G3 (2016) doi:10.1534/g3.116.034884, the entire content of which is incorporated herein by reference. In this regard, paternal inheritance of one of the core components (e.g., Cas9 or dgRNA), combined with maternal deposition of the compatible component was investigated to determine if either would be sufficient to generate heritable mutations. With reference to FIGS. 1G and 3B, matings between homozygous Cas9 fathers and heterozygous dgRNA expressing mothers were not sufficient to induce mutations (n=12), or knockout phenotypes (N=6, n=252), in $F_1$ progeny that did not inherit the dgRNAs as a gene. Without being bound by any particular mechanism or theory, this result may be caused by a result of a short dgRNA half-life in the absence of Cas9 during maternal deposition. With reference to FIGS. 3A and 3C, matings between heterozygous Cas9 fathers and homozygous dgRNA-expressing mothers resulted in male sterility and female lethality/masculinization phenotypes in all trans-heterozygous $F_1$ progeny that inherited the Cas9 gene (N=27, n=2191), while all $F_1$ progeny that inherited only the dgRNA-encoding genes maintained normal features (N=27, n=2640). With continued reference to FIGS. 3A and 3C, crosses between heterozygous Cas9 mothers and homozygous dgRNA-expressing fathers resulted in male sterility and female lethality/masculinization phenotypes in all trans-heterozygous $F_1$ progeny (N=36, n=3019). Additionally, with reference to FIG. 3A, maternal contribution of Cas9 protein was sufficient to induce intersex phenotypes in progeny that did not receive the Cas9 gene when targeting tra or dsx (N=24, n=782), demonstrating a dominant maternal effect. However, with reference to FIGS. 3A-3B, maternal contribution of Cas9 only by Ubi-Cas9 (N=4; n=0, number of surviving females), but not nos-Cas9 nor vas-Cas9 (N=8, n=556), induced dgRNA$^{\beta Tub, Sxl}$/+; +/+ female lethality indicating that promoter strength may affect mutation efficiency. With reference to FIGS. 1G and 3B, despite the lack of lethality phenotypes in females receiving Cas9 protein maternally loaded from nos-Cas9 and receiving the dgRNA$^{\beta Tub, Sxl}$ gene, these surviving females had mosaic indels at the Sxl locus (n=2). Similarly, with reference to FIGS. 1G and 3A-3B, all male progeny that inherited only the dgRNA genes (N=36, n=1490), and had maternally loaded Cas9 protein, were fertile for all indicated Cas9 strains, though each genotyped male (n=6) had mosaic indels at the βTub locus. According to some embodiments of the present disclosure, as depicted in FIG. 3D, paternal inheritance of a guide polynucleotide (e.g., a gRNA) along with maternal deposition of the endonuclease (e.g., Cas9) into developing embryos, in the absence of Cas9 inherited as a gene, is sufficient to induce detectable biallelic mosaicism.

Example 4. pgSIT Males Sexually Compete for Mates and their Survival is not Reduced With reference to FIG. 4A, in order to assess the overall and mating fitness of pgSIT males having precise knockouts of single genes required for female-specific viability and spermatid maturation, a mating competition assay was implemented and estimated survival curves were calculated. With reference to FIGS. 4B-4C, pgSIT-generated males were able to court, mate, and successfully compete with wt males. With continued reference to FIGS. 4B-4C, the observed reduced egg hatch rate of 47.9%±13.8% for one wt together with one pgSIT males vs. 85.1%±13.5% for two wt males (N=5, P>0.003) or 87.6%±7.2% for one wt male (N=5, P>0.001) was consistent with a mating competitiveness of 78% for pgSIT males relative to wt males. With reference to FIG. 4D, longevity (e.g., lifespan) was not compromised in pgSIT males as compared to wt males. Furthermore, as Lin and Potter, G3 (2016) doi:10.1534/g3.116.034884, reported that maternally deposited Cas9 is known to affect progeny phenotype, two types of pgSIT males—one with inherited paternal Cas9 and the other maternal Cas9—were considered separately. With reference to FIGS. 4D-4E, the median survival time for wt males was estimated as 32.3±1.3 days (N=5, n=275) while the median survival times of pgSIT males were 52.7±1.6 (N=5, n=220) and 53.7±0.9 days (N=5, n=275) for males carrying paternal Cas9 and maternal Cas9, respectively. With reference to FIG. 4D, both of these Cas9 pgSIT males survived significantly longer than wt males (P<2.2$^{-16}$), while no significant difference was identified between the lifespan (survival times measured in days) for these two types of pgSIT males. Considering different median survival times were reported for *Drosophila* wild type males, for example, 35.5 days (reported in Tatar et al., Science 292, 107-110 (2001) and 57 days (reported in Clancy et al., Science 292, 104-106 (2001) and Lin et al., Science 282, 943-946 (1998), breeding conditions, such as food composition, temperature, etc., are known to affect survival time. As the median survival time of pgSIT males is comparable to the longer survival time reported for wt males and the pgSIT males show a mating competitiveness of 78%, neither the survival (e.g., lifespan) nor the mating competitiveness is compromised in the genetically engineered pgSIT male insects produced according to methods of the present disclosure.

Example 5. pgSIT's Potential to Suppress or Reduce Mosquito Populations Surpasses that of Current Methods To assess how the pgSIT methodologies of the present disclosure compare to currently-available self-limiting suppression or reduction technologies (e.g., RIDL, fsRIDL and IIT), release schemes were simulated for each of these technologies using the MGDrivE simulation framework as disclosed in Sanchez et al., (2018), doi:10.1101/350488, the entire content of which is incorporated herein by reference. This simulation framework models the egg, larval, pupal, and adult mosquito life stages with overlapping generations, larval mortality increasing with larval density, and a mating structure in which females retain the genetic material of the adult male with whom they mate for the duration of their adult lifespan. With reference to the table in FIG. 4F, the simulation framework was programmed for releases into a randomly-mixing population consisting of 10,000 adult female mosquitoes, with model and intervention parameters as indicated.

With reference to FIGS. 4F-4G, weekly releases of adult males were simulated for RIDL and IIT and eggs were simulated or fsRIDL and pgSIT over a 6 month period. Adult release ratios were 10 adult RIDL/IIT males per wild adult, following the precedent of a field trial of *Ae. aegypti* RIDL mosquitoes in Brazil as disclosed in Carvalho et al., (2015) (supra), and egg release ratios were 200 eggs per wild adult, given that female *Aedes* (*Ae*) *aegypti* produce approximately 20 eggs per day in temperate climates as disclosed in Otero et al., 2006 (supra). Results from these simulations suggest that systems for which eggs are released (e.g., pgSIT and fsRIDL) result in the most rapid population suppression or reduction in the first three weeks as released eggs quickly hatch as larvae and reduce the survival of fertile larvae as a consequence of density-dependent larval competition. The pgSIT approach shows the greatest suppression or reduction from the end of the first month on, and the greatest potential to eliminate the population during the release period. This is due to the higher mating competitiveness of pgSIT males (78% that of wt males) c.f. fsRIDL males (approximately 5% that of wt males, based on RIDL field trials in the Cayman Islands and Brazil) (Harris et al., 2011 and Carvalho et al., 2015, respectively) (supra), which becomes a dominant factor at low population densities when greater consumption of larval resources by released immature forms has less impact on suppression or reduction. Population suppression or reduction resulting from 10:1 releases of adult RIDL males trails that for releases of fsRIDL eggs by 2 to 3 weeks due to the delay in impact on density-dependent larval competition; but is similar in magnitude. Equivalent releases of adult IIT males are less impactful for the simulated strategy because male incompatibility is induced through *Wolbachia* infection and the chance of an unintended release of *Wolbachia*-infected females interfering with suppression or reduction is reduced through low-level irradiation as reported in Zhang et al., 2015[1] and Zhang et al., 2015[2] (supra), resulting in the longevity of released IIT males being roughly halved as reported in Yamada et al., 2014 (supra).

Example 6. Materials and Methods

CRISPR target site design. To confer female lethality and male sterility, target sites for guide RNAs (gRNAs) were chosen inside female-specific exons of sex-determination genes, Sex Lethal (Sxl), Transformer (tra), and Doublesex (dsx), and in male specific genes, βTubulin 85D (βTub), fuzzy onions (fzo), Protamine A (ProA), and spermatocyte arrest (sa), respectively. CHOPCHOP v2 (as disclosed in Labun et al., Nucleic Acids Res. 44, W272-6 (2016), the entire content of which is incorporated herein by reference) was used for choosing gRNA target sites from specified sequence in *Drosophila* genome (dm6) to minimize the off-target cleavage. Due to the alternative splicing, functional Sxl and Tra proteins are produced only in *Drosophila* females, while two versions of Dsx protein-female (Dsx$^F$) or male (Dsx$^M$)—are made each in the corresponding gender as depicted in FIG. 1B. The gRNA target for βTub was chosen in the vicinity to the βTub85D$^D$ (B2t$^D$) mutant allele as reported in Kemphues et al., Cell 21, 445-451 (1980) (supra). Sequences of gRNA target sites are presented in FIG. 1C.

Design and assembly of constructs. Gibson enzymatic assembly method was used to build all constructs as disclosed in Gibson et al., Nat. Methods 6, 343-345 (2009), the entire content of which is incorporated by reference. The previously described plasmid harboring the SpCas9-T2A-GFP with nuclear localization signals (NLS) flanking SpCas9 coding sequence and the Opie2-dsRed transformation marker was used to build *Drosophila* Cas9 constructs used herein. This plasmid was used for *Ae. aegypti* transgenesis and had both piggyBac and an attB-docking sites (Addgene #100608), as disclosed in Li et al., (2017) doi: 10.1101/156778. The *Ae. aegypti* promoter was removed from the plasmid by cutting at NotI & XhoI sites and replacing it with Nanos (nos), or Ubiquitin-63E (Ubi), or Vasa (vas) promoter as shown schematically in FIG. 1C. Promoter fragments were PCR amplified from *Drosophila* genomic DNA using the following primers: nos-F, nos-R, Ubi-F, Ubi-R, vas-F, and vas-F. To generate constructs with a single gRNA, *Drosophila* U6-3 promoter and guide RNA with a target, scaffold, and terminator signal (gRNA) was cloned at the multiple cloning site (MCS) between the white gene and an attB-docking site inside a plasmid used for *D. melanogaster* transformation as described in Akbari et al., Curr. Biol. 23, 671-677 (2013), the entire content of which is incorporated by reference. For the first plasmid in this series, U6-3-gRNA$^{βTub}$, *Drosophila* U6-3 promoter was amplified from *Drosophila* genomic DNA with U6-1F and U6-2R primers while the complete gRNA was PCR-assembled from two Ultramer® gRNA-3F and gRNA-4R oligos synthesized by Integrated DNA Technology (IDT). To improve the efficiency of termination of gRNA transcription, a termination signal with 11 thymines was used in our design. In the successive plasmids, the U6-3 promoter and gRNA's scaffold was amplified from the U6-3-gRNA$^{βTub}$ plasmid using the overlapping middle oligos designed to replace 20 bases that constitute a gRNA target (U6-1AF, U6-2A/B/CR, gRNA-3A/B/CF, and gRNA-4AR), and replaced by digesting the same plasmid at AscI and NotI sites. To assemble the set of plasmids with double gRNAs (dsRNAs), the U6-3 promoter and gRNA was amplified as one fragment from the single gRNA (sgRNA) plasmids targeting female sex-determination genes with 2×gRNA-5F and 2×gRNA-6R primers, and cloned inside the U6-3-gRNA$^{βTub}$ plasmid that was linearized at a BamHI site between the white gene and the U6-3 promoter. Each dgRNA plasmid had the same gRNAβTub targeting βTub85D and a different gRNA targeting Sxl, tra, or dsxF expressed independently in the same direction as depicted in FIG. 1C. With reference to FIG. 1C, *Drosophila* Cas9 plasmids and gRNA plasmids generated for this study were deposited at Addgene. To build the βTub85D-GFP construct, a 481 bp fragment directly upstream of βTub coding sequence was PCR amplified from *Drosophila* genomic DNA with βTub-F and βTub-R primers and cloned upstream of GFP into the white attB-docking site plasmid described above.

Fly genetics and imaging. Flies were maintained under standard conditions at 25° C. Embryo injections were carried at Rainbow Transgenic Flies, Inc. (http://www.rainbow-gene.com). With reference to FIG. 1C, the Cas9 and gRNA constructs were inserted at the PBac{y+-attP-3B}KV00033 on the 3rd chromosome (Bloomington #9750) and the P{CaryP}attP1 on the 2nd chromosome (Bloomington #9750), respectively; while βTub-GFP construct was inserted at the M {3XP3-RFP.attP'}ZH-86Fa on the 3rd chromosome (Bloomington #24486). Transgenic flies were balanced with w1118; CyO/snaSco and w$^{1118}$; TM3, Sb$^1$/TM6B, Tb$^1$; and double balanced with w1118; CyO/Sp; Dr$^1$/TM6C, Sb, Tb$^1$. The βTub-GFP (on the 3rd chromosome) was double balanced and introgressed with gRNAβTub,Sxl gRNAβTub, Tra, and gRNA$^{βTub}$, Dsx$^F$, each on the 2nd chromosome, to generate trans-heterozygous balanced stocks (dgRNA/CyO; βTub-GFP/TM6C, Sb, Tb).

To test the efficiency of knockouts and corresponding phenotypes caused by sgRNAs, seven flies of each gender were crossed to generate trans-heterozygous F1 sgRNA/+; nos-Cas9/+ flies for each combination of sgRNA; and their external morphology and fertility were examined. Both transgenes were identified on a fluorescent stereo microscope with w+ eyes (sgRNA, dgRNA) and dsRed (Cas9). The sgRNA lines that caused knockout phenotypes were further tested as homozygous stocks with nos-Cas9 flies in both directions using 10♂ and 10♀ flies for each replicate cross. DgRNAs lines were tested bidirectionally with homozygous nos-Cas9, vas-Cas9, and Ubi-Cas9 lines. In addition, sgRNA, dgRNA and Cas9 homozygous lines were crossed to w− flies in both directions to provide the comparison control. To test for the non-Mendelian dominant maternal effect of Cas9 loaded as protein into embryos as disclosed in Lin and Potter, G3 (2016) doi: 10.1534/g3.116.034884, homozygous dgRNA flies were crossed to heterozygous Cas9 flies; and phenotypes of dgRNA/+;

+/TM3, Sb progeny with either maternal Cas9 or paternal Cas9 were compared. The F1 progeny from crosses with the paternal Cas9 served as a control group to examine the dominant maternal effect of Cas9. To test fertility of generated knockout flies with and without the Cas9 gene, batches of 10-20 F1 males and females, or intersexes, were crossed to 15-20 female virgin and male flies, correspondingly, from w− and/or Cantos S stocks. Three or four days after the cross, the flies were passaged into fresh vials, and in a week, both vials were examined for presence of any viable progeny. The fertility of an entire batch was scored as 100% when viable larvae were identified in a vial, or 0% when no progeny hatched in both vials. The vials containing intersexes and wt males were also examined for presence of laid eggs. All crosses were repeated at the minimum three times to generate means and standard deviations for statistical comparisons and thus measure consistency and robustness of the results.

Flies were scored, examined, and imaged on the Leica M165FC fluorescent stereo microscope equipped with the Leica DMC2900 camera. To generate images of adult flies, image stacks collected at different focal plates were compiled into single images in Helios Focus 6, and then edited in Adobe Photoshop CS6. To study internal anatomical features of intersex flies and sterile males, their reproductive organs were dissected in PBS buffer, examined, and imaged. To estimate the variation of knockout phenotypes, around 10-20 flies were dissected for each tested genotype.

Developmental stage of Sxl lethality. To identify the developmental stage at which Sxl knockout females die, egg hatching and larval death rates were quantified for the $dgRNA^{\beta Tub,sxl}/+$; nos-Cas9/+ trans-heterozygous flies. To quantify the egg hatching rate, three replicate crosses, each with 20-30 homozygous nos-Cas9 female virgins and 10-20 $dgRNA^{\beta Tub,Sxl}$ males, were set up in embryo collection cages (Genesee Scientific 59-100) with grape juice agar plates. Three embryo collection cages with w− flies served as a comparison control. Batches of around 200 laid eggs were counted from each collection cage and followed for over 36 hours to count the number of unhatched eggs. To quantify the rate of larval death, two batches of 50 emerged larvae were transferred from each agar plate to separate fly vials with food and raised to adults, then a number and sex of emerged adults were recorded. To quantify the lethality at a pupal stage, a number of dead pupae was also recorded for each vial.

RT-PCR of female- and male-specific splice transcripts of Dsx. To assess the effect of tra knockout on dsx splicing, we screened for female- and male-specific mRNA of dsx in tra knockout intersexes. Total RNA were extracted from adult w− male, w− female, and tra knockout ($dgRNA^{\beta Tub,Tra}/+$; nos-Cas9/+) intersex flies following the standard protocol of the MirVana miRNA isolation kit (Ambion). To remove DNA contamination, 2 µg was treated with TURBO™ DNase using the TURBO DNA-Free™ Kit (Ambion). Dsx female and male splice variants were amplified with the SuperScript® III One-Step RT-PCR Kit (Invitrogen) following the protocol. The same forward primer, Dsx-RT-1F, and two different reverse primers, DsxF-RT-2R and DsxM-RT-3R were used to amplify either female or male transcripts, respectively. 10 µL of PCR products were run on a 1% agarose gel to test PCR specificity, and the remaining 40 µL were purified using a QIAquick PCR purification kit (QIA-GEN) or, when double bands were identified on a gel, gel-purified with a Zymoclean™ Gel DNA Recovery Kit (Zymo Research), then clean amplicons were sequenced in both directions using Sanger method at Source BioScience (https://www.sourcebioscience.com).

Genotyping loci targeted with gRNAs. To examine the molecular changes that caused female lethality or masculinization and male sterility in the flies carrying Cas9 and gRNAs, four genomic loci that include targets sites for four functional gRNAs (FIG. 1C) were amplified and sequenced. Single-fly genomic DNA preps were prepared by homogenizing a fly in 30 µl of a freshly prepared squishing buffer (10 mM Tris-CI pH 8.0, 1 mM EDTA, 25 mM NaCL, 200 µg/mL Proteinase K), incubating at 37° C. for 35 minutes, and heating at 95° C. for 2 minutes. 2 µl of genomic DNA was used as template in a 40 µL PCR reaction with LongAmp® Taq DNA Polymerase (NEB). The following primers were used to amplify the loci with the corresponding gRNA targets: βTub-1AF and βTub-2AR for βTubulin 85D; Sxl-3BF and Sxl-4AR for Sex lethal; Tra-5F and Tra-6R for Transformer, Dsx-7F and Dsx-8R for Double sex. PCR products were purified using a QIAquick PCR purification kit (QIAGEN), and sequenced in both directions with Sanger method at Source BioScience. To characterize molecular changes at the targeted sites, sequence AB1 files were aligned against the corresponding reference sequences in SnapGene® 4 and/or Sequencher™ 5.

Competition assay of sterile males. To evaluate the competitiveness of the βTub knockout ($gRNA^{\beta Tub,Sxl}/+$; nos-Cas9/+) males, their ability to secure matings with females in the presence of wt males was evaluated. The w− males share the same genetic background with the βTub knockout males, and provide an ideal comparison. Two wt, one wt, one wt plus one βTub knockout, or two βTub knockout males were placed into a fly vial with ten w− virgins isolated on yeast paste for two days and allowed to court and mate with the females overnight (12 hours) in the dark. To increase the male courtship drive, freshly emerged $dgRNA^{\beta Tub,Sxl}/+$; nos-Cas9/+ and wt males were isolated from females and aged for four days before the competition assay. *Drosophila* females mate with multiple males during a lifespan; and in the absence of sperm transferred to spermatheca after copulation, female abstinence lasts for one day postcopulation, as disclosed in Peng et al., Curr. Biol. 15, 207-213 (2005), the entire content of which is incorporated herein by reference. Therefore, after 12 hours of mating, all males were removed from the vials while the females were transferred into small embryo collection cages (Genesee Scientific 59-100) with grape juice agar plates. Three batches of eggs were collected within 36 hours and unhatched eggs were counted. The decrease in fertility, estimated by a number of unhatched eggs, indicated the ability of a $gRNA^{\beta Tub,\ Sxl}/+$; nos-Cas9/+ male to score successful matings with females in the presence of a wt male; and thus provided a readout of the competitiveness of βTub knockout males. A single wt male was used to test its ability to inseminate each of ten females in 12 hours, and thus discriminate between a true competition or a dilution effect of two wt males.

Survival curves to estimate longevity of pgSIT males. To compare differences in survival between pgSIT ($gRNA^{\beta Tub,\ Sxl}/+$; nos-Cas9/+) and wt males, average longevities for three experimental groups of males were estimated. Two types of pgSIT flies were treated as separate experimental groups—one carrying paternal Cas9 and the other maternal Cas9. Five replicates per each of three groups were applied to estimate survival curves. Males of each type were collected daily and aged in batches of 20 males per vial. Each replicate had from 40 to 75 males kept in 2 or 4 vials, respectively. Numbers of dead flies were recorded every third day during the transfer of flies into a new vial with fresh food. The interval censored time to event (e.g., death) data was analyzed for the three experimental groups by computing non-parametric maximum likelihood estimates (NPMLE) of the survival curves for each group, implemented in the R package "interval" as described in Fay et al., J. Stat. Softw. 36, (2010), the entire content of which is incorporated herein by reference. The estimation procedure takes into account uncertainty introduced by the three-day observation period. A bootstrap with 10,000 repetitions was applied to quantify median survival time and standard deviation.

Mathematical modelling. To model the expected performance of pgSIT at suppressing or reducing local *Ae. aegypti* populations in comparison to currently-available self-limiting suppression or reduction technologies—RIDL, fsRIDL and IIT-\release schemes were simulated for each using the MGDrivE simulation framework as disclosed in Sanchez et al., 2018, doi: 10.1101/350488 (https://marshalllab.github.io/MGDrivE/), the entire content of which is incorporated herein by reference. This framework models the egg, larval, pupal and adult mosquito life stages (both male and female adults are modeled) implementing a daily time step, overlapping generations and a mating structure in which adult males mate throughout their lifetime, while adult females mate once upon emergence, retaining the genetic material of the adult male with whom they mate for the duration of their adult lifespan. Density-independent mortality rates for the juvenile life stages are assumed to be identical and are chosen for consistency with the population growth rate in the absence of density-dependent mortality. Additional density-dependent mortality occurs at the larval stage, the form of which is taken from Deredec et al. Proc. Natl. Acad. Sci. U.S.A. 108, E874-80 (2011), the entire content of which is incorporated herein by reference. The inheritance patterns for the pgSIT, RIDL, fsRIDL and IIT systems are modeled within the inheritance module of the MGDrivE framework https://paperpile.com/c/cKXxhc/fx0P6 as described in Sanchez et al., 2018, doi: 10.1101/350488, along with their impacts on adult lifespan, male mating competitiveness and pupatory success. The stochastic version of the MGDrivE framework was implemented to capture the random effects at low population sizes and the potential for population elimination. Weekly releases were simulated over a period of 6 months into a randomly-mixing population consisting of 10,000 adult females at equilibrium, with *Ae. aegypti* life history and intervention parameter values listed in the table in FIG. 4F.

Statistical analysis. Statistical analysis was performed in JMP 8.0.2 by SAS Institute Inc. Three to five biological replicates were used to generate statistical means for comparisons. P values were calculated for a two-sample Student's t-test with unequal variance. To test for significance of male sterilization, Pearson's Chi-squared tests for contingency tables were used to calculate P values. To test for differences between the inferred survival curves we used Sun's generalization of the log-rank test as described in Sun, Stat. Med. 15, 1387-1395 (1996), the entire content of which is incorporated herein by reference. In addition, we performed pairwise post-hoc tests of differences between the two pgSIT groups with conservative Bonferroni correction.

Deposited Data. Complete annotated plasmid sequences and plasmid DNA are publically available for order at Addgene. Transgenic flies have been made available for order from Bloomington *Drosophila* stock center.

While the present disclosure has been illustrated and described with reference to certain exemplary embodiments, those of ordinary skill in the art will understand that various modifications and changes may be made to the described embodiments without departing from the spirit and scope of the present disclosure, as defined in the following claims.

What is claimed is:

1. A method of directing male sexing in a progeny of genetically modified insects, the method comprising:
   (a) providing a first insect strain, wherein the first insect strain has integrated into its genome:
      (i) at least one nucleic acid sequence comprising at least one first guide polynucleotide targeting a female-essential genomic sequence that is required for female-specific viability of the first insect strain, wherein the female-essential genomic sequence is a gene or a splice-variant of a gene selected from the group consisting of sex lethal (Sxl), transformer (Tra), and doublesex (Dsx), and
      (ii) at least one nucleic acid sequence comprising at least one second guide polynucleotide targeting a male sterility genomic sequence that is required for male-specific fertility of the first insect strain, wherein the male sterility genomic sequence is a βTubulin 85D (βTub) gene;
   (b) providing a second insect strain, wherein the second insect strain has integrated into its genome a nucleic acid sequence encoding an endonuclease, and wherein:
      the first insect strain and the second insect strain are the same insect species, and
      the endonuclease is directed by the first and second guide polynucleotides to enzymatically knock-out the female-essential genomic sequence and the male sterility genomic sequence, respectively, when present in the same insect; and
   (c) genetically crossing the first insect strain and the second insect strain, thereby producing a progeny of genetically modified insects comprising the endonuclease and the at least one nucleic acid sequence, wherein the progeny comprises sterile male insect eggs or sterile male insects.

2. The method of claim 1, wherein the progeny of genetically modified insects produced in (c) comprises sterile male insect eggs.

3. The method of claim 1, wherein the nucleic acid sequences comprising the at least first and second guide polynucleotides are integrated into the genome of the first insect strain by homozygous integration into all chromosome copies in the genome.

4. The method of claim 1, wherein the nucleic acid sequences comprising the at least first and second guide polynucleotides are introduced into the first insect during an embryonic stage.

5. The method of claim 1, wherein the at least one first guide polynucleotide and the at least one second guide polynucleotide each comprise at least one guide ribonucleic acid (gRNA).

6. The method of claim 1, wherein the at least one first guide polynucleotide comprises more than one first guide polynucleotide, each of which targets a different region of the same female-essential genomic sequence that is required for female-specific viability.

7. The method of claim 1, wherein the at least one first guide polynucleotide comprises more than one first guide polynucleotide, each of which targets a different female-essential genomic sequence that is required for female-specific viability.

8. The method of claim 1, wherein the at least one first guide polynucleotide comprises more than one first guide polynucleotide, each of which targets a different gene selected from the group consisting of: sex lethal (Sxl), transformer (Tra), and doublesex (Dsx).

9. The method of claim 8, wherein the more than one first guide polynucleotide comprises two first guide polynucleotides, each of which targets a different gene selected from the group consisting of: Sxl, Tra, and Dsx.

10. The method of claim 8, wherein the more than one first guide polynucleotide comprises two first guide polynucleotides, each of which targets a different gene selected from the group consisting of: Sxl and Dsx.

11. The method of claim 1, wherein:

when the second insect is a male, the nucleic acid sequence encoding the endonuclease is integrated into the genome of the second insect by homozygously integrating a gene encoding the endonuclease, and when the second insect is a female, the nucleic acid sequence encoding the endonuclease is integrated into the genome of the second insect by homozygously or heterozygously integrating a gene encoding the endonuclease or by depositing an endonuclease protein into the second insect.

12. The method of claim 1, wherein the nucleic acid sequence encoding the endonuclease is integrated into the genome of the second insect during an embryonic stage.

13. The method of claim 1, wherein the endonuclease comprises:

a CRISPR-associated sequence 9 (Cas9) endonuclease or a variant thereof, a CRISPR-associated sequence 13 (Cas13) endonuclease or a variant thereof, CRISPR-associated sequence 6 (Cas6) endonuclease or a variant thereof, a CRISPR from *Prevotella* and *Francisella* 1 (Cpf1) endonuclease or a variant thereof, or a CRISPR from Microgenomates and Smithella 1 (Cms1) endonuclease, or a variant thereof;

a *Streptococcus pyogenes* Cas9 (SpCas9), a *Staphylococcus aureus* Cas9 (SaCas9), a *Francisella novicida* Cas9 (FnCas9), or a variant thereof;

a Cas fusion nuclease comprising a Cas9 protein or a variant thereof fused with a FokI nuclease or variant thereof; or a Cas9, Cas13, Cas6, Cpf1, Cms1 protein or any variant thereof derived from *Methanococcus maripaludis* C7, *Corynebacterium diphtheria, Corynebacterium efficiens* YS-314, *Corynebacterium glutamicum* (ATCC 13032), *Corynebacterium glutamicum* (ATCC 13032), *Corynebacterium glutamicum* R, *Corynebacterium kroppenstedtii* (DSM 44385), *Mycobacterium abscessus* (ATCC 19977), *Nocardia farcinica* IFM10152, *Rhodococcus erythropolis* PR4, *Rhodococcus jostii* RHA1, *Rhodococcus opacus* B4 (uid36573), *Acidothermus cellulolyticus* 11B, *Arthrobacter chlorophenolicus* A6, *Kribbella flavida* (DSM 17836, uid43465), *Thermomonospora curvata* (DSM43183), *Bifidobacterium dentium* Bd1, *Bifidobacterium longum* DJO10A, *Slackia heliotrinireducens* (DSM 20476), *Persephonella marina* EX H1, *Bacteroides fragilis* NCTC 9434, *Capnocytophaga ochracea* (DSM 7271), *Flavobacterium psychrophilum* JIP02 86, *Akkermansia muciniphila* (ATCC BAA 835), *Roseiflexus castenholzii* (DSM 13941), *Roseiflexus* RS1, *Synechocystis* PCC6803, *Elusimicrobium minutum* Pei191, uncultured Termite group 1 bacterium phylotype Rs D17, *Fibrobacter succinogenes* S85, *Bacillus cereus* (ATCC 10987), *Listeria innocua, Lactobacillus casei, Lacto-*

*bacillus rhamnosus* GG, *Lactobacillus salivarius* UCC118, *Streptococcus agalactiae*-5-A909, *Streptococcus agalactiae* NEM316, *Streptococcus agalactiae* 2603, *Streptococcus dysgalactiae equisimilis* GGS 124, *Streptococcus equi zooepidemicus* MGCS10565, *Streptococcus gallolyticus* UCN34 (uid46061), *Streptococcus gordonii* Challis subst CH1, *Streptococcus mutans* NN2025 (uid46353), *Streptococcus mutans, Streptococcus pyogenes* M1 GAS, *Streptococcus pyogenes* MGAS5005, *Streptococcus pyogenes* MGAS2096, *Streptococcus pyogenes* MGAS9429, *Streptococcus pyogenes* MGAS10270, *Streptococcus pyogenes* MGAS6180, *Streptococcus pyogenes* MGAS315, *Streptococcus pyogenes* SSI-1, *Streptococcus pyogenes* MGAS10750, *Streptococcus pyogenes* NZ131, *Streptococcus* thermophiles CNRZ1066, *Streptococcus* thermophiles LMD-9, *Streptococcus* thermophiles LMG 18311, *Clostridium botulinum* A3 Loch Maree, *Clostridium botulinum* B Eklund 17B, *Clostridium botulinum* Ba4 657, *Clostridium botulinum* F Langeland, *Clostridium cellulolyticum* H10, *Finegoldia magna* (ATCC 29328), *Eubacterium rectale* (ATCC 33656), *Mycoplasma gallisepticum, Mycoplasma mobile* 163K, *Mycoplasma penetrans, Mycoplasma synoviae* 53, *Streptobacillus moniliformis* (DSM 12112), *Bradyrhizobium* BTAi1, *Nitrobacter hamburgensis* X14, *Rhodopseudomonas palustris* BisB18, *Rhodopseudomonas palustris* BisB5, *Parvibaculum lavamentivorans* DS-1, *Dinoroseobacter shibae*. DFL 12, *Gluconacetobacter diazotrophicus* Pal 5 FAPERJ, *Gluconacetobacter diazotrophicus* Pal 5 JGI, *Azospirillum* B510 (uid46085), *Rhodospirillum rubrum* (ATCC 11170), *Diaphorobacter* TPSY (uid29975), *Verminephrobacter eiseniae* EF01-2, *Neisseria meningitides* 053442, *Neisseria meningitides* alpha14, *Neisseria meningitides* Z2491, *Desulfovibrio salexigens* DSM 2638, *Campylobacter jejuni* doylei 269 97, *Campylobacter jejuni* 81116, *Campylobacter jejuni, Campylobacter lari* RM2100, *Helicobacter hepaticus, Wolinella succinogenes, Tolumonas auensis* DSM 9187, *Pseudoalteromonas atlantica* T6c, *Shewanella pealeana* (ATCC 700345), *Legionella pneumophila* Paris, *Actinobacillus succinogenes* 130Z, *Pasteurella multocida, Francisella tularensis novicida* U112, *Francisella tularensis* holarctica, *Francisella tularensis* FSC 198, *Francisella tularensis tularensis, Francisella tularensis* WY96-3418, or *Treponema denticola* (ATCC 35405).

14. The method of claim 1, wherein the first insect strain and the second insect strain are species in an Order selected from the group consisting of: Diptera, Lepidoptera, and Coleoptera.

15. The method of claim 14, wherein:

the first and second insect strains are a mosquito species from the genera Stegomyia, *Aedes, Anopheles,* or *Culex;* or the first and second insect strains are a species selected from the group consisting of: a tephritid fruit fly selected from Medfly (*Ceratitis capitata*), Mexfly (*Anastrepha ludens*), Oriental fruit fly (*Bactrocera dorsalis*), Olive fruit fly (*Bactrocera oleae*), Melon fly (*Bactrocera cucurbitae*), Natal fruit fly (*Ceratitis rosa*), Cherry fruit fly (*Rhagoletis cerasi*), Queensland fruit fly (*Bactrocera tyroni*), Peach fruit fly (*Bactrocera zonata*), Caribbean fruit fly (*Anastrepha suspensa*), Oriental Fruit Fly (*Bactrocera dorsalis*), West Indian fruit fly (*Anastrepha obliqua*), the New World screwworm (*Cochliomyia hominivorax*), the Old World screwworm (*Chrysomya bezziana*), Australian sheep blowfly/greenbottle fly (*Lucilia cuprina*), the pink bollworm (*Pectinophora gossypiella*), the European Gypsy moth (*Lymantria dispar*), the Navel Orange Worm (*Amyelois transitella*), the Peach Twig Borer (*Anarsia lineatella*), the rice stem borer (*Tryporyza incertulas*), the noctuid moths, Heliothinae, the Japanese beetle (*Papilla japonica*), White-fringed beetle (*Graphognatus* spp.), Boll weevil (*Anthonomous grandis*), the Colorado potato beetle (*Leptinotarsa decemlineata*), the vine mealybug (*Planococcus ficus*), Asian citrus psyllid (*Diaphorina citri*), Spotted wing *drosophila* (*Drosophila suzukii*), Bluegreen sharpshooter (*Graphocephala atropunctata*), Glassy winged sharpshooter (*Homalodisca vitripennis*), Light brown apple moth (*Epiphyas postvittana*), Bagrada bug (*Bagrada hilaris*), Brown marmorated stink bug (*Halyomorpha halys*), Asian Gypsy Moth selected from the group of: *Lymantria dispar asiatica, Lymantria dispar japonica, Lymantria albescens, Lymantria umbrosa*, and *Lymantria postalba*, Asian longhorned beetle (*Anoplophora glabripennis*), Coconut Rhinoceros Beetle (*Oryctes rhinoceros*), Emerald Ash Borer (*Agrilus planipennis*), European Grapevine Moth (*Lobesia botrana*), European Gypsy Moth (*Lymantria dispar*), False Codling Moth (*Thaumatotibia leucotreta*), fire ants selected from *Solenopsis invicta* Buren, and *S. richteri* Forel, Old World Bollworm (*Helicoverpa armigera*), Spotted Lanternfly (*Lycorma delicatula*), Africanized honeybee (*Apis mellifera scutellata*), Fruit and shoot borer (*Leucinodes orbonalis*), corn root worm (*Diabrotica* spp.), Western corn rootworm (*Diabrotica virgifera*), Whitefly (*Bemisia tabaci*), House Fly (*Musca Domestica*), Green Bottle Fly (*Lucilia cuprina*), Silk Moth (*Bombyx mori*), Red Scale (*Aonidiella aurantia*), Dog heartworm (*Dirofilaria immitis*), Southern pine beetle (*Dendroctonus frontalis*), Avocado thrip (*Thysanoptera* Spp.), Botfly selected from *Oestridae* spp. and *Dermatobia hominis*), Horse Fly (*Tabanus sulcifrons*), Horn Fly (*Haematobia irritans*), Screwworm Fly selected from *Cochliomyia macellaria* (*C. macellaria*), *C. hominivorax, C. aldrichi*, or *C. minima*, Tsetse Fly (*Glossina* spp.), Warble Fly selected from *Hypoderma bovis* or *Hypoderma lineatum*, Spotted lanternfly (*Lycorma delicatula*), Khapra beetle (*Trogoderma granarium*), Honeybee mite (*Varroa destructor*), Termites (*Coptotermes formosanus*), Hemlock woolly adelgid (*Adelges tsugae*), Walnut twig beetle (*Pityophthorus juglandis*), European wood wasp (*Sirex noctilio*), Pink-spotted bollworm (*Pectinophora scutigera*), Two spotted spider mite (*Tertanychus urticae*), Diamondback moth (*Plutella xylostella*), Taro caterpillar (*Spodoptera litura*), Red flour beetle (*Tribolium castaneum*), Green peach aphid (*Myzus persicae*), Cotton Aphid (*Aphis gossypii*), Brown planthopper (*Nilaparvata lugens*), Beet armyworm (*Spodotera exigua*), Western flower *thrips* (*Frankliniella occidentalis*), Codling moth (*Cydia pomonella*), Cowpea weevil (*Callosobruchus maculatus*), Pea aphid (*Acyrthosiphon pisum*), Tomato leafminer (*Tuta absoluta*), Onion *thrips* (*Thrips tabaci*), and Cotton bollworm (*Helicoverpa armigera*).

16. A progeny of insect eggs produced by the method of claim 1, wherein the progeny's genome comprises:

(a) at least one nucleic acid sequence comprising at least one first guide polynucleotide targeting a female-essential genomic sequence that is required for female-specific viability, wherein the female-essential genomic sequence is a gene or a splice-variant of a gene selected from the group consisting of sex lethal (Sxl), transformer (Tra), and doublesex (Dsx);

(b) at least one nucleic acid sequence comprising at least one second guide polynucleotide targeting a male sterility genomic sequence that is required for male-specific fertility, wherein the male sterility genomic sequence is a βTubulin 85D (βTub) gene; and (c) a nucleic acid sequence encoding an endonuclease, wherein the endonuclease is directed by the first and second guide polynucleotides to enzymatically knock-out the female-essential genomic sequence and the male sterility genomic sequence, respectively, when present in the same insect.

17. A genetically modified sterile male insect whose genome comprises:

(a) at least one nucleic acid sequence comprising at least one first guide polynucleotide targeting a female-essential genomic sequence that is required for female-specific viability, wherein the female-essential genomic sequence is a gene or a splice-variant of a gene selected from the group consisting of sex lethal (Sxl), transformer (Tra), and doublesex (Dsx);

(b) at least one nucleic acid sequence comprising at least one second guide polynucleotide targeting a male sterility genomic sequence that is required for male-specific fertility, wherein the male sterility genomic sequence is a βTubulin 85D (βTub) gene; and (c) a nucleic acid sequence encoding an endonuclease, wherein the endonuclease is directed by the first and second guide polynucleotides to enzymatically knock-out the female-essential genomic sequence and the male sterility genomic sequence, respectively, in the genome of the genetically modified sterile male insect, and wherein the genetically modified sterile male insect is capable of increasing the rate of unhatched eggs by mating with wild-type female insects.

18. The method of claim 13, wherein the variant of SpCas9, SaCas9, or FnCas9 comprises a protospacer adjacent motif (PAM) SpCas9 (xCas9), high fidelity SpCas9 (SpCas9-HF1), a high fidelity SaCas9, or a high fidelity FnCas9.

19. The method of claim 13, wherein the variant of the Cas9 protein fused with the FokI nuclease or variant thereof comprises a catalytically inactive Cas9 (dead Cas9).

20. The method of claim 15, wherein the mosquito species is selected from the group consisting of: *Aedes aegypti, Aedes albopictus, Ochlerotatus triseriatus* (*Aedes triseriatus*), *Anopheles stephensi, Anopheles albimanus, Anopheles gambiae, Anopheles quadrimaculatus, Anopheles freeborni, Culex species*, and *Culiseta melanura*.

21. The insect of claim 17, wherein the genetically modified sterile male insect has a lifespan that is equal to or longer than its corresponding wild-type male insect.

\* \* \* \* \*